(12) United States Patent
Vigneault et al.

(10) Patent No.: US 10,590,483 B2
(45) Date of Patent: Mar. 17, 2020

(54) HIGH-THROUGHPUT NUCLEOTIDE LIBRARY SEQUENCING

(71) Applicant: AbVitro, LLC, Boston, MA (US)

(72) Inventors: Francois Vigneault, Beverly, MA (US); Adrian Wrangham Briggs, Cambridge, MA (US); Christopher Ryan Clouser, Salem, MA (US); Stephen Jacob Goldfless, Cambridge, MA (US); Sonia Timberlake, Brookline, MA (US)

(73) Assignee: AbVitro LLC, Boston, MA (US)

( * ) Notice: Subject to any disclaimer, the term of this patent is extended or adjusted under 35 U.S.C. 154(b) by 516 days.

(21) Appl. No.: 14/854,399

(22) Filed: Sep. 15, 2015

(65) Prior Publication Data

US 2016/0244825 A1    Aug. 25, 2016

Related U.S. Application Data

(60) Provisional application No. 62/050,549, filed on Sep. 15, 2014, provisional application No. 62/051,832, filed on Sep. 17, 2014.

(51) Int. Cl.
| | | |
|---|---|---|
| C12Q 1/68 | (2018.01) | |
| C12Q 1/6874 | (2018.01) | |
| C12N 15/10 | (2006.01) | |

(52) U.S. Cl.
CPC ....... C12Q 1/6874 (2013.01); C12N 15/1093 (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 4,656,134 A | 4/1987 | Ringold | |
| 4,683,195 A * | 7/1987 | Mullis | C12Q 1/6827 435/6.1 |
| 4,683,202 A | 7/1987 | Mullis | |
| 4,766,067 A | 8/1988 | Biswas | |
| 4,795,699 A | 1/1989 | Tabor et al. | |
| 4,800,159 A | 1/1989 | Mullis et al. | |
| 4,889,818 A | 12/1989 | Gelfand et al. | |
| 4,921,794 A | 5/1990 | Tabor et al. | |
| 4,965,188 A | 10/1990 | Mullis et al. | |
| 4,988,617 A | 1/1991 | Landegren et al. | |
| 4,994,370 A | 2/1991 | Silver et al. | |
| 5,066,584 A | 11/1991 | Gyllensten et al. | |
| 5,091,310 A | 2/1992 | Innis | |
| 5,122,464 A | 6/1992 | Wilson et al. | |
| 5,130,238 A | 7/1992 | Malek et al. | |
| 5,142,033 A | 8/1992 | Innis | |
| 5,143,854 A | 9/1992 | Pirrung et al. | |
| 5,168,038 A | 12/1992 | Tecott et al. | |
| 5,210,015 A | 5/1993 | Gelfand et al. | |
| 5,242,794 A | 9/1993 | Whiteley et al. | |
| 5,242,974 A | 9/1993 | Holmes | |
| 5,252,743 A | 10/1993 | Barrett et al. | |
| 5,324,633 A | 6/1994 | Fodor et al. | |
| 5,384,261 A | 1/1995 | Winkler et al. | |
| 5,405,783 A | 4/1995 | Pirrung et al. | |
| 5,424,186 A | 6/1995 | Fodor et al. | |
| 5,451,683 A | 9/1995 | Barrett et al. | |
| 5,482,867 A | 1/1996 | Barrett et al. | |
| 5,491,074 A | 2/1996 | Aldwin et al. | |
| 5,494,810 A | 2/1996 | Barany et al. | |
| 5,527,681 A | 6/1996 | Holmes | |
| 5,550,215 A | 8/1996 | Holmes | |
| 5,571,639 A | 11/1996 | Hubbell et al. | |
| 5,578,832 A | 11/1996 | Trulson et al. | |
| 5,593,839 A | 1/1997 | Hubbell et al. | |
| 5,599,695 A | 2/1997 | Pease et al. | |
| 5,624,711 A | 4/1997 | Sundberg et al. | |
| 5,631,734 A | 5/1997 | Stern et al. | |
| 5,700,907 A | 12/1997 | Hercend et al. | |
| 5,744,305 A | 4/1998 | Fodor et al. | |
| 5,795,716 A | 8/1998 | Chee | |
| 5,831,070 A | 11/1998 | Pease et al. | |
| 5,837,832 A | 11/1998 | Chee et al. | |
| 5,856,101 A | 1/1999 | Hubbell et al. | |
| 5,858,659 A | 1/1999 | Sapolsky et al. | |
| 5,925,517 A | 7/1999 | Tyagi et al. | |

(Continued)

FOREIGN PATENT DOCUMENTS

| | | |
|---|---|---|
| EP | 0404097 A2 | 12/1990 |
| WO | WO 93/11161 A1 | 6/1993 |

(Continued)

OTHER PUBLICATIONS

Kozarewa et al. Nature Methods 6(4) : 291 (2009).*
Loh et al., Blood 113(22) :5476 (2009).*
Loh et al., Cell Stem Cell7 :15 (2010).*
Metzker M., Nature Reviews Genetics 11 :31 (Jan. 2011).*
Ramskold et al., Nature Biotechnology 10(8) : 777 (2012).*
Sherwold et al., Journal of Immunology 179 :928 (2007).*
Shapiro et al., Nature review Genetics 14 :618 (Sep. 2013).*
Soumillion et al., bioRxiv preprint posted online (Mar. 5, 2014).*

(Continued)

*Primary Examiner* — Ethan C Whisenant

(74) *Attorney, Agent, or Firm* — Finnegan, Henderson, Farabow, Garrett & Dunner, LLP

(57) ABSTRACT

Provided herein are methods and composition for immune repertoire sequencing and single cell barcoding. The methods and compositions can be used to pair any two sequences originating from a single cell, such as heavy and light chain antibody sequences, alpha and beta chain T-cell receptor sequences, or gamma and delta chain T-cell receptor sequences, for antibody and T-cell receptor discovery, disease and immune diagnostics, and low error sequencing.

39 Claims, 12 Drawing Sheets

Specification includes a Sequence Listing.

(56) References Cited

U.S. PATENT DOCUMENTS

| | | |
|---|---|---|
| 5,936,324 A | 8/1999 | Montagu |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,025,601 A | 2/2000 | Trulson et al. |
| 6,033,860 A | 3/2000 | Lockhart et al. |
| 6,040,193 A | 3/2000 | Winkler et al. |
| 6,090,555 A | 7/2000 | Fiekowsky et al. |
| 6,136,269 A | 10/2000 | Winkler et al. |
| 6,174,670 B1 | 1/2001 | Wittwer et al. |
| 6,268,152 B1 | 7/2001 | Fodor et al. |
| 6,269,846 B1 | 8/2001 | Overbeck et al. |
| 6,306,597 B1 | 10/2001 | Macevicz |
| 6,428,752 B1 | 8/2002 | Montagu |
| 6,458,530 B1 | 10/2002 | Morris et al. |
| 6,569,627 B2 | 5/2003 | Wittwer et al. |
| 6,582,938 B1 | 6/2003 | Su et al. |
| 6,797,470 B2 | 9/2004 | Barany et al. |
| 7,037,687 B2 | 5/2006 | Williams et al. |
| 7,083,917 B2 | 8/2006 | Barany et al. |
| 7,166,434 B2 | 1/2007 | Barony et al. |
| 7,169,560 B2 | 1/2007 | Lapidus et al. |
| 7,232,656 B2 | 6/2007 | Balasubramanian et al. |
| 7,244,567 B2 | 7/2007 | Chen et al. |
| 7,306,908 B2 | 12/2007 | Maruyama et al. |
| 7,320,865 B2 | 1/2008 | Barany et al. |
| 7,323,305 B2 | 1/2008 | Leamon et al. |
| 7,332,285 B2 | 2/2008 | Barany et al. |
| 7,364,858 B2 | 4/2008 | Barany et al. |
| 7,375,211 B2 | 5/2008 | Kou |
| 7,414,111 B2 | 8/2008 | Maruyama et al. |
| 7,429,453 B2 | 9/2008 | Barany et al. |
| 7,455,965 B2 | 11/2008 | Barany et al. |
| 7,537,897 B2 | 5/2009 | Brenner et al. |
| 7,556,924 B2 | 7/2009 | Barany et al. |
| 7,567,870 B1 | 7/2009 | Hood et al. |
| 7,598,035 B2 | 10/2009 | Macevicz |
| 7,622,280 B2 | 11/2009 | Holliger et al. |
| 7,622,281 B2 | 11/2009 | Ronaghi et al. |
| 7,645,596 B2 | 1/2010 | Williams et al. |
| 7,691,994 B2 | 4/2010 | Brewer et al. |
| 7,749,697 B2 | 7/2010 | Oleksiewicz et al. |
| 7,767,435 B2 | 8/2010 | Chiu et al. |
| 7,769,400 B2 | 8/2010 | Backholm et al. |
| 7,785,783 B2 | 8/2010 | Morley et al. |
| 7,820,382 B2 | 10/2010 | Bauer et al. |
| 7,842,457 B2 | 11/2010 | Berka et al. |
| 7,879,579 B2 | 2/2011 | Barany et al. |
| 7,892,746 B2 | 2/2011 | Barany et al. |
| 7,892,747 B2 | 2/2011 | Barany et al. |
| 7,893,233 B2 | 2/2011 | Barany et al. |
| 7,915,036 B2 | 3/2011 | Morgan et al. |
| 8,012,690 B2 | 9/2011 | Berka et al. |
| 8,036,834 B2 | 10/2011 | Hood et al. |
| 8,048,627 B2 | 11/2011 | Dressman et al. |
| 8,143,007 B2 | 3/2012 | Devinder et al. |
| 8,148,068 B2 | 4/2012 | Brenner |
| 8,158,359 B2 | 4/2012 | Leamon et al. |
| 8,168,385 B2 | 5/2012 | Brenner |
| 8,236,503 B2 | 8/2012 | Faham et al. |
| 8,268,564 B2 | 9/2012 | Roth et al. |
| 8,293,483 B2 | 10/2012 | Yu |
| 9,816,088 B2 | 11/2017 | Vigneault et al. |
| 2002/0192687 A1 | 12/2002 | Mirkin et al. |
| 2004/0185484 A1 | 9/2004 | Costa et al. |
| 2005/0074787 A1 | 4/2005 | Fan et al. |
| 2006/0008824 A1 | 1/2006 | Ronaghi et al. |
| 2006/0046258 A1 | 3/2006 | Lapidus et al. |
| 2006/0085139 A1 | 4/2006 | Collette et al. |
| 2006/0134125 A1 | 6/2006 | Luxemburg et al. |
| 2006/0234234 A1 | 10/2006 | Van Dongen et al. |
| 2007/0141048 A1 | 6/2007 | Oleksiewicz et al. |
| 2007/0160994 A1 | 7/2007 | Lim et al. |
| 2007/0161001 A1 | 7/2007 | Leshkowitz |
| 2007/0161031 A1 | 7/2007 | Trinklein et al. |
| 2008/0038559 A1 | 2/2008 | True |
| 2008/0108804 A1 | 5/2008 | Hayashizaki et al. |
| 2008/0166704 A1 | 7/2008 | Marche et al. |
| 2008/0166718 A1 | 7/2008 | Lim et al. |
| 2008/0182262 A1 | 7/2008 | Perez et al. |
| 2008/0248484 A1 | 10/2008 | Bauer |
| 2008/0269068 A1 | 10/2008 | Church et al. |
| 2008/0280282 A1 | 11/2008 | Bauer, Jr. |
| 2009/0048124 A1 | 2/2009 | Leamon et al. |
| 2009/0149340 A1 | 6/2009 | True |
| 2009/0163366 A1 | 6/2009 | Nickerson et al. |
| 2009/0286687 A1 | 11/2009 | Dressman et al. |
| 2009/0325169 A1 | 12/2009 | Walder et al. |
| 2010/0021896 A1 | 1/2010 | Han |
| 2010/0022414 A1 | 1/2010 | Link et al. |
| 2010/0040606 A1 | 2/2010 | Lantto et al. |
| 2010/0062494 A1 | 3/2010 | Church et al. |
| 2010/0069250 A1 | 3/2010 | White, III et al. |
| 2010/0094795 A1 | 4/2010 | Irizarry et al. |
| 2010/0099103 A1 | 4/2010 | Hsieh et al. |
| 2010/0151471 A1 | 6/2010 | Faham et al. |
| 2010/0167353 A1 | 7/2010 | Walder et al. |
| 2010/0186097 A1 | 7/2010 | Lowe et al. |
| 2010/0190153 A1 | 7/2010 | Diehl et al. |
| 2010/0204059 A1 | 8/2010 | Ke et al. |
| 2010/0255471 A1 | 10/2010 | Clarke et al. |
| 2010/0285984 A1 | 11/2010 | Wettstein et al. |
| 2010/0292083 A1 | 11/2010 | Kolkman |
| 2010/0304996 A1 | 12/2010 | Seyfert et al. |
| 2010/0310558 A1 | 12/2010 | Oleksiewicz et al. |
| 2010/0311054 A1 | 12/2010 | Miller et al. |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0021369 A1 | 1/2011 | Mhlanga et al. |
| 2011/0053803 A1 | 3/2011 | Ge et al. |
| 2011/0059435 A1 | 3/2011 | Vogelstein et al. |
| 2011/0086051 A1 | 4/2011 | Zuckerman et al. |
| 2011/0182902 A1 | 7/2011 | Panigrahi et al. |
| 2011/0201526 A1 | 8/2011 | Berka et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0244455 A1 | 10/2011 | Larson et al. |
| 2011/0250597 A1 | 10/2011 | Larson et al. |
| 2011/0312505 A1 | 12/2011 | Reddy et al. |
| 2012/0010086 A1 | 1/2012 | Froehlich et al. |
| 2012/0010091 A1* | 1/2012 | Linnarson ........ C12N 15/1065 506/7 |
| 2012/0015829 A1 | 1/2012 | Wiley |
| 2012/0058902 A1 | 3/2012 | Livingston et al. |
| 2012/0071331 A1 | 3/2012 | Casbon et al. |
| 2012/0135409 A1 | 5/2012 | Faham et al. |
| 2012/0151610 A1 | 6/2012 | Craig et al. |
| 2012/0183967 A1 | 7/2012 | Dressman et al. |
| 2012/0183969 A1 | 7/2012 | Han |
| 2012/0220466 A1 | 8/2012 | Fire et al. |
| 2012/0220494 A1* | 8/2012 | Samuels ........... C12N 15/1075 506/16 |
| 2012/0238475 A1 | 9/2012 | Leamon et al. |
| 2012/0264646 A1 | 10/2012 | Link et al. |
| 2012/0266260 A1 | 10/2012 | Suzuki et al. |
| 2012/0270295 A1 | 10/2012 | Choo et al. |
| 2012/0283134 A1 | 11/2012 | Yu |
| 2012/0295810 A1 | 11/2012 | Quake et al. |
| 2012/0302448 A1 | 11/2012 | Hutchison et al. |
| 2012/0316074 A1 | 12/2012 | Saxonov |
| 2013/0005584 A1 | 1/2013 | Faham et al. |
| 2013/0005792 A1 | 1/2013 | Haining et al. |
| 2013/0017957 A1 | 1/2013 | Faham et al. |
| 2013/0018173 A1 | 1/2013 | Simard |
| 2013/0071860 A1 | 3/2013 | Hale et al. |
| 2013/0079231 A1 | 3/2013 | Pushkarev et al. |
| 2013/0130932 A1 | 5/2013 | Yu |
| 2013/0274117 A1* | 10/2013 | Church ............ C12Q 1/6869 506/4 |
| 2014/0357500 A1 | 12/2014 | Vigneault et al. |

(56) References Cited

U.S. PATENT DOCUMENTS

| | | | | |
|---|---|---|---|---|
| 2015/0057163 | A1* | 2/2015 | Rotem | C12Q 1/6869 506/2 |
| 2015/0329891 | A1* | 11/2015 | Tan | C12Q 1/6804 435/91.1 |
| 2016/0090592 | A1* | 3/2016 | Banyai | C12N 15/66 506/17 |
| 2016/0122753 | A1* | 5/2016 | Mikkelsen | C12Q 1/6844 506/4 |
| 2016/0377631 | A1* | 12/2016 | Kuchroo | C12Q 1/6883 424/134.1 |

FOREIGN PATENT DOCUMENTS

| | | |
|---|---|---|
| WO | WO 93/12227 A1 | 6/1993 |
| WO | WO-9810284 A1 | 3/1998 |
| WO | WO-9844151 A1 | 10/1998 |
| WO | WO 99/36760 A1 | 7/1999 |
| WO | WO 99/51773 A1 | 10/1999 |
| WO | WO 00/58516 A2 | 10/2000 |
| WO | WO-0075374 A1 | 12/2000 |
| WO | WO 01/40803 A1 | 6/2001 |
| WO | WO 01/58593 A1 | 8/2001 |
| WO | WO 01/89788 A2 | 11/2001 |
| WO | WO 2004/002627 A2 | 1/2004 |
| WO | WO-2004003820 A2 | 1/2004 |
| WO | WO 2004/091763 A2 | 10/2004 |
| WO | WO 2005/021151 A1 | 3/2005 |
| WO | WO-2005042774 A2 | 5/2005 |
| WO | WO-2005042774 A3 | 6/2005 |
| WO | WO-2005059176 A1 | 6/2005 |
| WO | WO-2004003820 A3 | 7/2005 |
| WO | WO-2005084134 A2 | 9/2005 |
| WO | WO 2006/040551 A2 | 4/2006 |
| WO | WO 2006/040554 A1 | 4/2006 |
| WO | WO 2006/096571 A2 | 9/2006 |
| WO | WO-2007050465 A2 | 5/2007 |
| WO | WO 2007/081385 A2 | 7/2007 |
| WO | WO 2007/089541 A2 | 8/2007 |
| WO | WO 2008/063227 A2 | 5/2008 |
| WO | WO-2008076842 A2 | 6/2008 |
| WO | WO-2009076485 A2 | 6/2009 |
| WO | WO-2010003132 A1 | 1/2010 |
| WO | WO 2010/036352 A1 | 4/2010 |
| WO | WO-2010054288 A2 | 5/2010 |
| WO | WO-2010151416 A1 | 12/2010 |
| WO | WO-2011106558 A1 | 9/2011 |
| WO | WO-2011119980 A1 | 9/2011 |
| WO | WO-2011139371 A1 | 11/2011 |
| WO | WO-2011140433 A2 | 11/2011 |
| WO | WO-2012042374 A2 | 4/2012 |
| WO | WO-2012048340 A2 | 4/2012 |
| WO | WO-2012048341 A1 | 4/2012 |
| WO | WO-2012072705 A1 | 6/2012 |
| WO | WO-2012092376 A2 | 7/2012 |
| WO | WO-2012083225 A2 | 8/2012 |
| WO | WO-2012142213 A2 | 10/2012 |
| WO | WO-2012148497 A2 | 11/2012 |
| WO | WO-2013044234 A1 | 3/2013 |
| WO | WO-2014071361 A1 | 5/2014 |
| WO | WO-2014144495 A1 | 9/2014 |
| WO | WO-2014201273 A1 | 12/2014 |
| WO | WO-2015121236 A1 | 8/2015 |
| WO | WO-2016044227 A1 | 3/2016 |

OTHER PUBLICATIONS

Yu et al. Science 324: 797 (May 8, 2009).*
Aljanabi, et al. Universal and rapid salt-extraction of high quality genomic DNA for PCR-based techniques. Nucleic Acids Res. Nov. 15, 1997;25(22):4692-3.
Altschul, et al. Gapped BLAST and PSI-BLAST: a new generation of protein database search programs. Nucleic Acids Res. Sep. 1, 1997;25(17):3389-402.
Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.
Bibkova, et al. High-throughput DNA methylation profiling using universal bead arrays. Genome Res. Mar. 2006;16(3):383-93. Epub Jan. 31, 2006.
Bird, et al. Single-chain antigen-binding proteins. Science. Oct. 21, 1988;242(4877):423-6.
Brenner. A cultivated taste for yeast. Genome Biol. 2000;1(1):REVIEWS103. Epub Apr. 27, 2000.
Brown, et al. Chemical synthesis and cloning of a tyrosine tRNA gene. Methods Enzymol. 1979;68:109-51.
De Wildt, et al. Antibody arrays for high-throughput screening of antibody-antigen interactions. Nat Biotechnol. Sep. 2000;18(9):989-94.
Dear. One by one: Single molecule tools for genomics. Brief Funct Genomic Proteomic. Jan. 2003;1(4):397-416.
Dekosky, et al. In-depth determination and analysis of the human paired heavy- and light-chain antibody repertoire. Nat Med. Jan. 2015;21(1):86-91. doi: 10.1038/nm.3743. Epub Dec. 15, 2014.
Diviacco, et al. A novel procedure for quantitative polymerase chain reaction by coamplification of competitive templates. Gene. Dec. 15, 1992;122(2):313-20.
Eason, et al. Characterization of synthetic DNA bar codes in *Saccharomyces cerevisiae* gene-deletion strains. Proc Natl Acad Sci U S A. Jul. 27, 2004;101(30):11046-51. Epub Jul. 16, 2004.
Edgar. MUSCLE: multiple sequence alignment with high accuracy and high throughput. Nucleic Acids Res. Mar. 19, 2004;32(5):1792-7. Print 2004.
Eroshkin, et al. bNAber: database of broadly neutralizing HIV antibodies. Nucleic Acids Res. Jan. 2014;42(Database issue):D1133-9. doi: 10.1093/nar/gkt1083. Epub Nov. 7, 2013.
Freeman, et al. Quantitative RT-PCR: pitfalls and potential. Biotechniques. Jan. 1999;26(1):112-126.
Ge. UPA, a universal protein array system for quantitative detection of protein-protein, protein-DNA, protein-RNA and protein-ligand interactions. Nucleic Acids Res. Jan. 15, 2000;28(2):e3.
Giaever, et al. Chemogenomic profiling: identifying the functional interactions of small molecules in yeast. Proc Natl Acad Sci U S A. Jan. 20, 2004;101(3):793-8. Epub Jan. 12, 2004.
Giudicelli, et al. IMGT/LIGM-DB, the IMGT comprehensive database of immunoglobulin and T cell receptor nucleotide sequences. Nucleic Acids Res. Jan. 1, 2006;34(Database issue):D781-4.
Guindon, et al. New algorithms and methods to estimate maximum-likelihood phylogenies: assessing the performance of PhyML 3.0. Syst Biol. May 2010;59(3):307-21. doi: 10.1093/sysbio/syq010. Epub Mar. 29, 2010.
Gupta, et al. Change-O: a toolkit for analyzing large-scale B cell immunoglobulin repertoire sequencing data. Bioinformatics. Oct. 15, 2015;31(20):3356-8. doi: 10.1093/bioinformatics/btv359. Epub Jun. 10, 2015.
Hammond, et al. Extraction of DNA from preserved animal specimens for use in randomly amplified polymorphic DNA analysis. Anal Biochem. Sep. 5, 1996;240(2):298-300.
Harris, et al. Single-molecule DNA sequencing of a viral genome. Science. Apr. 4, 2008;320(5872):106-9. doi: 10.1126/science.1150427.
Huson, et al. Dendroscope 3: an interactive tool for rooted phylogenetic trees and networks. Syst Biol. Dec. 1, 2012;61(6):1061-7. doi: 10.1093/sysbio/sys062. Epub Jul. 10, 2012.
Huston, et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Jones, et al. Replacing the complementarity-determining regions in a human antibody with those from a mouse. Nature. May 29-Jun. 4, 1986;321(6069):522-5.
Junier, et al. The Newick utilities: high-throughput phylogenetic tree processing in the UNIX shell. Bioinformatics. Jul. 1, 2010;26(13):1669-70. doi: 10.1093/bioinformatics/btq243. Epub May 13, 2010.

(56) References Cited

OTHER PUBLICATIONS

Karlin, et al. Applications and statistics for multiple high-scoring segments in molecular sequences. Proc Natl Acad Sci U S A. Jun. 15, 1993;90(12):5873-7.
Kumar, et al. Emerging technologies in yeast genomics. Nat Rev Genet. Apr. 2001;2(4):302-12.
Larrick, et al. Polymerase chain reaction using mixed primers: cloning of human monoclonal antibody variable region genes from single hybridoma cells Bio/Technology 7:934 (1989).
Lueking, et al. Protein microarrays for gene expression and antibody screening. Anal Biochem. May 15, 1999;270(1):103-11.
MacBeath, et al. Printing Proteins as Microarrays for High-Throughput Function Determination. Science. 2000; 289:1760-1763.
MacKay, et al. Real-time PCR in virology. Nucleic Acids Res. Mar. 15, 2002;30(6):1292-305.
Margulies, et al. Genome sequencing in microfabricated high-density picolitre reactors. Nature. Sep. 15, 2005;437(7057):376-80. Epub Jul. 31, 2005.
McCaughan, et al. Single-molecule genomics. J Pathol. Jan. 2010;220(2):297-306. doi: 10.1002/path.2647.
Narang, et al. Improved phosphotriester method for the synthesis of gene fragments. Methods Enzymol. 1979;68:90-8.
Nei, et al. Mathematical model for studying genetic variation in terms of restriction endonucleases. Proc Natl Acad Sci U S A. Oct. 1979;76(10):5269-73.
Nicholls, et al. An improved method for generating single-chain antibodies from hybridomas. J Immunol Methods. Sep. 27, 1993;165(1):81-91.
Osbourn, et al. Directed selection of MIP-1 alpha neutralizing CCR5 antibodies from a phage display human antibody library. Nat Biotechnol. Aug. 1998;16(8):778-81.
Petit, et al. Optimization of tumor xenograft dissociation for the profiling of cell surface markers and nutrient transporters. Lab Invest. May 2013;93(5):611-21. doi: 10.1038/labinvest.2013.44. Epub Mar. 4, 2013.
Presta. Antibody engineering. Current Opinion in Structural Biology 1992, 2:593-596.
Riechmann, et al. Reshaping human antibodies for therapy. Nature. Mar. 24, 1988;332(6162):323-7.
Soni, et al. Progress toward ultrafast DNA sequencing using solid-state nanopores. Clin Chem. Nov. 2007;53(11):1996-2001. Epub Sep. 21, 2007.
Stern, et al. B cells populating the multiple sclerosis brain mature in the draining cervical lymph nodes. Sci Transl Med. Aug. 6, 2014;6(248):248ra107. doi: 10.1126/scitranslmed.3008879.
Sunnucks, et al. Microsatellite and chromosome evolution of parthenogenetic sitobion aphids in Australia. Genetics. Oct. 1996;144(2):747-56.
Vander Heiden, et al. pRESTO: a toolkit for processing high-throughput sequencing raw reads of lymphocyte receptor repertoires. Bioinformatics. Jul. 1, 2014;30(13):1930-2. doi: 10.1093/bioinformatics/btu138. Epub Mar. 10, 2014.
Walker, et al. Broad neutralization coverage of HIV by multiple highly potent antibodies. Nature. Sep. 22, 2011;477(7365):466-70. doi: 10.1038/nature10373.
Ward, et al. Binding activities of a repertoire of single immunoglobulin variable domains secreted from *Escherichia coli*. Nature. Oct. 12, 1989;341(6242):544-6.
Waterhouse, et al. Jalview Version 2—a multiple sequence alignment editor and analysis workbench. Bioinformatics. May 1, 2009;25(9):1189-91. doi: 10.1093/bioinformatics/btp033. Epub Jan. 16, 2009.
Watkins, et al. Isolation of immune cells from primary tumors. J Vis Exp. Jun. 16, 2012;(64):e3952. doi: 10.3791/3952.
Wickham, et al. dplyr: A Grammar of Data Manipulation. Sep. 1, 2015. 72 pages. at <http://CRAN.Rproject.org/package=dplyr>.
Wickham. ggplot2: elegant graphics for data analysis. (Springer New York, 2009). at <http://had.co.nz/ggplot2/book>.

Winzeler, et al. Functional characterization of the S. cerevisiae genome by gene deletion and parallel analysis. Science. Aug. 6, 1999;285(5429):901-6.
Ye, et al. IgBLAST: an immunoglobulin variable domain sequence analysis tool. Nucleic Acids Res. Jul. 2013;41(Web Server issue):W34-40. doi: 10.1093/nar/gkt382. Epub May 13, 2013.
Zapata, et al. Engineering linear F(ab')2 fragments for efficient production in *Escherichia coli* and enhanced antiproliferative activity. Protein Eng. Oct. 1995;8(10):1057-62.
Zimmerman, et al. Technical aspects of quantitative competitive PCR. Biotechniques. 1996; 21:268-279.
Alon et al., Barcoding bias in high-throughput multiplex sequencing of miRNA, Genome Res., 21(9):1506-1511 (2011).
Boyd, et al. Measurement and clinical monitoring of human lymphocyte clonality by massively parallel VDJ pyrosequencing. Sci Transl Med. Dec. 23, 2009;1(12):12ra23.
Brenner, C. Chemical genomics in yeast. Genome Biology. 2004; 5:240.
Dekosky, et al. High-throughput sequencing of the paired human immunoglobulin heavy and light chain repertoire. Nat Biotechnol. Feb. 2013;31(2):166-9, doi: 10.1038/nbt.2492. Epub Jan. 20, 2013.
Edd, et al. Controlled encapsulation of single-cells into monodisperse picolitre drops. Lab Chip. Aug. 2008;8(8):1262-4. doi: 10.1039/b805456h. Epub Jun. 13, 2008.
Gustincich, et al. A fast method for high-quality genomic DNA extraction from whole human blood. Biotechniques. Sep. 1991;11(3):298-300, 302.
Hoffmann, et al DNA bar coding and pyrosequencing to identify rare HIV drug resistance mutations. Nucleic Acids Res. 2007;35(13):e91. Epub Jun. 18, 2007.
International Search Report and Written Oppinion dated Jul. 24, 2014 for PCT/US2014/028925.
International Search Report and Written Opinion dated Dec. 22, 2015 for International Application No. PCT/US2015/050119.
Jones. High-Throughput Sequencing and Metagenomics. Estuaries and Coasts (Impact Factor: 2.56). Jan. 2010; 33(4):944-952. DOI:10.1007/s12237-009-9182-8.
Kinde, et al. Detection and quantification of rare mutations with massively parallel sequencing. Proc Natl. Acad Sci U S A. Jun. 7, 2015;108(23):9530-5. doi 10.1073/pnas.1105422108. Epub May 17, 2011.
Kircher et al., Double indexing overcomes inaccuracies in multiplex sequencing on the Illumina platform, Nucleic Acids Res., 40(1): e3 (8 pages) (2012).
Kivioja, et al. Counting absolute numbers of molecules using unique molecular identifiers. Nat Methods. Nov. 20, 2011;9(1):72-4. doi: 10.1038/nmeth.1778.
Kohler, et al. Continuous cultures of fused cells secretin antibody of predefined specificity. Nature. Aug. 7, 1975;256(5517):495-7.
Kohler et al. Derivation of specific antibody-producing tissue culture and tumor lines by cell fusion. European Journal of Immunology, 6.7 (1978): 511-519.
Lo. Transplantation monitoring by plasma DNA sequencing. Clin Chem. Jul. 2011;57(7):941-2. doi: 10.1373/clinchem.2011.166686.
Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.
Meijer, et al. Isolation of human antibody repertoies with preservation of the natural heavy and light chain pairing. J Mol Biol. 2006;358(3):764-72. Epub 2006.
Muyldermans, et al. Sequence and structure of VH domain from naturally occuring camel heavy chain Immunoglobulins lacking light chains. Protien Engineering 7(9):1129-1135, 1994.
Parameswaran, et al. A pyrosequencing-tailored nucleotide barcode design unveils opportunities for large-scale sample multiplexing. Nucleic Acids Res. 2007;35(19):e130. Epub Oct. 11, 2007.
Snyder, et al. Universal noninvasive detection of solid organ transplant rejection. Proc Natl Acad Sci U S A. Apr. 12, 2011;108(15):6229-34. doi: 10.1073/pnas.1013924108. Epub Mar. 28, 2011.
Warren, et al. Profiling model T-cell metagenomes with short reads. Bioinformatics. Feb. 15, 2009;25(4):458-64. doi: 10.1093/bioinformatics/btq010. Epub Jan. 9, 2009.

(56) References Cited

OTHER PUBLICATIONS

Weistein, et al. High-throughput sequencing of the zebrafish antibody repertoire. Science. May 8, 2009;324(5928):807-10. doi: 10.1126/science.1170020.

Spencer et al., Massively parallel sequencing of single cells by epicPCR links functional genes with phylogenetic markers—Supplementary Information, ISME J., 22 pages (2015).

Spencer et al., Massively parallel sequencing of single cells by epicPCR links functional genes with phylogenetic markers, The ISME Journal, 10: 427-436 (2016).

* cited by examiner

HIGH-THROUGHPUT NUCLEOTIDE LIBRARY SEQUENCING

CROSS-REFERENCE

This application claims priority to U.S. Provisional Application No. 62/050,549, filed Sep. 15, 2014, and U.S. Provisional Application No. 62/051,832, filed Sep. 17, 2014, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 29, 2016, is named 44243-709.201_SL.txt and is 14,937 bytes in size.

BACKGROUND

Current antibody display technologies (phage, yeast, ribosome, mammalian, etc.) are limited because the quality of the selected antibody candidates is limited by the starting library from which they are generated. Approaches, such as combinatorial and "intelligent" antibody design approaches and hybridoma discovery approaches, often yield synthetic antibodies that present downstream complications including large scale expression difficulties, high risk of immunogenicity in patients, and lack of sufficient immune function other than high binding affinities. Few antibodies derived from display technologies have successfully passed clinical trials in the last decade, even when demonstrating positive pre-clinical characteristics. Currently, the ability to predict or understand the mechanism by which a particular antibody sequence recognizes and activates the immune response against a foreign target has remained elusive. Thus, there is a need in the art for methods to discover and generate antibodies that have high binding affinities, can be generated on a large scale, and have sufficient immune function. The methods described herein aim to utilize the millions of years of immune repertoire evolution to meet these needs and to further the understanding of these concepts and how they relate to the generation of antibodies. The methods described herein can be used to produce a library of antibody sequences and/or antibodies for selection of high quality antibody candidates.

The human antibody repertoire is almost unlimited in its complexity and size. As a result, combinatorial libraries have statistically been demonstrated to rarely yield correct heavy ($V_H$) or light ($V_L$) chain pairing. Others have focused on shuffling the only of the most frequently expressed framework families of complementarity determining regions (CDRs) (such as V3-23, V1-69, or matching $V_H$ and $V_L$ frequencies), and therefore limited repertoire diversity to a manageable size. It was expected that the most frequently expressed family would be more frequently selected and evolved during an immune response. Surprisingly, through the use of immune sequencing of human antibody repertoires, it has been discovered that there is no relation between antibody framework expression frequencies and the activation potential of an antibody in response to an immune challenge. The methods described herein can be used to design and/or generate a non-limiting antibody library to overcome these challenges for antibody discovery and selection. Autoimmune, cancer, infectious and normal/healthy donor libraries can be generated for personalized medicine to address fundamental unmet biological needs.

SUMMARY

In one aspect, provided herein is a method comprising: forming a plurality of vessels each comprising a single cell from a sample comprising a plurality of cells, a plurality of molecular barcoded polynucleotides, and a vessel barcoded polynucleotide; producing: a first complementary polynucleotide that is complementary to a first cell polynucleotide from the single cell, and a second complementary polynucleotide that is complementary to a second cell polynucleotide from the single cell; attaching: a first molecular barcoded polynucleotide of the plurality to the first complementary polynucleotide, and a second molecular barcoded polynucleotide to the second complementary polynucleotide, thereby forming a first and a second single cell single-barcoded polynucleotide; and attaching the vessel barcoded polynucleotide, or an amplified product thereof to the first single cell single-barcoded polynucleotide, and the second single cell single-barcoded polynucleotide, thereby forming a first and a second single cell dual-barcoded sequences.

In one aspect, provided herein is a composition comprising: a plurality of vessels each comprising a single cell from a sample comprising a plurality of cells, a plurality of molecular barcoded polynucleotides, a vessel barcoded polynucleotide; a first complementary polynucleotide that is complementary to a first cell polynucleotide from the single cell, and a second complementary polynucleotide that is complementary to a second cell polynucleotide from the single cell; wherein the first complementary polynucleotide comprises a first molecular barcode of the plurality of molecular barcoded polynucleotides and the vessel barcode of the vessel barcoded polynucleotide or an amplified product of the vessel barcoded polynucleotide, and wherein the second complementary polynucleotide comprises a second molecular barcode of the plurality of molecular barcoded polynucleotides and the vessel barcode of the vessel barcoded polynucleotide or an amplified product of the vessel barcoded polynucleotide.

In one aspect, provided herein is a method comprising: (a) forming a plurality of vessels each comprising a single cell from a sample comprising a plurality of cells, a plurality of molecular barcoded polynucleotides, and a vessel barcoded polynucleotide; (b) producing: a first complementary polynucleotide that is complementary to a first cell polynucleotide from the single cell, and a second complementary polynucleotide that is complementary to a second cell polynucleotide from the single cell; (c) attaching: a first molecular barcoded polynucleotide of the plurality to the first complementary polynucleotide, and a second molecular barcoded polynucleotide to the second complementary polynucleotide, thereby forming a first and a second single cell single-barcoded polynucleotide; and (d) attaching the vessel barcoded polynucleotide, or an amplified product thereof to the first single cell single-barcoded polynucleotide or an amplified product thereof, and the second single cell single-barcoded polynucleotide or an amplified product thereof, thereby forming a first and a second single cell dual-barcoded sequences.

In one aspect, provided herein is a method comprising: (a) producing a first complementary polynucleotide from a heavy chain immunoglobulin (IgH) polynucleotide and a second complementary polynucleotide from a light chain immunoglobulin (IgL) polynucleotide from a plurality of immune cells from a sample with: a first target primer comprising a region complementary to a same region of the IgH polynucleotides from the plurality of immune cells; a second target primer comprising a region complementary to a same region of the IgL polynucleotides from the plurality of immune cells; a reverse transcriptase comprising a non-template terminal transferase activity, wherein 3 or more identical non-template nucleotides are added to the 3' end of the first and second complementary polynucleotides; a plurality of molecular barcoded polynucleotides, each comprising: a molecular barcode, a 5' end region complementary to a region of a vessel barcoded polynucleotide, and a 3' end region complementary to the 3 or more non-template nucleotides; and a vessel barcoded polynucleotide, thereby forming a first and a second single cell single-barcoded polynucleotide; (b) amplifying the vessel barcoded polynucleotide, thereby forming a first and a second single cell dual-barcoded polynucleotide; (c) amplifying the first and second single cell dual-barcoded polynucleotide, thereby forming a library of sequences comprising a variable region of the IgH or IgL polynucleotides, or a combination thereof; and (d) sequencing one or more of the sequences of the library, wherein (a) is performed in a vessel of a plurality of vessels, wherein the vessel comprises a single immune cell from the plurality of immune cells.

In one aspect, provided herein is a method comprising: (a) producing a first complementary polynucleotide from a T-cell receptor alpha (TCRα) polynucleotide and a second complementary polynucleotide from a T-cell receptor beta (TCRβ) polynucleotide from a plurality of immune cells from a sample with: a first target primer comprising a region complementary to a same region of the TCRα polynucleotides from the plurality of immune cells; a second target primer comprising a region complementary to a same region of the TCRβ polynucleotides from the plurality of immune cells; a reverse transcriptase comprising a non-template terminal transferase activity, wherein 3 or more identical non-template nucleotides are added to the 3' end of the first and second complementary polynucleotides; a plurality of molecular barcoded polynucleotides, each comprising: a molecular barcode, a 5' end region complementary to a region of a vessel barcoded polynucleotide, and a 3' end region complementary to the 3 or more non-template nucleotides; and a vessel barcoded polynucleotide, thereby forming a first and a second single cell single-barcoded polynucleotide; (b) amplifying the vessel barcoded polynucleotide, thereby forming a first and a second single cell dual-barcoded polynucleotide; (c) amplifying the first and second single cell dual-barcoded polynucleotide, thereby forming a library of sequences comprising a variable region of the TCRα or TCRβ polynucleotides, or a combination thereof; and (d) sequencing one or more of the sequences of the library, wherein (a) is performed in a vessel of a plurality of vessels, wherein the vessel comprises a single immune cell from the plurality of immune cells.

In one aspect, provided herein is a method comprising: (a) producing a first complementary polynucleotide from a T-cell receptor gamma (TCRγ) polynucleotide and a second complementary polynucleotide from a T-cell receptor delta (TCRδ) polynucleotide from a plurality of immune cells from a sample with: a first target primer comprising a region complementary to a same region of the TCRγ polynucleotides from the plurality of immune cells; a second target primer comprising a region complementary to a same region of the TCRδ polynucleotides from the plurality of immune cells; a reverse transcriptase comprising a non-template terminal transferase activity, wherein 3 or more identical non-template nucleotides are added to the 3' end of the first and second complementary polynucleotides; a plurality of molecular barcoded polynucleotides, each comprising: a molecular barcode, a 5' end region complementary to a region of a vessel barcoded polynucleotide, and a 3' end region complementary to the 3 or more non-template nucleotides; and a vessel barcoded polynucleotide, thereby forming a first and a second single cell single-barcoded polynucleotide; (b) amplifying the vessel barcoded polynucleotide, thereby forming a first and a second single cell dual-barcoded polynucleotide; (c) amplifying the first and second single cell dual-barcoded polynucleotide, thereby forming a library of sequences comprising a variable region of the TCRγ or TCRδ polynucleotides, or a combination thereof; and (d) sequencing one or more of the sequences of the library, wherein (a) is performed in a vessel of a plurality of vessels, wherein the vessel comprises a single immune cell from the plurality of immune cells.

In some embodiments, the library represents an immune state of the sample. In some embodiments, the first and second single cell dual-barcoded sequences are a library of first and second single cell dual-barcoded sequences. In some embodiments, the molecular barcode of the first and second molecular barcoded polynucleotides are different. In some embodiments, the first and second single cell single-barcoded polynucleotides comprise a different molecular barcode. In some embodiments, the first and second single cell dual-barcoded sequences comprise a different molecular barcode. In some embodiments, the first and second single cell dual-barcoded sequences comprise the same vessel barcode. In some embodiments, the plurality of molecular barcoded polynucleotides are not amplified products. In some embodiments, the molecular barcode of a molecular barcoded polynucleotide in a first vessel is different than the molecular barcode of a molecular barcoded polynucleotide in a second vessel. In some embodiments, the molecular barcode of each molecular barcoded polynucleotide in a first vessel of the plurality of vessels is unique. In some embodiments, the molecular barcode of each molecular barcoded polynucleotide in a second vessel of the plurality of vessels is unique. In some embodiments, the molecular barcode of each molecular barcoded polynucleotide in a first vessel and a second vessel are unique. In some embodiments, the molecular barcode of each molecular barcoded polynucleotide in a third vessel of the plurality of vessels is unique. In some embodiments, the molecular barcode of each molecular barcoded polynucleotide in the first vessel, the second vessel, and the third vessel are unique. In some embodiments, the molecular barcode of each molecular barcoded polynucleotide in any single vessel of the plurality of vessels is unique. In some embodiments, the molecular barcode of each molecular barcoded polynucleotide in any one vessel of the plurality of vessels is different than the molecular barcode of each molecular barcoded polynucleotide in any other one vessel of the plurality of vessels. In some embodiments, the molecular barcode of a molecular barcoded polynucleotide in a first vessel is the same as the molecular barcode of a molecular barcoded polynucleotide in a second vessel. In some embodiments, the molecular barcode of a molecular barcoded polynucleotide in a first vessel is the same as the molecular barcode of a molecular barcoded polynucleotide in the first vessel. In some embodiments, the molecular barcode of a molecular barcoded polynucleotide in a second vessel is the same as the molecular barcode of a molecular barcoded polynucleotide in the second vessel. In some embodiments, the vessel barcode of a vessel barcoded polynucleotide or amplicon thereof in a first vessel of the plurality of vessels is a different than the vessel barcode of a vessel barcoded polynucleotide or amplicon thereof in a second vessel of the plurality of vessels. In some embodiments, the vessel barcode of a vessel barcoded polynucleotide or amplicon thereof in a first vessel of the plurality of vessels is a first same vessel barcode. In some embodiments, the vessel barcode of each vessel barcoded polynucleotide or amplicon thereof in a second vessel of the plurality of vessels is a second same vessel barcode. In some embodiments, the first same vessel barcode is different than the second same vessel barcode. In some embodiments, the vessel barcode of each vessel barcoded polynucleotide or amplicon thereof in a single vessel of the plurality of vessels comprises a same vessel barcode. In some embodiments, the vessel barcode of each vessel barcoded polynucleotide and amplicon thereof in any single vessel of the plurality of vessels is unique to the vessel barcode of each vessel barcoded polynucleotide and amplicon thereof in any other single vessel of the plurality of vessels.

In some embodiments, the vessel barcoded polynucleotide in (a) is present in a vessel as a single molecule. In some embodiments, the vessel barcoded polynucleotide in (a) is present in each vessel of the plurality of vessels as a single molecule. In some embodiments, the vessel barcoded polynucleotide in (a) is present in a vessel of the plurality of vessels as at least a single molecule. In some embodiments, the vessel barcoded polynucleotide in (a) is present in each vessel of the plurality of vessels as at least a single molecule.

In some embodiments, a first common vessel sequence of a first vessel barcoded polynucleotide or amplicon thereof in a first vessel of the plurality of vessels is the same as a first common vessel sequence of a second vessel barcoded polynucleotide or amplicon thereof in the first vessel. In some embodiments, a second common vessel sequence of the first vessel barcoded polynucleotide or amplicon thereof in the first vessel of the plurality of vessels is the same as a second common vessel sequence of a second vessel barcoded polynucleotide or amplicon thereof in the first vessel. In some embodiments, a first common vessel sequence of a first vessel barcoded polynucleotide or amplicon thereof in any single vessel of the plurality of vessels is the same as a first common vessel sequence of a second vessel barcoded polynucleotide or amplicon thereof in the single vessel. In some embodiments, each vessel barcoded polynucleotide in a single vessel of the plurality of vessels comprises a same first common vessel sequence. In some embodiments, each vessel barcoded polynucleotide in a single vessel of the plurality of vessels comprises a same second common vessel sequence. In some embodiments, a first common vessel sequence of a first vessel barcoded polynucleotide or amplicon thereof in a first vessel of the plurality of vessels is the same as a first common vessel sequence of a second vessel barcoded polynucleotide or amplicon thereof in a second vessel of the plurality of vessels. In some embodiments, a second common vessel sequence of the first vessel barcoded polynucleotide or amplicon thereof is the same as a second common vessel sequence of the second vessel barcoded polynucleotide or amplicon thereof. In some embodiments, each vessel barcoded polynucleotide or amplicon thereof in any one vessel of the plurality of vessels comprises a first common vessel sequence comprising the same sequence as a first common vessel sequence of a vessel barcoded polynucleotide or amplicon thereof in any other one vessel of the plurality of vessels. In some embodiments, each vessel barcoded polynucleotide or amplicon thereof in any one vessel of the plurality of vessels comprises a second common vessel sequence comprising the same sequence as a second common vessel sequence of a vessel barcoded polynucleotide or amplicon thereof in any other one vessel of the plurality of vessels. In some embodiments, a first common molecular sequence of a first molecular barcoded polynucleotide in a first vessel of the plurality of vessels is the same as a first common molecular sequence of a second molecular barcoded polynucleotide in the first vessel. In some embodiments, a second common molecular sequence of the first molecular barcoded polynucleotide in the first vessel of the plurality of vessels is the same as a second common molecular sequence of a second molecular barcoded polynucleotide in the first vessel. In some embodiments, a first common molecular sequence of a first molecular barcoded polynucleotide in any single vessel of the plurality of vessels is the same as a first common molecular sequence of a second molecular barcoded polynucleotide in the single vessel. In some embodiments, each molecular barcoded polynucleotide in a single vessel of the plurality of vessels comprises a same first common molecular sequence. In some embodiments, each molecular barcoded polynucleotide in a single vessel of the plurality of vessels comprises a same second common molecular sequence. In some embodiments, a first common molecular sequence of a first molecular barcoded polynucleotide in a first vessel of the plurality of vessels is the same as a first common molecular sequence of a second molecular barcoded polynucleotide in a second vessel of the plurality of vessels. In some embodiments, a second common molecular sequence of the first molecular barcoded polynucleotide is the same as a second common molecular sequence of the second molecular barcoded polynucleotide. In some embodiments, each molecular barcoded polynucleotide in any one vessel of the plurality of vessels comprises a first common molecular sequence comprising the same sequence as a first common molecular sequence of a molecular barcoded polynucleotide in any other one vessel of the plurality of vessels. In some embodiments, each molecular barcoded polynucleotide in any one vessel of the plurality of vessels comprises a second common molecular sequence comprising the same sequence as a second common molecular sequence of a molecular barcoded polynucleotide in any other one vessel of the plurality of vessels. In some embodiments, the first common vessel sequence comprises a sequence comprising the same sequence as the first common molecular sequence. In some embodiments, the first common vessel sequence comprises a sequence complementary to the first common molecular sequence or a compliment thereof. In some embodiments, the second common molecular sequence comprises a region complementary to three or more non-template nucleotides added to the 3' end of the first complementary polynucleotide. In some embodiments, the region complementary to three or more non-template nucleotides added to the 3' end of the first complementary polynucleotide is a terminal region.

In some embodiments, a first and a second molecular barcoded polynucleotide are not fused together. In some embodiments, the first and second single cell single-barcoded polynucleotides are not fused together. In some embodiments, the first and second single cell dual-barcoded sequences are not fused together.

In some embodiments, the first cell polynucleotide is DNA. In some embodiments, the second cell polynucleotide is DNA. In some embodiments, the first cell polynucleotide is RNA. In some embodiments, the second cell polynucleotide is RNA. In some embodiments, the RNA is mRNA. In some embodiments, the first complementary polynucleotide of (b) is cDNA. In some embodiments, the second complementary polynucleotide of (b) is cDNA.

In some embodiments, (b) comprises extending a first target primer hybridized to the first cell polynucleotide, and extending a second target primer hybridized to the second cell polynucleotide. In some embodiments, the extending comprises reverse transcribing the first cell polynucleotide with a first target primer, and reverse transcribing the second cell polynucleotide with a second target primer. In some embodiments, the first target primer comprises a sequence complementary to a target sequence of the first cell polynucleotide. In some embodiments, the second target primer comprises a sequence complementary to a target sequence of the second cell polynucleotide. In some embodiments, the first target primer comprises a poly (T) sequence. In some embodiments, the second target primer comprises a poly (T) sequence. In some embodiments, the target sequence of the first cell polynucleotide is a heavy chain immunoglobulin (IgH) sequence, a TCRα sequence, a TCRγ sequence, or a combination thereof. In some embodiments, the target sequence of the first cell polynucleotide is a heavy chain constant region ($C_H$) sequence, a TCRα constant region (Cα) sequence, a TCRγ constant region (Cγ) sequence, or a combination thereof. In some embodiments, the target sequence of the second cell polynucleotide is a light chain immunoglobulin (IgL) sequence, a TCRβ sequence, a TCRδ sequence, or a combination thereof. In some embodiments, the target sequence of the second cell polynucleotide is a light chain constant region ($C_L$) sequence, a TCRβ constant region (Cβ) sequence, a TCRδ constant region (Cδ) sequence, or a combination thereof. In some embodiments, the first target primer comprises a plurality of first target primers. In some embodiments, the second target primer comprises a plurality of second target primers. In some embodiments, the plurality of first target primers comprises a plurality of sequences complementary to a plurality of heavy chain immunoglobulin (IgH) sequences, TCRα sequences, TCRγ sequences, or a combination thereof. In some embodiments, the plurality of heavy chain immunoglobulin (IgH) sequences, TCRα sequences or TCRγ sequences comprises a plurality of heavy chain constant region ($C_H$) sequences, TCRα constant region (Cα) sequences, TCRγ constant region (Cγ) sequences, or a combination thereof. In some embodiments, the plurality of heavy chain constant region ($C_H$) sequences comprises two or more sequences selected from the group consisting of heavy chain constant region ($C_H$) sequences from IgM, IgD, IgA, IgE, IgG, and combinations thereof. In some embodiments, the plurality of second target primers comprises a plurality of sequences complementary to a plurality of light chain immunoglobulin (IgL) sequences, TCRβ sequences, TCRδ sequences, or a combination thereof. In some embodiments, the plurality of light chain immunoglobulin (IgL) o sequences, TCRβ sequences or TCRδ sequences comprises a plurality of light chain constant region ($C_L$) sequences, TCRβ constant region (Cβ) sequences, TCRδ constant regions (Cδ) sequences, or a combination thereof. In some embodiments, the plurality of light chain constant region ($C_L$) sequences comprises two or more sequences selected from the group consisting of light chain constant region ($C_L$) sequences from Igκ, Igλ, and combinations thereof. In some embodiments, in (b) the extending comprises use of a non-template terminal transferase, wherein three or more non-template nucleotides are added to the 3' end of the first complementary polynucleotide. In some embodiments, the non-template terminal transferase is a reverse transcriptase or a polymerase. In some embodiments, the non-template terminal transferase is a reverse transcriptase, and wherein the reverse transcriptase is selected from the group consisting of Superscript II reverse transcriptase, Maxima reverse transcriptase, Protoscript II reverse transcriptase, moloney murine leukemia virus reverse transcriptase (MMLV-RT), HighScriber reverse transcriptase, avian myeloblastosis virus (AMV) reverse transcriptase, any reverse transcriptase comprising terminal deoxynucleotidyl transferase activity, and combinations thereof. In some embodiments, three or more non-template nucleotides are added to the 3' end of the second complementary polynucleotide.

In some embodiments, in (c) the attaching comprises hybridizing a region of a first molecular barcoded polynucleotide to the three or more non-template nucleotides added to the 3' end of the first complementary polynucleotide. In some embodiments, in (c) the attaching comprises hybridizing a region of a second molecular barcoded polynucleotide to the three or more non-template nucleotides added to the 3' end of the second complementary polynucleotide. In some embodiments, in (c) a first molecular barcoded polynucleotide attached to the first complementary polynucleotide comprises a region complementary to the three or more non-template nucleotides on the 3' end of the first complementary polynucleotide. In some embodiments, in (c) a second molecular barcoded polynucleotides attached to the second complementary polynucleotide comprises a region complementary to three or more non-template nucleotides on the 3' end of the second complementary polynucleotide. In some embodiments, the three or more non-template nucleotides are identical. In some embodiments, at least one of the three or more non-template nucleotides is not identical to another nucleotide of the three or more non-template nucleotides. In some embodiments, at least one nucleotide of the hybridized region of the first molecular barcoded polynucleotide is not identical to another nucleic acid of the hybridized region of the first molecular barcoded polynucleotide. In some embodiments, at least one nucleotide of the hybridized region of the second molecular barcoded polynucleotide is not identical to another nucleic acid of the hybridized region of the second molecular barcoded polynucleotide. In some embodiments, the at least one non-identical nucleotide is a deoxyribonucleotide or analog thereof. In some embodiments, the at least one non-identical nucleotide is not a ribonucleotide or analog thereof. In some embodiments, the at least one non-identical nucleotide is a deoxyriboguanosine. In some embodiments, the at least one non-identical nucleotide is a deoxyriboguanosine analog. In some embodiments, the at least one non-identical nucleotide is a terminal nucleotide of the first or second molecular barcoded polynucleotide. In some embodiments, the at least one non-identical nucleotide is a ribonucleotide or analog thereof. In some embodiments, a terminal nucleotide of the hybridized region of the first or second molecular barcoded polynucleotide is a deoxyribonucleotide or analog thereof. In some embodiments, a terminal nucleotide of the hybridized region of the first or second molecular barcoded polynucleotide is not a ribonucleotide or analog thereof. In some embodiments, a terminal nucleotide of the hybridized region of the first or second molecular barcoded polynucleotide is a deoxyriboguanosine. In some embodiments, a terminal nucleotide of the hybridized region of the first or second molecular barcoded polynucleotide is a deoxyriboguanosine analog. In some embodiments, a terminal nucleotide of the hybridized region of the first or second molecular barcoded polynucleotide is a ribonucleotide or analog thereof. In some embodiments, at least two non-terminal nucleotides of the hybridized region of the first or second molecular barcoded polynucleotide are ribonucleotides or analogs thereof. In some embodiments, at least two non-terminal nucleotides of the hybridized region of the first or second molecular barcoded polynucleotide are not deoxyribonucleotides or analogs thereof. In some embodiments, at least two non-terminal nucleotides of the hybridized region of the first or second molecular barcoded polynucleotide are deoxyribonucleotides or analogs thereof. In some embodiments, (c) further comprises extending the first complementary polynucleotide and the second complementary polynucleotide after the attaching. In some embodiments, the first complementary polynucleotide comprises a region complementary to a first molecular barcoded polynucleotide. In some embodiments, the second complementary polynucleotide comprises a region complementary to a second molecular barcoded polynucleotide. In some embodiments, the first complementary polynucleotide comprises a region complementary to a second molecular barcoded polynucleotide. In some embodiments, the region of the first complementary polynucleotide that is complementary to the first or second molecular barcoded polynucleotide is not complementary to a molecular barcode sequence In some embodiments, the region of the first complementary polynucleotide that is complementary to the first or second molecular barcoded polynucleotide is not complementary to a region of the vessel barcoded polynucleotide or an amplified product therefrom. In some embodiments, the region of the first complementary polynucleotide complementary to the first or second molecular barcoded polynucleotide comprises three or more non-template nucleotides added to the 3' end of the first complementary polynucleotide. In some embodiments, the region of the second complementary polynucleotide that is complementary to the second molecular barcoded polynucleotide comprises three or more non-template nucleotides added to the 3' end of the second complementary polynucleotide. In some embodiments, the first complementary polynucleotide is not complementary to the vessel barcoded polynucleotide. In some embodiments, the second complementary polynucleotide is not complementary to the vessel barcoded polynucleotide. In some embodiments, a region of a complement of a first molecular barcoded polynucleotide is complementary to a region of the vessel barcoded polynucleotide. In some embodiments, a region of a complement of a second molecular barcoded polynucleotide is complementary to a region of the vessel barcoded polynucleotide. In some embodiments, a region of the first single cell single-barcoded polynucleotide is complementary to a region of the vessel barcoded polynucleotide. In some embodiments, a region of the second single cell single-barcoded polynucleotide is complementary to a region of the vessel barcoded polynucleotide. In some embodiments, a region of the first single cell single-barcoded polynucleotide is complementary to the region of the vessel barcoded polynucleotide to which the second single cell single-barcoded polynucleotide is complementary. In some embodiments, the method further comprises amplifying the vessel barcoded polynucleotide with a first primer set, wherein the amplifying is performed before attaching the vessel barcoded polynucleotide or simultaneously with attaching the vessel barcoded polynucleotide. In some embodiments, the vessel barcoded polynucleotide comprises a first and a second vessel barcoded polynucleotide selected from the group consisting of the vessel barcoded polynucleotide, a complement of the vessel barcoded polynucleotide thereof, an amplified product from the vessel barcoded polynucleotide, and any combination thereof. In some embodiments, attaching the vessel barcoded polynucleotide comprises: hybridizing a region of the vessel barcoded polynucleotide or amplified product thereof to a region of the first single cell single-barcoded polynucleotide, and hybridizing a region of the vessel barcoded polynucleotide or amplified product thereof to a region of the second single cell single-barcoded polynucleotide.

In some embodiments, the method further comprises extending the first single cell single-barcoded sequence and the second single cell single-barcoded sequence polynucleotide after attaching the vessel barcoded polynucleotide, thereby forming the first and second single cell dual-barcoded sequences. In some embodiments, the first single cell dual-barcoded sequence comprises a region complementary to the vessel barcoded polynucleotide. In some embodiments, the second single cell dual-barcoded sequence comprises a region complementary to the vessel barcoded polynucleotide. In some embodiments, the regions of the first and second single cell dual-barcoded sequences that are complementary to the vessel barcoded polynucleotide are the same sequence. In some embodiments, the region of the first single cell single-barcoded polynucleotide that is complementary to the first or second molecular barcoded polynucleotide is not complementary to a region of the vessel barcoded polynucleotide or an amplified product therefrom. In some embodiments, a first primer of the first primer set is complementary to a region of a first molecular barcoded polynucleotide, a complement of the first single cell single-barcoded polynucleotide, a complement of the first single cell dual-barcoded sequence, or any combination thereof. In some embodiments, the first primer of the first primer set is complementary to a region of a second molecular barcoded polynucleotide, a complement of the second single cell single-barcoded polynucleotide, a complement of the second single cell dual-barcoded sequence, or any combination thereof. In some embodiments, a first primer of the first primer set is not complementary to the first cell polynucleotide or a complement thereof. In some embodiments, the first primer of the first primer set is not complementary to the second cell polynucleotide or a complement thereof. In some embodiments, a first primer of the first primer set is complementary to a region of a complement of the first single cell single-barcoded sequence that is downstream of the molecular barcode. In some embodiments, the first thereof of the first primer set is complementary to a region of a complement of the second single cell single-barcoded polynucleotide that is downstream of the molecular barcode. In some embodiments, a first primer of the first primer set is complementary to a region of a complement of the first single cell dual-barcoded sequence that is upstream of the vessel barcode. In some embodiments, the first primer of the first primer set is complementary to a region of a complement of the second single cell dual-barcoded polynucleotide that is upstream of the vessel barcode. In some embodiments, a second primer of the first primer set is not complementary to a region of the first cell polynucleotide or a complement thereof, the first complementary polynucleotide or a complement thereof, a first molecular barcoded polynucleotide or complement thereof, the first single cell single-barcoded polynucleotide or complement thereof, or any combination thereof. In some embodiments, the second primer of the first primer set is not complementary to a region of the second cell polynucleotide or a complement thereof, the second complementary polynucleotide or a complement thereof, a second molecular barcoded polynucleotide or complement thereof, the second single cell single-barcoded polynucleotide or complement thereof, or any combination thereof. In some embodiments, a second primer of the first primer set is complementary to a region of the first single cell dual-barcoded sequence. In some embodiments, a second primer of the first primer set is complementary to a region of the second single cell dual-barcoded sequence. In some embodiments, a second primer of the first primer set is complementary to a region of the first single cell dual-barcoded sequence that is upstream of the molecular barcode. In some embodiments, the second primer of the first primer set is complementary to a region of the second molecular barcoded polynucleotide that is upstream of the molecular barcode. In some embodiments, a second thereof of the first primer set is complementary to a region of the first single cell dual-barcoded sequence that is upstream of the vessel barcode. In some embodiments, the second thereof of the first primer set is complementary to a region of the second molecular barcoded polynucleotide that is upstream of the vessel barcode.

In some embodiments, the method further comprises breaking two or more vessels of the plurality of vessels. In some embodiments, the method further comprises pooling the first and second single cell dual-barcoded sequences from the two or more broken vessels.

In some embodiments, the method further comprises amplifying the first and second single cell dual-barcoded sequences. In some embodiments, the amplifying the first and second single cell dual-barcoded sequences is performed outside of a vessel of the plurality of vessels. In some embodiments, the method further comprise amplifying the first and second single cell dual-barcoded sequences with a second primer set. In some embodiments, a first primer of the second primer set is not complementary to a region of the first cell polynucleotide or a complement thereof, the first complementary polynucleotide or a complement thereof, a first molecular barcoded polynucleotide or complement thereof, the first single cell single-barcoded polynucleotide or complement thereof, or any combination thereof. In some embodiments, the first primer of the second primer set is not complementary to a region of the second cell polynucleotide or a complement thereof, the second complementary polynucleotide or a complement thereof, a second molecular barcoded polynucleotide or complement thereof, the second single cell single-barcoded polynucleotide or complement thereof, or any combination thereof. In some embodiments, a first primer of the second primer set is complementary to a region of the first single cell dual-barcoded sequence. In some embodiments, the first primer of the second primer set is complementary to a region of the second single cell dual-barcoded sequence. In some embodiments, a first primer of the second primer set is complementary to a region of the first single cell dual-barcoded sequence that is upstream of the molecular barcode. In some embodiments, the first primer of the second primer set is complementary to a region of the second single cell dual-barcoded sequence that is upstream of the molecular barcode. In some embodiments, a first primer of the second primer set is complementary to a region of the first single cell dual-barcoded sequence that is upstream of the vessel barcode. In some embodiments, the first primer of the second primer set is complementary to a region of the second single cell dual-barcoded sequence that is upstream of the vessel barcode. In some embodiments, the second primer of the first primer set is the first primer of the second primer set. In some embodiments, a second primer of the second primer set is complementary to a region of the first and second cell polynucleotide, a complement of the first and second complementary polynucleotide, a complement of the first and second single cell single-barcoded polynucleotide, a complement of the first and second single cell dual-barcoded sequence, or any combination thereof. In some embodiments, the second primer of the second primer set comprises a poly (T) sequence. In some embodiments, a second primer of the second primer set is complementary to a region of the first or second cell polynucleotide, a complement of the first or second complementary polynucleotide, a complement of the first or second single cell single-barcoded polynucleotide, a complement of the first or second single cell dual-barcoded sequence, or any combination thereof. In some embodiments, the second primer of the second primer set is not complementary to a first or second molecular barcoded polynucleotide or complement thereof, the vessel barcoded polynucleotide or complement thereof, or any combination thereof. In some embodiments, a third primer of the second primer set is complementary to a region of the second cell polynucleotide, a complement of the second complementary polynucleotide, a complement of the second single cell single-barcoded polynucleotide, a complement of the second single cell dual-barcoded sequence, or any combination thereof. In some embodiments, the second primer of the second primer set is complementary to a region of the first cell polynucleotide, a complement of the first complementary polynucleotide, a complement of the first single cell single-barcoded polynucleotide, a complement of the first single cell dual-barcoded sequence, or any combination thereof. In some embodiments, the third primer of the second primer set is not complementary to a region of the first cell polynucleotide, a complement of the first complementary polynucleotide, a complement of the first single cell single-barcoded polynucleotide, a complement of the first single cell dual-barcoded sequence, or any combination thereof. In some embodiments, the third primer of the second primer set is not complementary to a first or second molecular barcoded polynucleotide or complement thereof, the vessel barcoded polynucleotide or complement thereof, or any combination thereof. In some embodiments, the second primer of the second primer set comprises a target specific sequence. In some embodiments, the third primer of the second primer set comprises a target specific sequence. In some embodiments, the target specific sequence of the second primer of the second primer set targets a heavy chain immunoglobulin (IgH) sequence, TCRα sequence, TCRγ sequence, or a combination thereof. In some embodiments, the target specific sequence of the second primer of the second primer set targets a heavy chain constant region sequence ($C_H$), TCRα constant region (Ca) sequence, TCRγ constant region (Cγ) sequence, or a combination thereof. In some embodiments, the target specific sequence of the second primer is selected from the group consisting of GGGTTGGGGCGGATGCAC (SEQ ID NO: 1), CATCCG-GAGCCTTGGTGG (SEQ ID NO: 2), CCTTGGGGCTG-GTCGGGG (SEQ ID NO: 3), CGGATGGGCTCTGT-GTGG (SEQ ID NO: 4), CCGATGGGCCCTTGGTGG (SEQ ID NO: 5), GGATTTAGAGTCTCTCAGCTG (SEQ ID NO: 6), CACGGCAGGGTCAGGGTTC (SEQ ID NO: 7) and GGGGAAACATCTGCATCAAGT (SEQ ID NO: 8). In some embodiments, the target specific sequence of the third primer of the second primer set targets a light chain immunoglobulin (IgL) sequence, TCRβ sequence, TCR sequence, or a combination thereof. In some embodiments, the target specific sequence of the third primer of the second primer set targets a light chain constant region sequence (CL), a TCRβ constant region (Cβ) sequence, a TCR constant region (Cδ) sequence, or a combination thereof. In some embodiments, the target specific sequence of the third primer is selected from the group consisting of TTT-GATCTCCACCTTGGTCCCTCCGC (SEQ ID NO: 9), TTTGATCTCCAGCTTGGTCCCCTGG (SEQ ID NO: 10), TTTGATATCCACTTTGGTCCCAGGGC (SEQ ID NO: 11), TTTGATTTCCACCTTGGTCCCTTGGC (SEQ ID NO: 12), TTTAATCTCCAGTCGTGTCCCTTGGC (SEQ ID NO: 13), GAGGACGGTCACCTTGGTGCCA (SEQ ID NO: 14), TAGGACGGTCAGCTTGGTCCCTCC (SEQ ID NO: 15), GAGGACGGTCAGCTGGGTGCC (SEQ ID NO: 16), TAAAATGATCAGCTGGGTTCCTCCAC (SEQ ID NO: 17), TAGGACGGTGACCTTGGTCCCAG (SEQ ID NO: 18), GGGAGATCTCTGCTTCTGATG (SEQ ID NO: 19), CGACCTCGGGTGGGAACAC (SEQ ID NO: 20) and CGGATGGTTTGGTATGAGGC (SEQ ID NO: 21). In some embodiments, the second primer of the second primer set comprises a plurality of second primers. In some embodiments, the third primer of the second primer set comprises a plurality of third primers. In some embodiments, the target specific sequences of the plurality of second primers target a plurality of heavy chain immunoglobulin (IgH) sequences, TCRα sequences, TCRγ sequences, or a combination thereof. In some embodiments, the plurality of heavy chain immunoglobulin (IgH) sequences, TCRα sequences, or TCRγ sequences comprises a plurality of heavy chain constant region ($C_H$), TCRα constant region (Cα) sequences, TCRγ constant region (Cγ) sequences, or a combination thereof. In some embodiments, the plurality of heavy chain constant region ($C_H$) sequences comprises two or more sequence selected from the group consisting of heavy chain constant region ($C_H$) sequences from IgM, IgD, IgA, IgE, IgG, and combinations thereof. In some embodiments, the target specific sequences of the plurality of third primers target a plurality of light chain immunoglobulin (IgL) sequences, TCRβ sequences, TCRδ sequences, or a combination thereof. In some embodiments, the plurality of light chain immunoglobulin (IgL) sequences, TCRβ sequences, or TCRδ sequences, comprises a plurality of light chain constant region ($C_L$) sequences, TCRβ constant region (Cβ) sequences, TCRδ constant region (Cδ) sequences, or a combination thereof. In some embodiments, the plurality of light chain constant region ($C_L$) sequences comprises two or more sequence selected from the group consisting of light chain constant region ($C_L$) sequences from Igκ, Igλ, and combinations thereof.

In some embodiments, a first target primer, a second target primer, the vessel barcoded polynucleotide, a molecular barcoded polynucleotide, or any combination thereof is not attached to a solid support. In some embodiments, a first target primer, a second target primer, a primer of the first primer set, a primer of the second primer set, or any combination thereof, does not comprise a molecular barcode, a vessel barcode, a barcode, or any combination thereof. In some embodiments, a first target primer, a second target primer, a primer of the first primer set, a primer of the second primer set, or any combination thereof, does not comprise an overhang region. In some embodiments, each vessel of the plurality of vessels does not comprise a solid support. In some embodiments, the vessel barcoded polynucleotide is attached to a solid support. In some embodiments, the vessel barcoded polynucleotide is attached to a bead. In some embodiments, the vessel barcoded polynucleotide, a molecular barcoded polynucleotide, or any combination thereof is not a primer. In some embodiments, the vessel barcoded polynucleotide, a molecular barcoded polynucleotide, or any combination thereof is not extended.

In some embodiments, (a)-(d) are performed in the single vessel.

In some embodiments, (a)-(d) are performed in a single reaction.

In some embodiments, the method further comprises lysing the single cell. In some embodiments, the lysing releases the first and second cell polynucleotide from the single cell. In some embodiments, the single cell is lysed after (a). In some embodiments, the single cell is lysed before (b). In some embodiments, the single cell is lysed in the vessel. In some embodiments, the lysing comprises chemical lysing. In some embodiments, the lysing comprises freeze-thawing.

In some embodiments, the vessel barcode is amplified before (d). In some embodiments, the vessel barcode is amplified simultaneously with (d). In some embodiments, the vessel barcode and the first single cell barcoded polynucleotide is amplified or extended simultaneously. In some embodiments, the vessel barcode, the first single cell single-barcoded polynucleotide and the second single cell single-barcoded polynucleotide are amplified or extended simultaneously. In some embodiments, the first single cell barcoded polynucleotide and the second single cell single-barcoded polynucleotide are amplified or extended simultaneously. In some embodiments, the first single cell dual-barcoded polynucleotide and the second single cell dual-barcoded polynucleotide are amplified or extended simultaneously. In some embodiments, the plurality of vessels comprises a plurality of wells. In some embodiments, the plurality of vessels comprises a plurality of emulsions. In some embodiments, each emulsion of the plurality of emulsions is from about 0.01 picoliters to 10 microliters in volume. In some embodiments, the plurality of vessels comprises a plurality of containers. In some embodiments, the first target primer, second target primer, a primer of the first primer set, or a primer of the second primer set comprises a sample barcode. In some embodiments, the method further comprises recovering the first single cell dual-barcoded polynucleotide, the second single cell dual-barcoded polynucleotide, and amplified products thereof from the vessel. In some embodiments, the method further comprises sequencing the first single cell dual-barcoded polynucleotide, the second single cell dual-barcoded polynucleotide, amplified products thereof, or any combination thereof. In some embodiments, the first single cell dual-barcoded polynucleotide, the second single cell dual-barcoded polynucleotide, amplified products thereof, or any combination thereof are sequenced simultaneously. In some embodiments, the first single cell dual-barcoded polynucleotide, the second single cell dual-barcoded polynucleotide, amplified products thereof, or any combination thereof are sequenced in the same reaction.

In some embodiments, the method further comprises determining the cell origin of the first cell polynucleotide and the second cell polynucleotide to be the same based on the vessel barcode. In some embodiments, the determining comprises matching the sequence of the vessel barcode of the first single cell dual-barcoded polynucleotide or amplified product thereof to the sequence of the vessel barcode of the second single cell dual-barcoded polynucleotide or amplified product thereof. In some embodiments, the method further comprises determining a number of starting molecules with a sequence of the first cell polynucleotide, the second cell polynucleotide, or both, based on the molecular barcode. In some embodiments, the determining comprises determining the number of sequences with a same first molecular barcode, a same second molecular barcode, or both. In some embodiments, when a first sequence of a single cell dual-barcoded polynucleotide or amplified product thereof and a second sequence of a single cell dual-barcoded polynucleotide or amplified product thereof contain a same vessel barcode or complement thereof, they are from the same single vessel or single cell. In some embodiments, when the first sequence of a single cell dual-barcoded polynucleotide or amplified product thereof and the second sequence of a single cell dual-barcoded polynucleotide or amplified product thereof contain a different molecular barcode or complement thereof, they are from a different cell polynucleotide molecule. In some embodiments, when the first sequence of a single cell dual-barcoded polynucleotide or amplified product thereof and the second sequence of a single cell dual-barcoded polynucleotide or amplified product thereof contain a same molecular barcode or complement thereof, they are from a same cell polynucleotide molecule. In some embodiments, when the first sequence of a single cell dual-barcoded polynucleotide or amplified product thereof and the second sequence of a single cell dual-barcoded polynucleotide or amplified product thereof contain a different vessel barcode or complement thereof, they are from a different single vessel or single cell.

In some embodiments, the single cell comprises an immune cell. In some embodiments, the plurality of cells comprises a plurality of immune cells. In some embodiments, the immune cell is a lymphocyte or subtype thereof, a B-cell or subtype thereof, a T-cell or subtype thereof, or a combination thereof. In some embodiments, the plurality of cells is enriched for memory B-cells, naive B-cells, plasmablast B-cells, naive T-cells, plasmablast T-cells, any sub-type of B-cell, any sub-type of T-cell, or any combination thereof. In some embodiments, the single cell comprises a cancer cell. In some embodiments, the plurality of cells comprises a plurality of cancer cells. In some embodiments, the cancer cell is a squamous cell carcinoma cell, an adenocarcinoma cell, a transitional cell carcinoma cell, a bone sarcoma cell, a cartilage sarcoma cell, a muscle sarcoma cell, a leukemia cell, a lymphoma cell, a glioma cell, or any combination thereof. In some embodiments, the plurality of cancer cells is enriched for circulating cancer cells, endothelial cancer cells, epithelial cancer cells, rare cancer cells, or any type or subtype of cancer cell. In some embodiments, the sample is a biological sample. In some embodiments, the biological sample is from a subject. In some embodiments, the method further comprises diagnosing the subject as having a disease or condition. In some embodiments, the subject is an animal. In some embodiments, the animal is a human. In some embodiments, the method further comprises determining whether a subject is homozygous or heterozygous for an allele. In some embodiments, the method further comprises diagnosing, prognosing, or treating a subject with a disease or condition. In some embodiments, the sample is a blood sample. In some embodiments, the first or second cell polynucleotide is isolated from the sample. In some embodiments, the first or second cell polynucleotide is not isolated from the sample.

In some embodiments, the sample comprises a plurality of samples comprising a first sample and a second sample. In some embodiments, the plurality of samples comprises at least 3, 4, 5, 10, 20, 30, 40, 50, 60, 70, 80, 90 or 100 or more samples. In some embodiments, the plurality of samples comprises at least about 100, 200, 300, 400, 500, 600, 700, 800, 900 or 1000 or more samples. In some embodiments, the plurality of samples comprises at least about 1000, 2000, 3000, 4000, 5000, 6000, 7000, 8000 samples, 9000, or 10,000 samples, or 100,000 samples, or 1,000,000 or more samples. In some embodiments, the plurality of samples comprises at least about 10,000 samples. In some embodiments, the first sample is from a first subject and the second sample is from a second subject. In some embodiments, the first subject is a subject with a disease or condition. In some embodiments, the second subject is a subject without a disease or condition. In some embodiments, the first or second cell polynucleotide comprises a variant sequence. In some embodiments, the variant sequence comprises a mutation, polymorphism, deletion, or insertion. In some embodiments, the polymorphism is a single nucleotide polymorphism. In some embodiments, the first or second cell polynucleotide is a biomarker for a disease or condition. In some embodiments, the first or second cell polynucleotide is from a pathogen. In some embodiments, the pathogen is a virus, bacteria, or fungus.

In some embodiments, the method further comprises comparing the sequences of a library of the first and second single cell dual-barcoded polynucleotides from a subject to a library of the first and second single cell dual-barcoded polynucleotides from the same subject at a different time point. In some embodiments, the method further comprises comparing the sequences of a library of the first and second single cell dual-barcoded polynucleotides from a subject with a disease or condition to a library of the first and second single cell dual-barcoded polynucleotides from a subject without the disease or condition.

In some embodiments, the method further comprises determining a germ line sequence of the first cell polynucleotide, the second cell polynucleotide, or both wherein the first cell polynucleotide comprises an IgH or $V_H$ sequence, and wherein the second cell polynucleotide comprises an IgL or $V_L$ sequence, or any combination thereof. In some embodiments, the method further comprises determining a variance of the sequence of the IgL IgH, $V_H$, $V_L$, or any combination thereof from a sequence of those of the germ line. In some embodiments, the method further comprises determining at least one of: the total number of unique IgH sequences; the total number of unique IgL sequences; the total number of unique IgH and IgL sequences; the total number of unique paired IgL and IgH sequences; the frequency of an IgH sequence, or an IgL sequence; or the frequency of a combination of an IgH sequence and an IgL sequence against one or more others. In some embodiments, the method further comprises determining a germ line sequence of the first cell polynucleotide, the second cell polynucleotide, or both wherein the first cell polynucleotide comprises a TCRα or Vα sequence, and wherein the second cell polynucleotide comprises TCRβ or Vβ sequence, or any combination thereof. In some embodiments, the method further comprises determining a variance of the sequence of the TCRα, TCRβ, Vα, Vβ, or any combination thereof from a sequence of those of the germ line. In some embodiments, the method further comprises determining at least one of: the total number of unique TCRα, sequences; the total number of unique TCRβ sequences; the total number of unique TCRα, and TCRβ sequences; the total number of unique paired TCRβ and TCRα, sequences; the frequency of a TCRα sequence, or a TCRβ sequence; or the frequency of a combination of a TCRα sequence and a TCRβ sequence against one or more others. In some embodiments, the method further comprises determining a germ line sequence of the first cell polynucleotide, the second cell polynucleotide, or both wherein the first cell polynucleotide comprises a TCRγ or V sequence, and wherein the second cell polynucleotide comprises TCRδ or Vδ sequence, or any combination thereof. In some embodiments, the method further comprises determining a variance of the sequence of the TCRγ, TCRδ, Vγ, Vδ, or any combination thereof from a sequence of those of the germ line. In some embodiments, the method further comprises determining at least one of: the total number of unique TCRγ, sequences; the total number of unique TCRδ sequences; the total number of unique TCRγ, and TCRδ sequences; the total number of unique paired TCRδ and TCRγ, sequences; the frequency of a TCRγ sequence, or a TCRδ sequence; or the frequency of a combination of a TCRγ sequence and a TCRδ sequence against one or more others. In some embodiments, the method further comprises determining at least one of: the total number of sequences from a first gene; the total number of sequences from a second gene; the total number of unique sequences from a first gene; the total number of unique sequences from a second gene; or the frequency of a sequence from a first gene, or a sequence from a second gene. In some embodiments, the method further comprises selecting an antibody or TCR based on a total quantity of one or more pairs of individually paired IgL and IgH sequences, or TCRα and TCRβ sequences, or TCRγ and TCRδ sequences, and a variance from a germ line. In some embodiments, the method further comprises selecting an antibody or TCR based on one or more IgL or IgH sequences, TCRα and TCRβ sequences, or TCRγ and TCRδ sequences, and a variance from a germ line. In some embodiments, the method further comprises selecting an antibody or TCR based on one or more of sequence patterns, variance analysis, dynamics, or frequency. In some embodiments, the method further comprises selecting an antibody or TCR based on frequency.

In some embodiments, the selected antibody or TCR binds to an epitope with a KD of less than about or equal to $1\times10^{-7}$, $1\times10^{-8}$, $1\times10^{-9}$, $1\times10^{-10}$, $1\times10^{-11}$, or $1\times10^{-12}$M.

In some embodiments, the selected antibody or TCR is a human therapeutic antibody or TCR. In some embodiments, the selected antibody or TCR is a neutralizing antibody or TCR. In some embodiments, a target to which the selected antibody or TCR binds is unknown. In some embodiments, a target to which the selected antibody or TCR binds is unknown at the time the selected antibody or TCR is selected.

In some embodiments, the method further comprises contacting the selected antibody or TCR with at least one biomarker candidate to discover a biomarker. In some embodiments, the biomarker candidate is on a solid support. In some embodiments, the biomarker is in solution. In some embodiments, the antibody or TCR is on a solid support. In some embodiments, the antibody or TCR is in solution. In some embodiments, the solid support is an array. In some embodiments, the solid support is a bead.

In some embodiments, the method further comprises inserting the first cell polynucleotide into a vector. In some embodiments, the method further comprises inserting the second cell polynucleotide into the vector. In some embodiments, the vector is a cloning vector. In some embodiments, the vector is an expression vector.

In some embodiments, the method further comprises matching sequences with identical molecular barcodes. In some embodiments, the method further comprises forming consensus sequences from the library. In some embodiments, sequencing and PCR errors are minimized, eliminated, or less than 0.01%, 0.001%, 0.0001%, 0.00001%, 0.000001%, or 0.0000001%. In some embodiments, the number of cycles in an amplification reaction is limited to any of 1-40 cycles.

In one aspect, provided herein is an isolated, purified, antibody or TCR identified by any of the methods described herein. In one aspect, provided herein is an isolated, purified, antibody IgL, TCRβ, or TCRδ identified by any of the methods described herein. In one aspect, provided herein is an isolated, purified, antibody IgH, TCRα or TCRγ by any of the methods described herein. In one aspect, provided herein is an isolated, purified, Fab fragment of an antibody or TCR identified by any of the methods described herein. In one aspect, provided herein is an isolated, purified, Fab2 fragment of an antibody or TCR identified by any of the methods described herein. In one aspect, provided herein is an isolated, purified, Fv fragment of an antibody or TCR identified by any of the methods described herein. In one aspect, provided herein is an isolated, purified, ScFv fragment of an antibody identified by any of the methods described herein. In one aspect, provided herein is a method of treating a subject in need thereof, comprising administering the selected antibody or TCR, or a fragment thereof, to a subject in need thereof. In some embodiments, the antibody, TCR or fragment thereof is identified from the subject in need thereof. In some embodiments, the antibody, TCR or fragment thereof is not identified from the subject in need thereof. In some embodiments, the subject in need thereof displays one or more symptoms of a disease. In some embodiments, the subject in need thereof has a disease. In some embodiments, the disease is unknown. In some embodiments, the disease is known. In some embodiments, the sample comprises a first sample from a subject taken at a first time point and a second sample from the subject taken at a second time point. In some embodiments, the method further comprises determining an increase or decrease in quantity of the first or second cell polynucleotide from the samples taken at the first and second time points. In some embodiments, the increase or decrease in quantity is an increase or decrease ranging from at least about: 0.1 fold, 0.2, fold, 0.3 fold, 0.4, fold, 0.5 fold, 0.6 fold, 0.7 fold, 0.8 fold, 0.9 fold, 1.5 fold, 2 fold, 3 fold, 5 fold, 10 fold, 50 fold, 100 fold, 1,000 fold, 10,000 fold, 100,000 fold, 1,000,000 fold, or more. In some embodiments, the time between the first and second time points is about, or at least about: 1 hour, 2 hours, 3 hours, 4 hours, 5 hours, 6 hours 7 hour, 8 hours, 9 hours, 10 hours, 11 hours, 12 hours 13 hour, 14 hours, 15 hours, 16 hours, 17 hours, 18 hours, 19 hour, 20 hours, 21 hours, 22 hours, 23 hours, 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In some embodiments, the sequencing is high-throughput. In some embodiments, the method does not comprise a multiplex of primers and/or a multiplex of primers attached to a solid support. In some embodiments, the method does not employ a multiplicity of V-segment primers comprising a sequence that is complementary to a single functional V segment or a small family of V segments. In some embodiments, the method does not employ a step of isolating the first or second cell polynucleotide. In some embodiments, the sequencing is done by massive parallel synthesis.

In some embodiments, the method further comprises comparing the sequence reads to a germ line sequence and determining a somatic hypermutation accumulation of the sequence reads. In some embodiments, the method further comprises determining an isotype distribution of antibody sequences to select a specific isotype. In some embodiments, selected antibody comprises a specific Ig isotype. In some embodiments, the Ig isotype is IgA, IgG, IgM, IgD, or IgE.

In some embodiments, the method further comprises generating a library of paired IgH and IgL antibody sequences or TCRα and TCRβ sequences. In some embodiments, the library is a database. In some embodiments, the first and second single cell dual-barcoded polynucleotides comprise a CDR1, CDR2, CDR3, and/or hypermutation region across antibody or TCR coding sequences.

In some embodiments, the method further comprises cloning the selected antibody or TCR directly into surface-display technology. In some embodiments, the method further comprises evolving the selected antibody or TCR by directed evolution. In some embodiments, the method further comprises screening the selected antibody or TCR for functional specificity, affinity, or neutralization ability. In some embodiments, somatic mutations are determined with 99% confidence or higher. In some embodiments, each V, D, and J segment from each polynucleotide molecule is identified.

In some embodiments, the vessel barcode comprises at least 2 nucleotides. In some embodiments, the vessel barcode comprises at least 3, 4, 5, 6, 7, 8, or 9 nucleotides In some embodiments, the vessel barcode comprises at least 10 nucleotides. In some embodiments, the vessel barcode comprises at least 15 nucleotides. In some embodiments, the vessel barcode comprises at most 50 nucleotides. In some embodiments, the vessel barcode comprises from 10-30 nucleotides. In some embodiments, the vessel barcode comprises a degenerate sequence. In some embodiments, the vessel barcode comprises a full or partial degenerate sequence. In some embodiments, the vessel barcode comprises the sequence NNNNNNNNNNNNNNN, wherein N is any nucleic acid. In some embodiments, the vessel barcode comprises the sequence NNNNNWNNNNNWNNNNN, wherein N is any nucleic acid and W is adenine or thymine. In some embodiments, the vessel barcode comprises the sequence NNNNNXNNNNNXNNNNN, wherein N is any nucleic acid and X is any known nucleotide. In some embodiments, the vessel barcode comprises the sequence NNNNNNNNNNNNNNNNN, wherein N is any nucleic acid and at least one or two N in the sequence is W, wherein W is adenine or thymine. In some embodiments, the vessel barcode comprises the sequence NNNNNNNNNNNNNNNNN, wherein N is any nucleic acid and at least one or two N in the sequence is X, wherein X is any known nucleotide. In some embodiments, the molecular barcode comprises at least 2 nucleotides. In some embodiments, the molecular barcode comprises at least 3, 4, 5, 6, 7, 8, or 9 nucleotides. In some embodiments, the molecular barcode comprises at least 10 nucleotides. In some embodiments, the molecular barcode comprises at least 15 nucleotides. In some embodiments, the molecular barcode comprises at most 50 nucleotides. In some embodiments, the molecular barcode comprises from 10-30 nucleotides. In some embodiments, the molecular barcode comprises a degenerate sequence. In some embodiments, the molecular barcode comprises a full or partial degenerate sequence. In some embodiments, the molecular barcode comprises the sequence NNNNNNNN, wherein N is any nucleic acid. In some embodiments, the molecular barcode comprises the sequence NNTNNANN, wherein N is any nucleic acid. In some embodiments, the molecular barcode comprises the sequence NNWNNWNN, wherein N is any nucleic acid and W is adenine or thymine. In some embodiments, the molecular barcode comprises the sequence NNXNNXNN, wherein N is any nucleic acid and X is any known nucleotide. In some embodiments, the molecular barcode comprises the sequence NNNNNNNN, wherein N is any nucleic acid and at least one or two N in the sequence is W, wherein W is adenine or thymine. In some embodiments, the molecular barcode comprises the sequence NNNNNNNN, wherein N is any nucleic acid and at least one or two N in the sequence is X, wherein X is any known nucleotide.

In some embodiments, the method further comprises correcting amplification errors. In some embodiments, the method further comprises correcting sequencing errors. In some embodiments, the method further comprises binning or grouping sequences comprising the same molecular barcode. In some embodiments, the method further comprises binning or grouping sequences comprising the same molecular barcode using a computer or algorithm. In some embodiments, the method further comprises binning or grouping sequences comprising the same vessel barcode using a computer or algorithm. In some embodiments, the method further comprises clustering sequences with at least about 90%, 95%, or 99% sequence homology. In some embodiments, the method further comprises aligning sequences with at least about 90%, 95%, or 99% sequence homology. In some embodiments, the clustering or aligning is performed with the aid of a computer or algorithm. In some embodiments, the method comprises determining the number of sequence reads containing the same molecular barcode. In some embodiments, the method comprises determining the number of sequence reads containing both the same molecular barcode and a same first cell polynucleotide sequence with at least about 90%, 95%, or 99% sequence homology. In some embodiments, the method comprises determining the number of sequence reads containing both the same molecular barcode and a same second cell polynucleotide sequence with at least about 90%, 95%, or 99% sequence homology. In some embodiments, the method comprises determining the amount of a first or second cell polynucleotide in the sample. In some embodiments, the method comprises forming a consensus sequence from two or more sequences, sequence reads, amplicon sequences, binned sequences, aligned sequences, clustered sequences, or amplicon set sequences comprising the same molecular barcode or vessel barcode, or both. In some embodiments, the method comprises determining a first or second cell polynucleotide sequence with at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 99.99%, or 100% accuracy or confidence. In some embodiments, sequencing and PCR errors are minimized, eliminated, or less than 0.01%, 0.001%, 0.0001%, 0.00001%, 0.000001%, or 0.0000001%. In some embodiments, the error rate of sequencing is less than or equal to 0.00001%, 0.0001%, 0.001%, 0.01%, or 0%. In some embodiments, the error rate of sequencing is not 0. In some embodiments, at least 1000, 100000, $1\times10^6$, $1\times10^7$, $1\times10^8$, $1\times10^9$, $1\times10^{10}$, $1\times10^{11}$, $1\times10^{12}$, or $9\times10^{12}$ polynucleotides are sequenced. In some embodiments, the method is performed in a positive amount of time less than or equal to 4 weeks, 3 weeks, 2 weeks, 1 week, 6 days, 5 days, 5 days, 4 days, 3 days, 2 days, 1 day, 18 hours, 12 hours, 9 hours, 6 hours, 3 hours, 2 hours, or 1 hour. In some embodiments, the number of reads used to achieve a particular confidence or base calling accuracy is at least about 1.1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 30, 40, 50, 60, 70, 80, 90, 100, 200, 300, 400, 500, 600, 700, 800, 900, or 1000 fold fewer than the number of reads used to achieve the same, similar, or higher confidence or base calling accuracy using a similar method without the use of molecular barcodes, vessel barcodes, or both. In some embodiments, the number of reads used to achieve a particular confidence or base calling accuracy is at least about 1000, 100000, $1\times10^6$, $1\times10^7$, $1\times10^8$, $1\times10^9$, $1\times10^{10}$, $1\times10^{11}$, $1\times10^{12}$, or $9\times10^{12}$ reads fewer than the number of reads used to achieve the same, similar, or higher confidence or base calling accuracy using a similar method without the use of molecular barcodes, vessel barcodes, or both. In some embodiments, the plurality of vessels comprises at least 1000, 100000, $1\times10^6$, $1\times10^7$, $1\times10^8$, $1\times10^9$, $1\times10^{10}$, $1\times10^{11}$, $1\times10^{12}$, or $9\times10^{12}$ or more vessels. In some embodiments, the plurality of cell polynucleotides comprises at least 1000, 100000, $1\times10^6$, $1\times10^7$, $1\times10^8$, $1\times10^9$, $1\times10^{10}$, $1\times10^{11}$, $1\times10^{12}$, or $9\times10^{12}$ or more cell polynucleotides.

In one aspect, provided herein is a composition comprising: a plurality of vessels each comprising a single cell from a sample comprising a plurality of cells, a plurality of molecular barcoded polynucleotides, a vessel barcoded polynucleotide; a first complementary polynucleotide that is complementary to a first cell polynucleotide from the single cell, and a second complementary polynucleotide that is complementary to a second cell polynucleotide from the single cell; wherein the first complementary polynucleotide comprises a first molecular barcode of the plurality of molecular barcoded polynucleotides and the vessel barcode of the vessel barcoded polynucleotide or an amplified product of the vessel barcoded polynucleotide, and wherein the second complementary polynucleotide comprises a second molecular barcode of the plurality of molecular barcoded polynucleotides and the vessel barcode of the vessel barcoded polynucleotide or an amplified product of the vessel barcoded polynucleotide.

In some embodiments, the molecular barcode of the first and second molecular barcoded polynucleotides are different. In some embodiments, the first and second complementary polynucleotides comprise a different molecular barcode. In some embodiments, the first and second complementary polynucleotides comprise the same vessel barcode. In some embodiments, the plurality of molecular barcoded polynucleotides are not amplified products. In some embodiments, the molecular barcode of a molecular barcoded polynucleotide in a first vessel is different than the molecular barcode of a molecular barcoded polynucleotide in a second vessel. In some embodiments, the molecular barcode of each molecular barcoded polynucleotide in a first vessel of the plurality of vessels is unique. In some embodiments, the molecular barcode of each molecular barcoded polynucleotide in a second vessel of the plurality of vessels is unique. In some embodiments, the molecular barcode of each molecular barcoded polynucleotide in a first vessel and a second vessel are unique. In some embodiments, the molecular barcode of each molecular barcoded polynucleotide in a third vessel of the plurality of vessels is unique. In some embodiments, the molecular barcode of each molecular barcoded polynucleotide in the first vessel, the second vessel, and the third vessel are unique. In some embodiments, the molecular barcode of each molecular barcoded polynucleotide in any single vessel of the plurality of vessels is unique. In some embodiments, the molecular barcode of each molecular barcoded polynucleotide in any one vessel of the plurality of vessels is different than the molecular barcode of each molecular barcoded polynucleotide in any other one vessel of the plurality of vessels. In some embodiments, the molecular barcode of a molecular barcoded polynucleotide in a first vessel is the same as the molecular barcode of a molecular barcoded polynucleotide in a second vessel. In some embodiments, the molecular barcode of a molecular barcoded polynucleotide in a first vessel is the same as the molecular barcode of a molecular barcoded polynucleotide in the first vessel. In some embodiments, the molecular barcode of a molecular barcoded polynucleotide in a second vessel is the same as the molecular barcode of a molecular barcoded polynucleotide in the second vessel. In some embodiments, the vessel barcode of a vessel barcoded polynucleotide or amplicon thereof in a first vessel of the plurality of vessels is a different than the vessel barcode of a vessel barcoded polynucleotide or amplicon thereof in a second vessel of the plurality of vessels. In some embodiments, the vessel barcode of a vessel barcoded polynucleotide or amplicon thereof in a first vessel of the plurality of vessels is a first same vessel barcode. In some embodiments, the vessel barcode of each vessel barcoded polynucleotide or amplicon thereof in a second vessel of the plurality of vessels is a second same vessel barcode. In some embodiments, the first same vessel barcode is different than the second same vessel barcode. In some embodiments, the vessel barcode of each vessel barcoded polynucleotide or amplicon thereof in a single vessel of the plurality of vessels comprises a same vessel barcode. In some embodiments, the vessel barcode of each vessel barcoded polynucleotide and amplicon thereof in any single vessel of the plurality of vessels is unique to the vessel barcode of each vessel barcoded polynucleotide and amplicon thereof in any other single vessel of the plurality of vessels. In some embodiments, the vessel barcoded polynucleotide is present in a vessel as a single molecule. In some embodiments, the vessel barcoded polynucleotide is present in each vessel of the plurality of vessels as a single molecule. In some embodiments, the vessel barcoded polynucleotide is present in a vessel of the plurality of vessels as at least a single molecule. In some embodiments, the vessel barcoded polynucleotide is present in each vessel of the plurality of vessels as at least a single molecule. In some embodiments, a first common vessel sequence of a first vessel barcoded polynucleotide or amplicon thereof in a first vessel of the plurality of vessels is the same as a first common vessel sequence of a second vessel barcoded polynucleotide or amplicon thereof in the first vessel. In some embodiments, a second common vessel sequence of the first vessel barcoded polynucleotide or amplicon thereof in the first vessel of the plurality of vessels is the same as a second common vessel sequence of a second vessel barcoded polynucleotide or amplicon thereof in the first vessel. In some embodiments, a first common vessel sequence of a first vessel barcoded polynucleotide or amplicon thereof in any single vessel of the plurality of vessels is the same as a first common vessel sequence of a second vessel barcoded polynucleotide or amplicon thereof in the single vessel. In some embodiments, each vessel barcoded polynucleotide in a single vessel of the plurality of vessels comprises a same first common vessel sequence. In some embodiments, each vessel barcoded polynucleotide in a single vessel of the plurality of vessels comprises a same second common vessel sequence. In some embodiments, a first common vessel sequence of a first vessel barcoded polynucleotide or amplicon thereof in a first vessel of the plurality of vessels is the same as a first common vessel sequence of a second vessel barcoded polynucleotide or amplicon thereof in a second vessel of the plurality of vessels. In some embodiments, a second common vessel sequence of the first vessel barcoded polynucleotide or amplicon thereof is the same as a second common vessel sequence of the second vessel barcoded polynucleotide or amplicon thereof. In some embodiments, each vessel barcoded polynucleotide or amplicon thereof in any one vessel of the plurality of vessels comprises a first common vessel sequence comprising the same sequence as a first common vessel sequence of a vessel barcoded polynucleotide or amplicon thereof in any other one vessel of the plurality of vessels. In some embodiments, each vessel barcoded polynucleotide or amplicon thereof in any one vessel of the plurality of vessels comprises a second common vessel sequence comprising the same sequence as a second common vessel sequence of a vessel barcoded polynucleotide or amplicon thereof in any other one vessel of the plurality of vessels. In some embodiments, a first common molecular sequence of a first molecular barcoded polynucleotide in a first vessel of the plurality of vessels is the same as a first common molecular sequence of a second molecular barcoded polynucleotide in the first vessel. In some embodiments, a second common molecular sequence of the first molecular barcoded polynucleotide in the first vessel of the plurality of vessels is the same as a second common molecular sequence of a second molecular barcoded polynucleotide in the first vessel. In some embodiments, a first common molecular sequence of a first molecular barcoded polynucleotide in any single vessel of the plurality of vessels is the same as a first common molecular sequence of a second molecular barcoded polynucleotide in the single vessel. In some embodiments, each molecular barcoded polynucleotide in a single vessel of the plurality of vessels comprises a same first common molecular sequence. In some embodiments, each molecular barcoded polynucleotide in a single vessel of the plurality of vessels comprises a same second common molecular sequence. In some embodiments, a first common molecular sequence of a first molecular barcoded polynucleotide in a first vessel of the plurality of vessels is the same as a first common molecular sequence of a second molecular barcoded polynucleotide in a second vessel of the plurality of vessels. In some embodiments, a second common molecular sequence of the first molecular barcoded polynucleotide is the same as a second common molecular sequence of the second molecular barcoded polynucleotide. In some embodiments, each molecular barcoded polynucleotide in any one vessel of the plurality of vessels comprises a first common molecular sequence comprising the same sequence as a first common molecular sequence of a molecular barcoded polynucleotide in any other one vessel of the plurality of vessels. In some embodiments, each molecular barcoded polynucleotide in any one vessel of the plurality of vessels comprises a second common molecular sequence comprising the same sequence as a second common molecular sequence of a molecular barcoded polynucleotide in any other one vessel of the plurality of vessels. In some embodiments, the first common vessel sequence comprises a sequence comprising the same sequence as the first common molecular sequence. In some embodiments, the first common vessel sequence comprises a sequence complementary to the first common molecular sequence or a compliment thereof. In some embodiments, the second common molecular sequence comprises a region complementary to three or more non-template nucleotides added to the 3' end of the first complementary polynucleotide. In some embodiments, the region complementary to three or more non-template nucleotides added to the 3' end of the first complementary polynucleotide is a terminal region.

In some embodiments, a first and a second molecular barcoded polynucleotide are not fused together. In some embodiments, the first and second complementary polynucleotides are not fused together.

In some embodiments, the first cell polynucleotide is DNA. In some embodiments, the second cell polynucleotide is DNA. In some embodiments, the first cell polynucleotide is RNA. In some embodiments, the second cell polynucleotide is RNA. In some embodiments, the RNA is mRNA. In some embodiments, the first complementary polynucleotide is cDNA. In some embodiments, the second complementary polynucleotide is cDNA.

In some embodiments, the composition further comprises a non-template terminal transferase, a reverse transcriptase, a polymerase, or any combination thereof. In some embodiments, the first and/or second complimentary polynucleotides comprise three or more non-template nucleotides added to the 3' end. In some embodiments, the non-template terminal transferase is a reverse transcriptase, and wherein the reverse transcriptase is selected from the group consisting of Superscript II reverse transcriptase, Maxima reverse transcriptase, Protoscript II reverse transcriptase, moloney murine leukemia virus reverse transcriptase (MMLV-RT), HighScriber reverse transcriptase, avian myeloblastosis virus (AMV) reverse transcriptase, any reverse transcriptase comprising terminal deoxynucleotidyl transferase activity, and combinations thereof. In some embodiments, a first molecular barcoded polynucleotide comprises a region complementary to the three or more non-template nucleotides on the 3' end of the first complementary polynucleotide. In some embodiments, second molecular barcoded polynucleotides comprise a region complementary to three or more non-template nucleotides on the 3' end of the second complementary polynucleotide. In some embodiments, the three or more non-template nucleotides are identical. In some embodiments, at least one of the three or more non-template nucleotides is not identical to another nucleotide of the three or more non-template nucleotides. In some embodiments, at least one nucleotide of the complementary region of the first molecular barcoded polynucleotide is not identical to another nucleic acid of the complementary region of the first molecular barcoded polynucleotide. In some embodiments, at least one nucleotide of the complementary region of the second molecular barcoded polynucleotide is not identical to another nucleic acid of the complementary region of the second molecular barcoded polynucleotide. In some embodiments, the at least one non-identical nucleotide is a deoxyribonucleotide or analog thereof. In some embodiments, the at least one non-identical nucleotide is not a ribonucleotide or analog thereof. In some embodiments, the at least one non-identical nucleotide is a deoxyriboguanosine. In some embodiments, the at least one non-identical nucleotide is a deoxyriboguanosine analog. In some embodiments, the at least one non-identical nucleotide is a terminal nucleotide of the first or second molecular barcoded polynucleotide. In some embodiments, the at least one non-identical nucleotide is a ribonucleotide or analog thereof. In some embodiments, a terminal nucleotide of the complementary region of the first or second molecular barcoded polynucleotide is a deoxyribonucleotide or analog thereof. In some embodiments, a terminal nucleotide of the hybridized region of the first or second molecular barcoded polynucleotide is not a ribonucleotide or analog thereof. In some embodiments, a terminal nucleotide of the hybridized region of the first or second molecular barcoded polynucleotide is a deoxyriboguanosine. In some embodiments, a terminal nucleotide of the hybridized region of the first or second molecular barcoded polynucleotide is a deoxyriboguanosine analog. In some embodiments, a terminal nucleotide of the hybridized region of the first or second molecular barcoded polynucleotide is a ribonucleotide or analog thereof. In some embodiments, at least two non-terminal nucleotides of the hybridized region of the first or second molecular barcoded polynucleotide are ribonucleotides or analogs thereof. In some embodiments, at least two non-terminal nucleotides of the hybridized region of the first or second molecular barcoded polynucleotide are not deoxyribonucleotides or analogs thereof. In some embodiments, at least two non-terminal nucleotides of the hybridized region of the first or second molecular barcoded polynucleotide are deoxyribonucleotides or analogs thereof. In some embodiments, the first complementary polynucleotide comprises a region complementary to a first molecular barcoded polynucleotide. In some embodiments, the second complementary polynucleotide comprises a region complementary to a second molecular barcoded polynucleotide. In some embodiments, the first complementary polynucleotide comprises a region complementary to a second molecular barcoded polynucleotide. In some embodiments, the region of the first complementary polynucleotide that is complementary to the first or second molecular barcoded polynucleotide is not complementary to a molecular barcode sequence. In some embodiments, the region of the first complementary polynucleotide that is complementary to the first or second molecular barcoded polynucleotide is not complementary to a region of the vessel barcoded polynucleotide or an amplified product therefrom. In some embodiments, the region of the first complementary polynucleotide complementary to the first or second molecular barcoded polynucleotide comprises three or more non-template nucleotides added to the 3' end of the first complementary polynucleotide. In some embodiments, the region of the second complementary polynucleotide that is complementary to the second molecular barcoded polynucleotide comprises three or more non-template nucleotides added to the 3' end of the second complementary polynucleotide. In some embodiments, the first complementary polynucleotide is not complementary to the vessel barcoded polynucleotide. In some embodiments, the second complementary polynucleotide is not complementary to the vessel barcoded polynucleotide. In some embodiments, a region of a complement of a first molecular barcoded polynucleotide is complementary to a region of the vessel barcoded polynucleotide. In some embodiments, a region of a complement of a second molecular barcoded polynucleotide is complementary to a region of the vessel barcoded polynucleotide. In some embodiments, the composition further comprises any one or more primers from the methods above. In some embodiments, each vessel of the plurality of vessels does not comprise a solid support. In some embodiments, the vessel barcoded polynucleotide is attached to a solid support. In some embodiments, the vessel barcoded polynucleotide is attached to a bead. In some embodiments, the vessel barcoded polynucleotide, a molecular barcoded polynucleotide, or any combination thereof is not a primer. In some embodiments, the vessel barcoded polynucleotide, a molecular barcoded polynucleotide, or any combination thereof is not an extended polynucleotide. In some embodiments, the cell is lysed. In some embodiments, the plurality of vessels comprises a plurality of wells. In some embodiments, the plurality of vessels comprises a plurality of emulsions. In some embodiments, each emulsion of the plurality of emulsions is from about 0.01 picoliters to 10 microliters in volume.

In some embodiments, the single cell comprises an immune cell. In some embodiments, the plurality of cells comprises a plurality of immune cells. In some embodiments, the immune cell is a lymphocyte or subtype thereof, a B-cell or subtype thereof, a T-cell or subtype thereof, or a combination thereof. In some embodiments, the plurality of cells is enriched for memory B-cells, naive B-cells, plasmablast B-cells, naive T-cells, plasmablast T-cells, any subtype of B-cell, any sub-type of T-cell, or any combination thereof. In some embodiments, the single cell comprises a cancer cell. In some embodiments, the plurality of cells comprises a plurality of cancer cells. In some embodiments, the cancer cell is a squamous cell carcinoma cell, an adenocarcinoma cell, a transitional cell carcinoma cell, a bone sarcoma cell, a cartilage sarcoma cell, a muscle sarcoma cell, a leukemia cell, a lymphoma cell, a glioma cell, or any combination thereof. In some embodiments, the plurality of cancer cells is enriched for circulating cancer cells, endothelial cancer cells, epithelial cancer cells, rare cancer cells, or any type or subtype of cancer cell. In some embodiments, the first or second cell polynucleotide comprises a variant sequence. In some embodiments, the variant sequence comprises a mutation, polymorphism, deletion, or insertion. In some embodiments, the polymorphism is a single nucleotide polymorphism. In some embodiments, the first or second cell polynucleotide is a biomarker for a disease or condition. In some embodiments, the first or second cell polynucleotide is from a pathogen. In some embodiments, the first and second complementary polynucleotides comprise a CDR1, CDR2, CDR3, and/or hypermutation region across antibody or TCR coding sequences.

In some embodiments, the vessel barcode comprises at least 2 nucleotides. In some embodiments, the vessel barcode comprises at least 3, 4, 5, 6, 7, 8, or 9 nucleotides. In some embodiments, the vessel barcode comprises at least 10 nucleotides. In some embodiments, the vessel barcode comprises at least 15 nucleotides. In some embodiments, the vessel barcode comprises at most 50 nucleotides. In some embodiments, the vessel barcode comprises from 10-30 nucleotides. In some embodiments, the vessel barcode comprises a degenerate sequence. In some embodiments, the vessel barcode comprises a full or partial degenerate sequence. In some embodiments, the vessel barcode comprises the sequence NNNNNNNNNNNNNNNN, wherein N is any nucleic acid. In some embodiments, the vessel barcode comprises the sequence NNNNNWNNNNNWNNNNN, wherein N is any nucleic acid and W is adenine or thymine. In some embodiments, the vessel barcode comprises the sequence NNNNNXNNNNNXNNNNN, wherein N is any nucleic acid and X is any known nucleotide. In some embodiments, the vessel barcode comprises the sequence NNNNNNNNNNNNNNNNN, wherein N is any nucleic acid and at least one or two N in the sequence is W, wherein W is adenine or thymine. In some embodiments, the vessel barcode comprises the sequence NNNNNNNNNNNNNNNNN, wherein N is any nucleic acid and at least one or two N in the sequence is X, wherein X is any known nucleotide. In some embodiments, the molecular barcode comprises at least 2 nucleotides. In some embodiments, the molecular barcode comprises at least 3, 4, 5, 6, 7, 8, or 9 nucleotides. In some embodiments, the molecular barcode comprises at least 10 nucleotides. In some embodiments, the molecular barcode comprises at least 15 nucleotides. In some embodiments, the molecular barcode comprises at most 50 nucleotides. In some embodiments, the molecular barcode comprises from 10-30 nucleotides. In some embodiments, the molecular barcode comprises a degenerate sequence. In some embodiments, the molecular barcode comprises a full or partial degenerate sequence. In some embodiments, the molecular barcode comprises the sequence NNNNNNNN, wherein N is any nucleic acid. In some embodiments, the molecular barcode comprises the sequence NNTNNANN, wherein N is any nucleic acid. In some embodiments, the molecular barcode comprises the sequence NNWNNWNN, wherein N is any nucleic acid and W is adenine or thymine. In some embodiments, the molecular barcode comprises the sequence NNX-NNXNN, wherein N is any nucleic acid and X is any known nucleotide. In some embodiments, the molecular barcode comprises the sequence NNNNNNNN, wherein N is any nucleic acid and at least one or two N in the sequence is W, wherein W is adenine or thymine. In some embodiments, the molecular barcode comprises the sequence NNNNNNNN, wherein N is any nucleic acid and at least one or two N in the sequence is X, wherein X is any known nucleotide.

In some embodiments, the plurality of vessels comprises at least 1000, 100000, $1 \times 10^6$, $1 \times 10^7$, $1 \times 10^8$, $1 \times 10^9$, $1 \times 10^{10}$, $1 \times 10^{11}$, $1 \times 10^{12}$, or $9 \times 10^{12}$ or more vessels. In some embodiments, the plurality of cell polynucleotides comprises at least 1000, 100000, $1 \times 10^6$, $1 \times 10^7$, $1 \times 10^8$, $1 \times 10^9$, $1 \times 10^{10}$, $1 \times 10^{11}$, $1 \times 10^{12}$, or $9 \times 10^{12}$ or more cell polynucleotides.

In one aspect, provided herein is a method of barcoding polynucleotides comprising (a) hybridizing a molecular barcoded polynucleotide to each of a plurality of polynucleotides from a single cell, wherein the hybridized molecular barcoded polynucleotide is from a plurality of uniquely molecular barcoded polynucleotides within a vessel comprising the single cell; (b) extending a polynucleotide from the single cell that is hybridized to a molecular barcoded polynucleotide to form a molecular barcoded cell polynucleotide; (c) hybridizing a vessel barcoded polynucleotide to a molecular barcoded cell polynucleotide, wherein the vessel barcoded polynucleotide is unique to a single vessel of a plurality of vessels; (d) extending a molecular barcoded cell polynucleotide that is hybridized to a vessel barcoded polynucleotide to form a dual-barcoded cell polynucleotide; and (e) sequencing the dual-barcoded cell polynucleotide. In some embodiments, the hybridization in (a) is not through basepairing of a naturally occurring sequence on the polynucleotides from a single cell. In some embodiments, the vessel barcoded polynucleotide hybridized to the molecular barcoded cell polynucleotide is an amplified product. In some embodiments, the hybridization in (c) is not through basepairing of a compliment of a naturally occurring sequence on the polynucleotides from a single cell. In some embodiments, the hybridization in (c) is through basepairing to a region of the polynucleotide from the single cell that was extended in (b). In some embodiments, (a)-(d) are performed in the single vessel. In some embodiments, (a)-(d) are performed in a single reaction.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference. For example, all publications and patents mentioned herein are incorporated herein by reference in their entirety for the purpose of describing and disclosing the kits, compositions, and methodologies that are described in the publications, which might be used in connection with the methods, kits, and compositions described herein. The documents discussed herein are provided solely for their disclosure prior to the filing date of the present application. Nothing herein is to be construed as an admission that the inventors described herein are not entitled to antedate such disclosure by virtue of prior invention or for any other reason.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

DETAILED DESCRIPTION

Figure 1A:
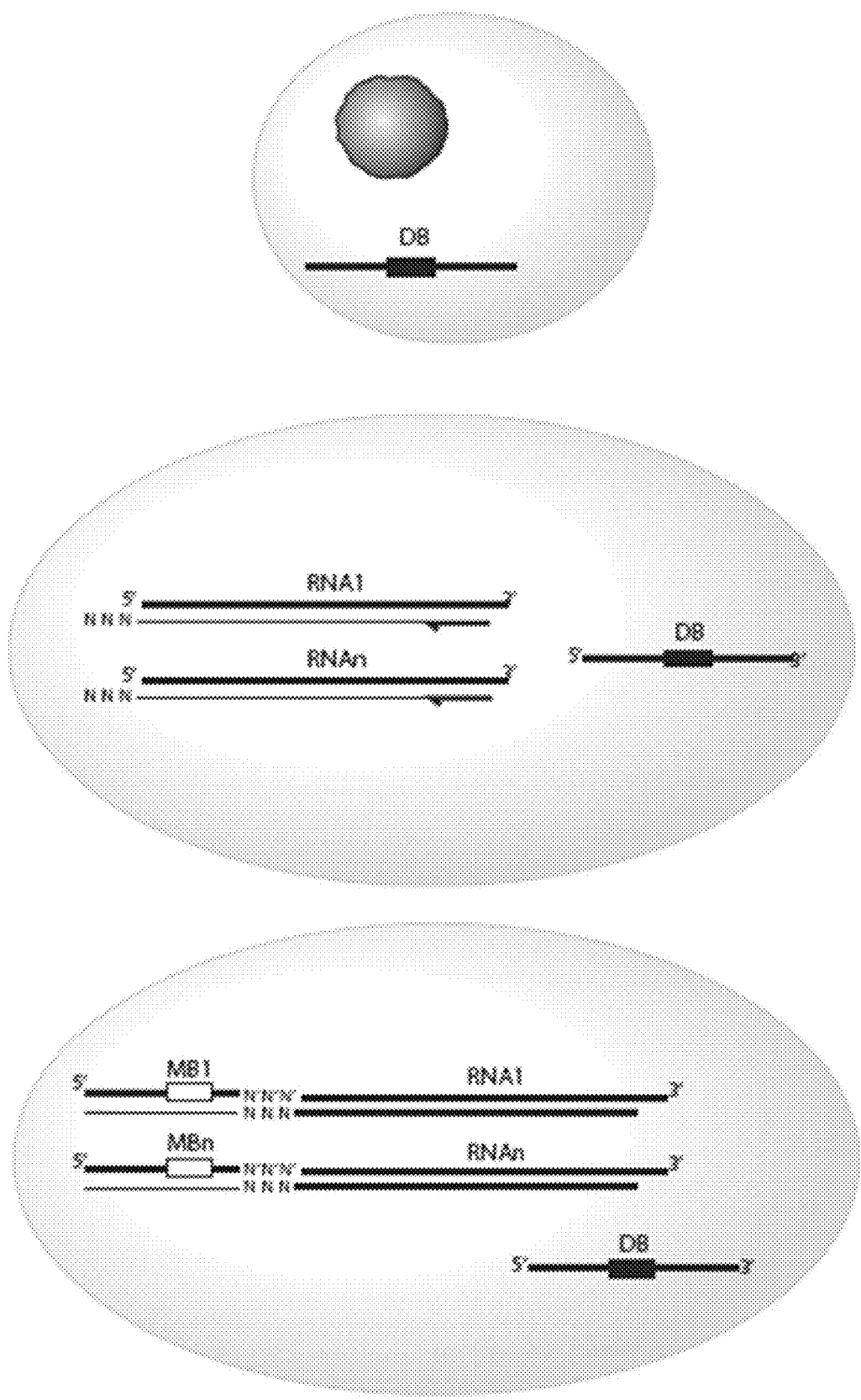
FIG. 1A depicts a schematic of a barcoding phase an exemplary method described herein. The sketch represents a method of amplifying and barcoding two or more polynucleotides, such as paired variable Ig (e.g., $V_H$ and $V_L$ mRNAs) and TCRδ sequences (e.g., Vα/Vβ and Vγ/Vδ mRNAs), such as for library preparation and immune sequencing. Vessel Barcode (DB); Molecular Barcode (MB). (Top) A single droplet (of a plurality of droplets) in an emulsion containing a single cell and other reaction components (e.g., enzymes, buffers, oligonucleotides). (Middle) Cell lysis and reverse transcription of lysed cell RNAs. (Bottom) Molecular Barcode (MB) tagging of single molecules during reverse transcription.
Figure 1B:
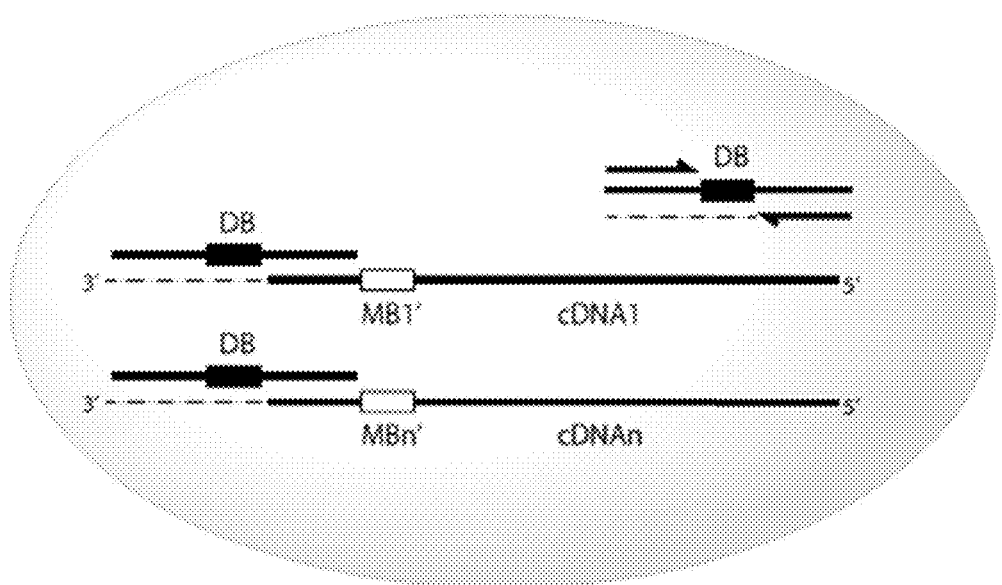
FIG. 1B depicts a schematic of an amplification phase of an exemplary method described herein. The sketch represents a method of amplifying and barcoding two or more polynucleotides, such as paired variable Ig (e.g., $V_H$ and $V_L$ mRNAs) and TCRδ sequences (e.g., Vα/Vβ and Vγ/Vδ mRNAs), such as for library preparation and immune sequencing. (Top) Independent amplification of Vessel Barcodes (VBs) generates a plurality of copies of identical VBs in each droplet. cDNA-MB molecules are simultaneously tagged with the VBs during annealing and extension phases of amplification. (Middle) Simultaneous amplification of dual barcoded cDNA molecules during amplification cycle. (Bottom) Amplification products recovered from droplets in the emulsion.
Figure 1B:
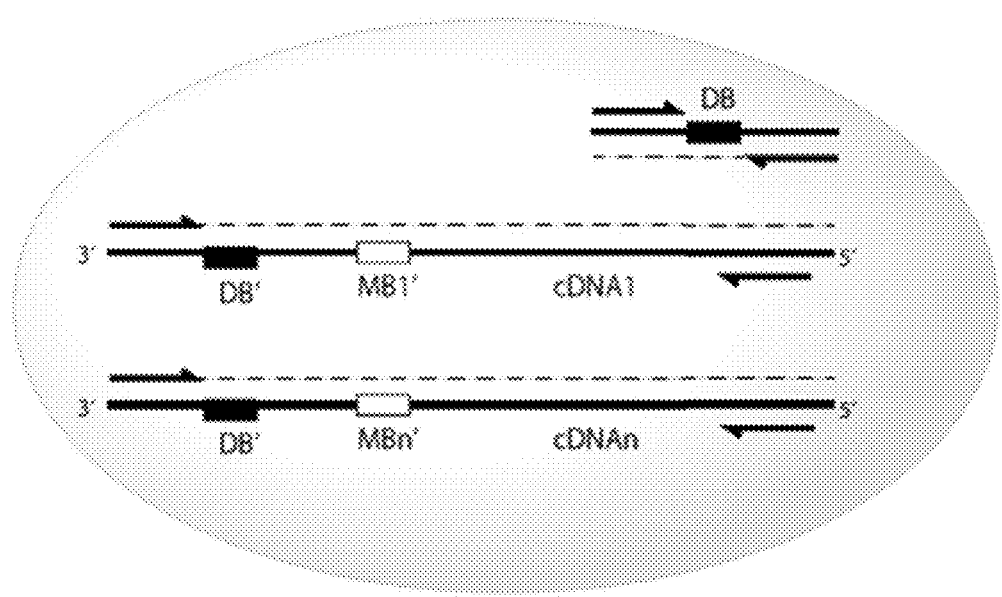
Figure 1B:
Figure 2:
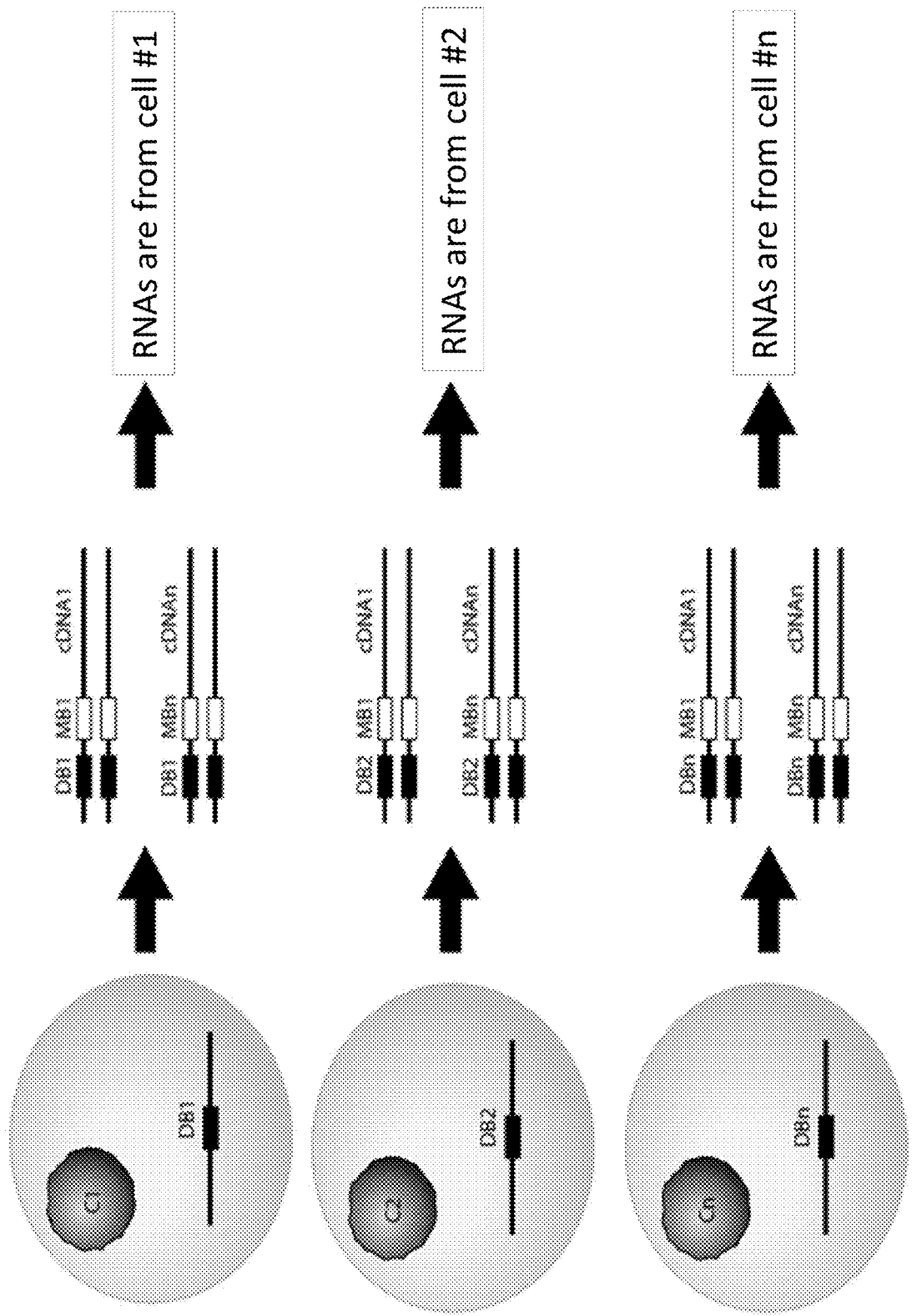
FIG. 2 exemplifies a schematic showing that the sequence identity of the Vessel Barcode (DB) allows for identification of the cell of origin for each RNA.
Figure 3:
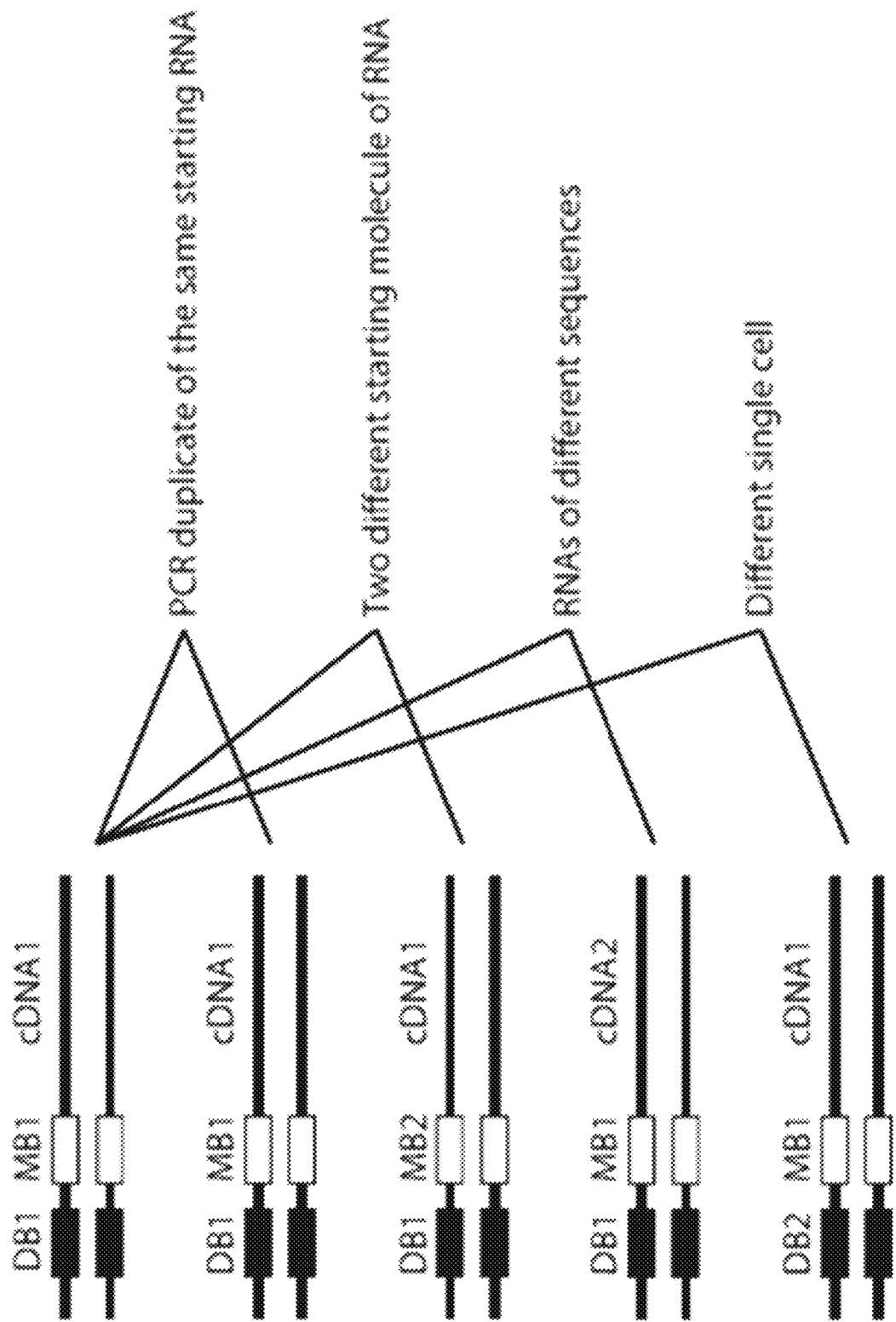
FIG. 3 exemplifies a schematic showing that if the same Molecular Barcode (MB) is found attached to the same identical RNA sequences, then this RNA-MB-DB species is likely the result of PCR duplication. When two different MBs are found attached to the same identical RNA sequences, then these RNA1-MB1-DB and RNA1-MB2-DB are the actual observation of two independent RNA molecules of origin and not of PCR duplication.
Figure 4A:
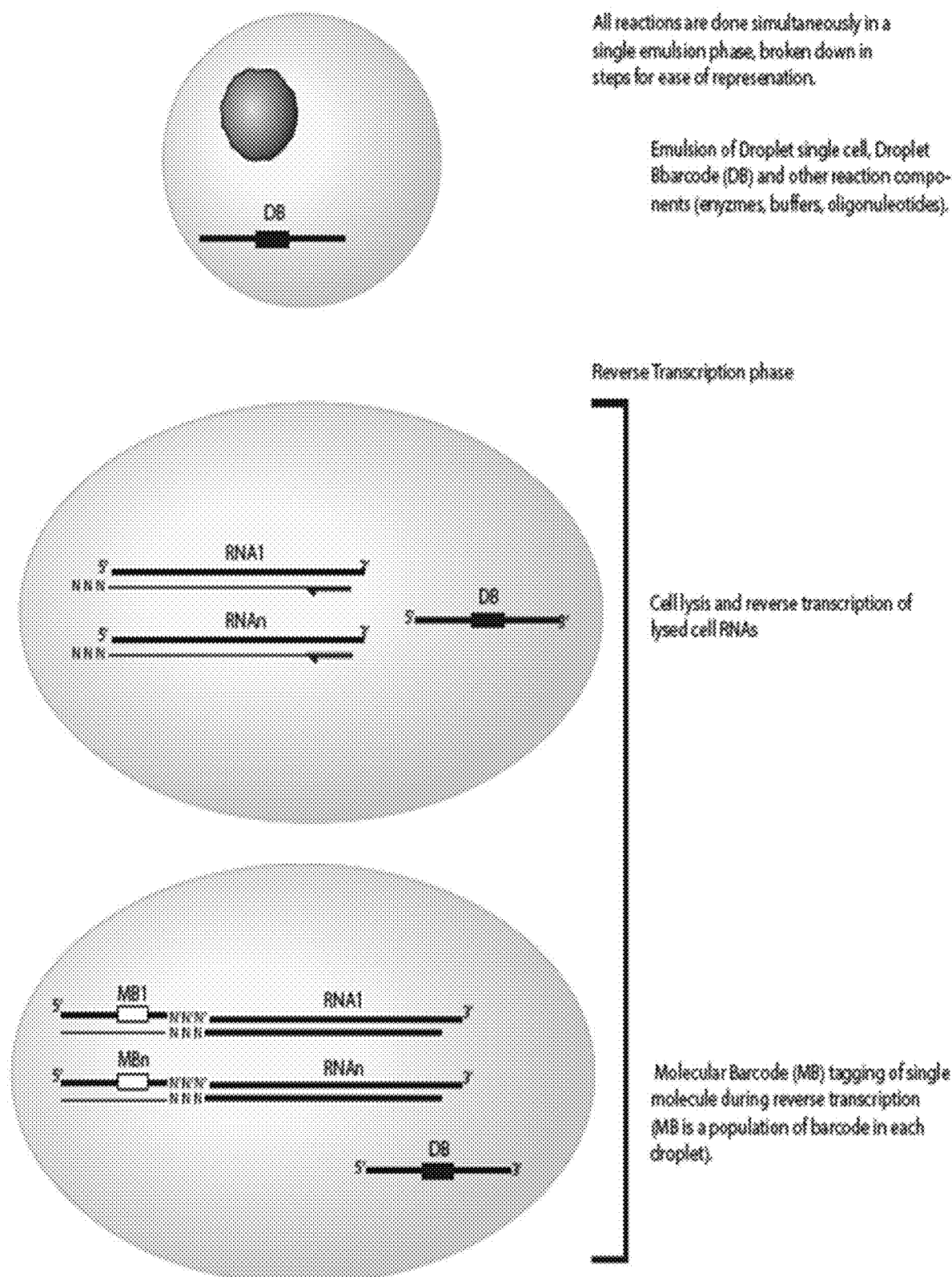
FIG. 4A depicts a schematic of an exemplary method described herein. The sketch represents a method of amplifying and barcoding paired variable Ig (e.g., $V_H$ and $V_L$ sequences) and TCR sequences (e.g., Vα/Vβ and Vγ/Vδ sequences), for library preparation and immune sequencing. Vessel Barcode (DB); Molecular Barcode (MB). Each of the reactions shown can be done in a single emulsion phase and are shown separately for ease of representation.
Figure 4B:
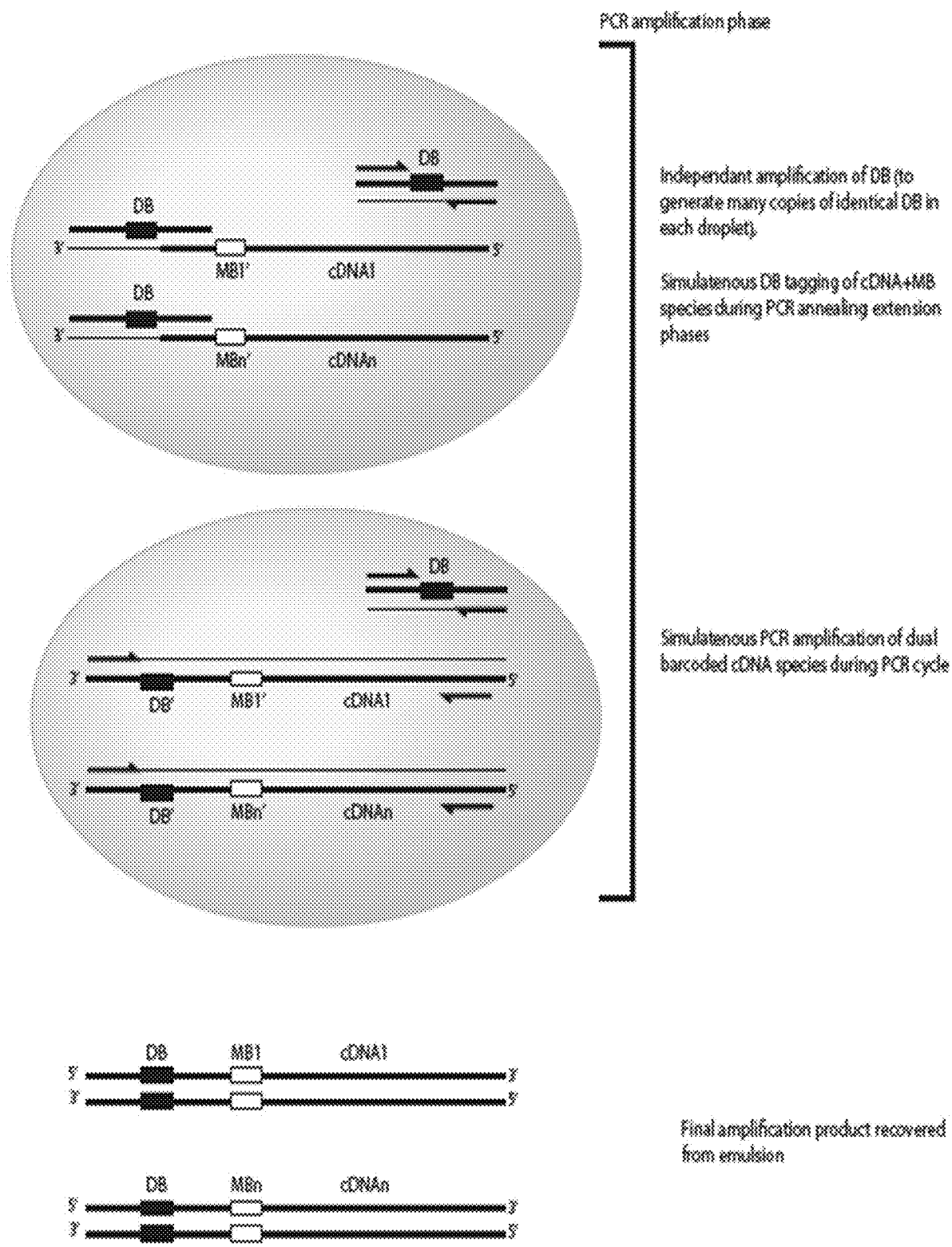
FIG. 4B depicts a schematic of an exemplary method described herein. The sketch represents a method of amplifying and barcoding $V_H$ and $V_L$ antibody mRNA for library preparation and immune sequencing.
Figure 4C:
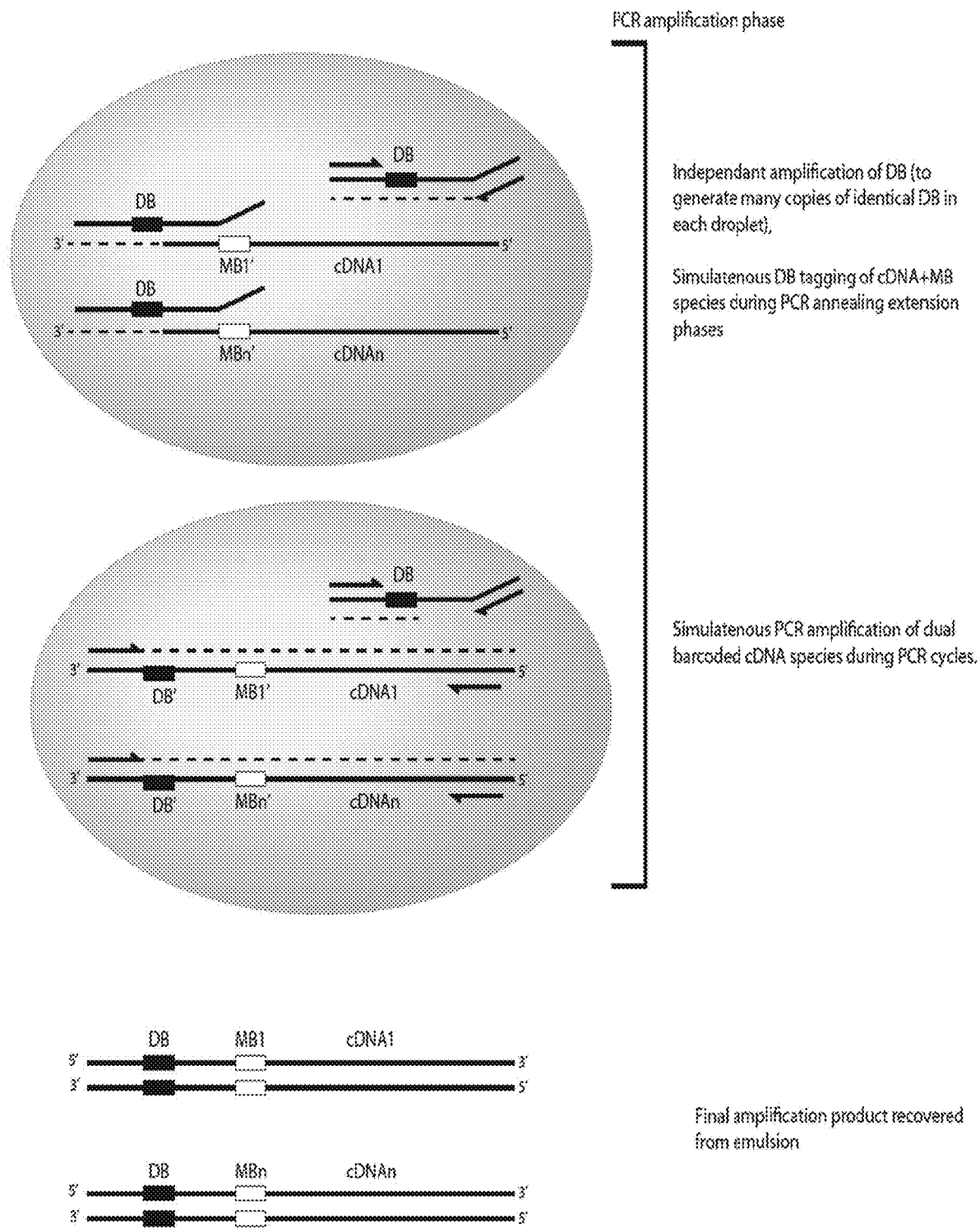
FIG. 4C depicts a schematic of an exemplary method described herein. The sketch exemplifies a method of amplifying and barcoding $V_H$ and $V_L$ antibody mRNA for library preparation and immune sequencing.
Figure 4D:
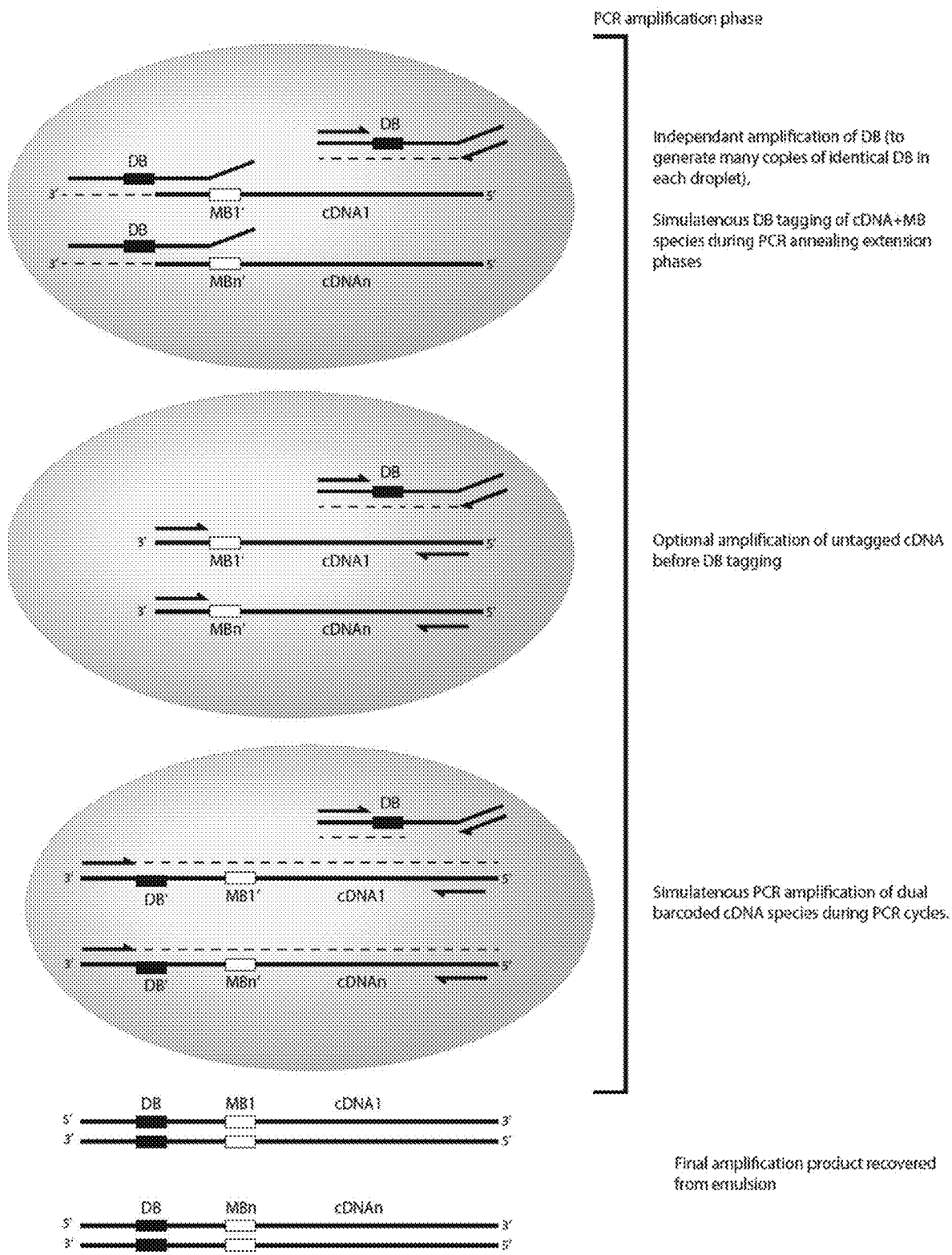
FIG. 4D depicts a schematic of an exemplary method described herein. The sketch exemplifies a method of amplifying and barcoding paired variable Ig (e.g., $V_H$ and $V_L$ sequences) and TCR sequences (e.g., Vα/Vβ and Vγ/Vδ sequences) for library preparation and immune sequencing. An optional step of cDNA amplification prior to tagging the cDNAs with a Vessel Barcode (DB).
Figure 5:
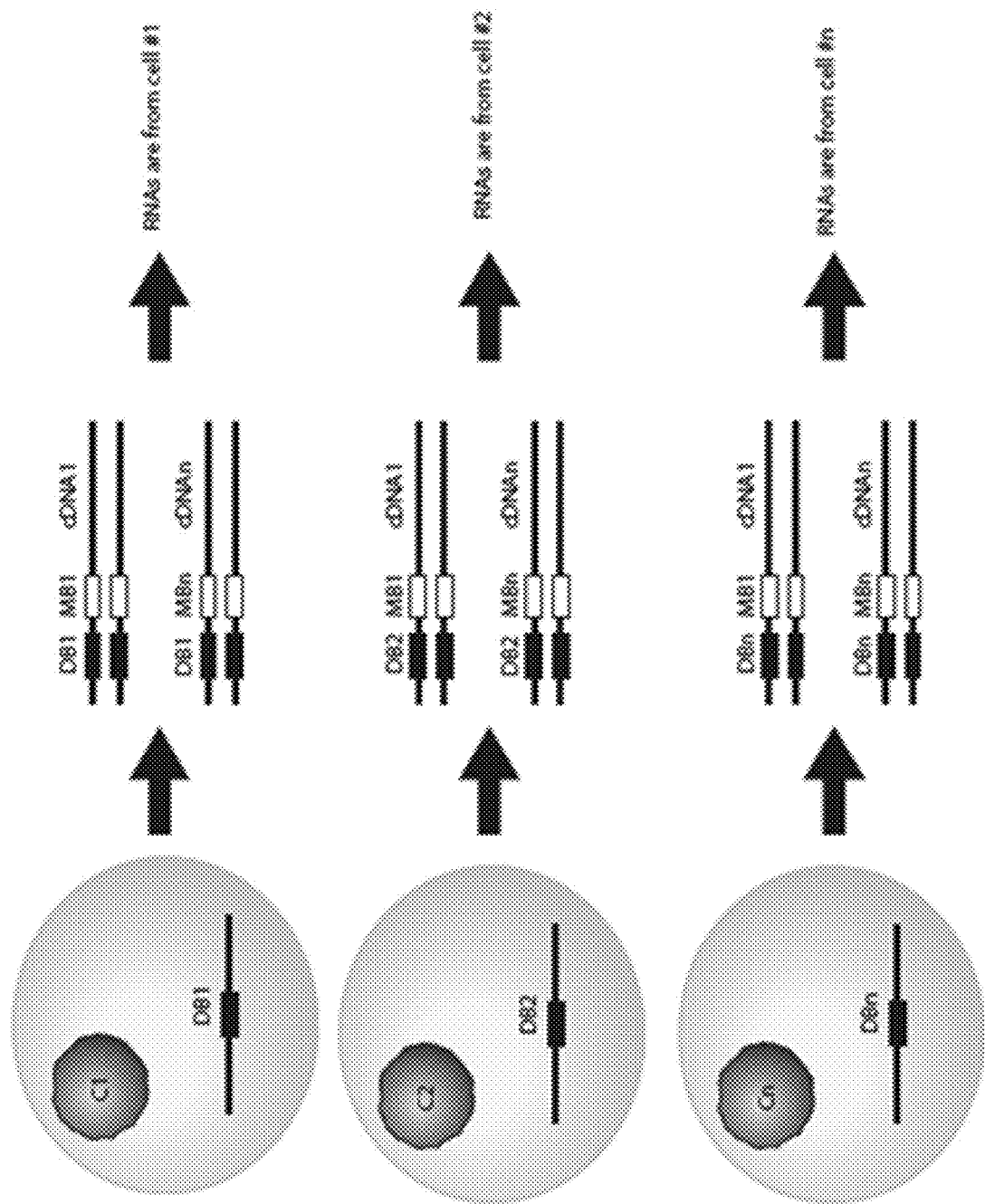
FIG. 5 exemplifies a schematic showing that the sequence identity of the Vessel Barcode (DB) allows for identification of the cell of origin for each RNA. The methods can be used with an emulsion containing a plurality of droplets each containing a single cell to yield dual barcoded cDNAs in a single reaction.
Figure 6:
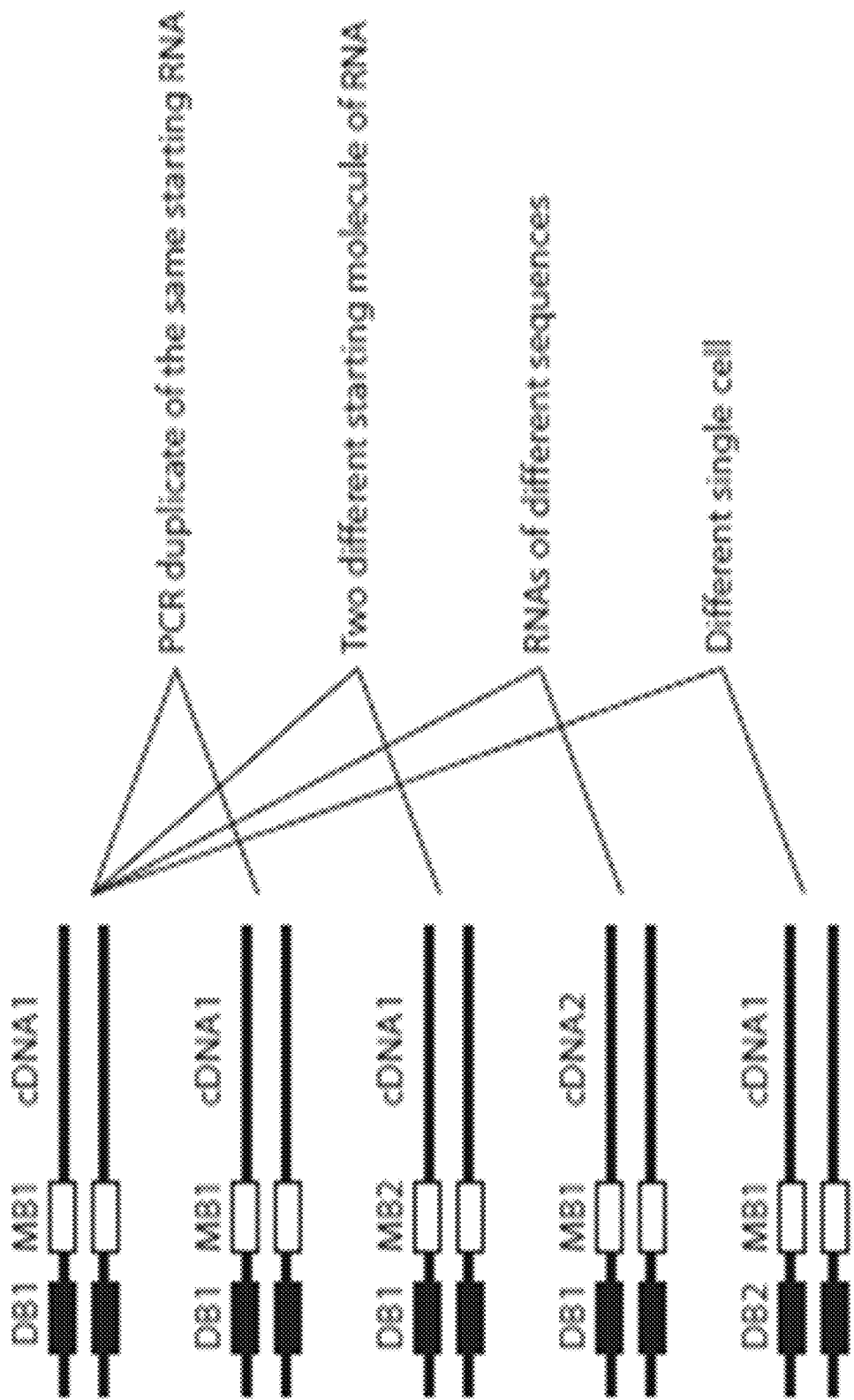
FIG. 6 exemplifies a schematic showing that if the same Molecular Barcode (MB) is found attached to the same identical RNA sequences, then this RNA-MB-DB species is likely the result of PCR duplication. When two different MBs are found attached to the same identical RNA sequences, then these RNA1-MB1-DB and RNA1-MB2-DB is the actual observation of two independent RNA molecule of origin and not of PCR duplication.
Figure 7A:
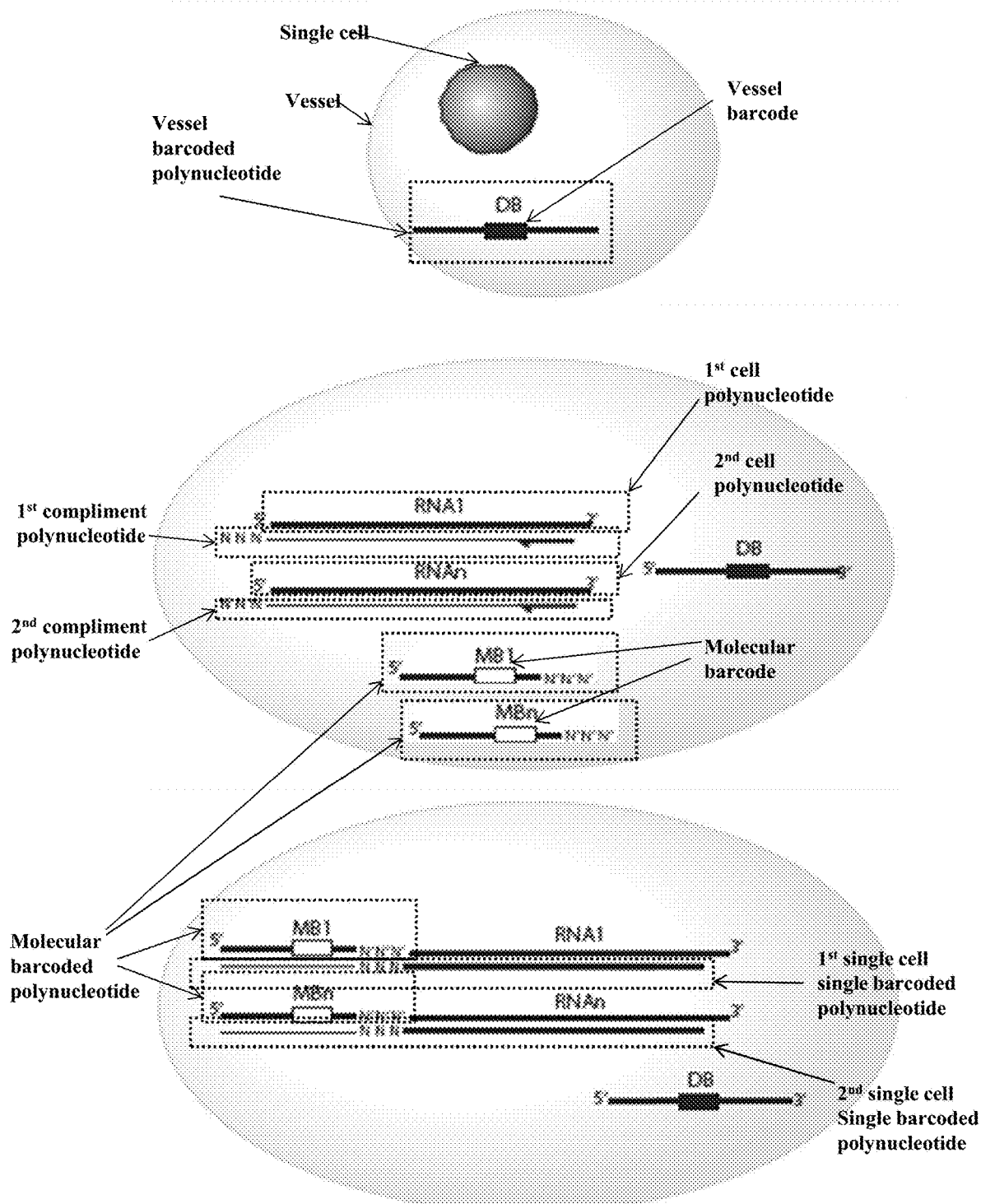
FIG. 7A depicts a schematic of an exemplary method described herein. The sketch represents a legend for the terms in the claims.
Figure 7B:
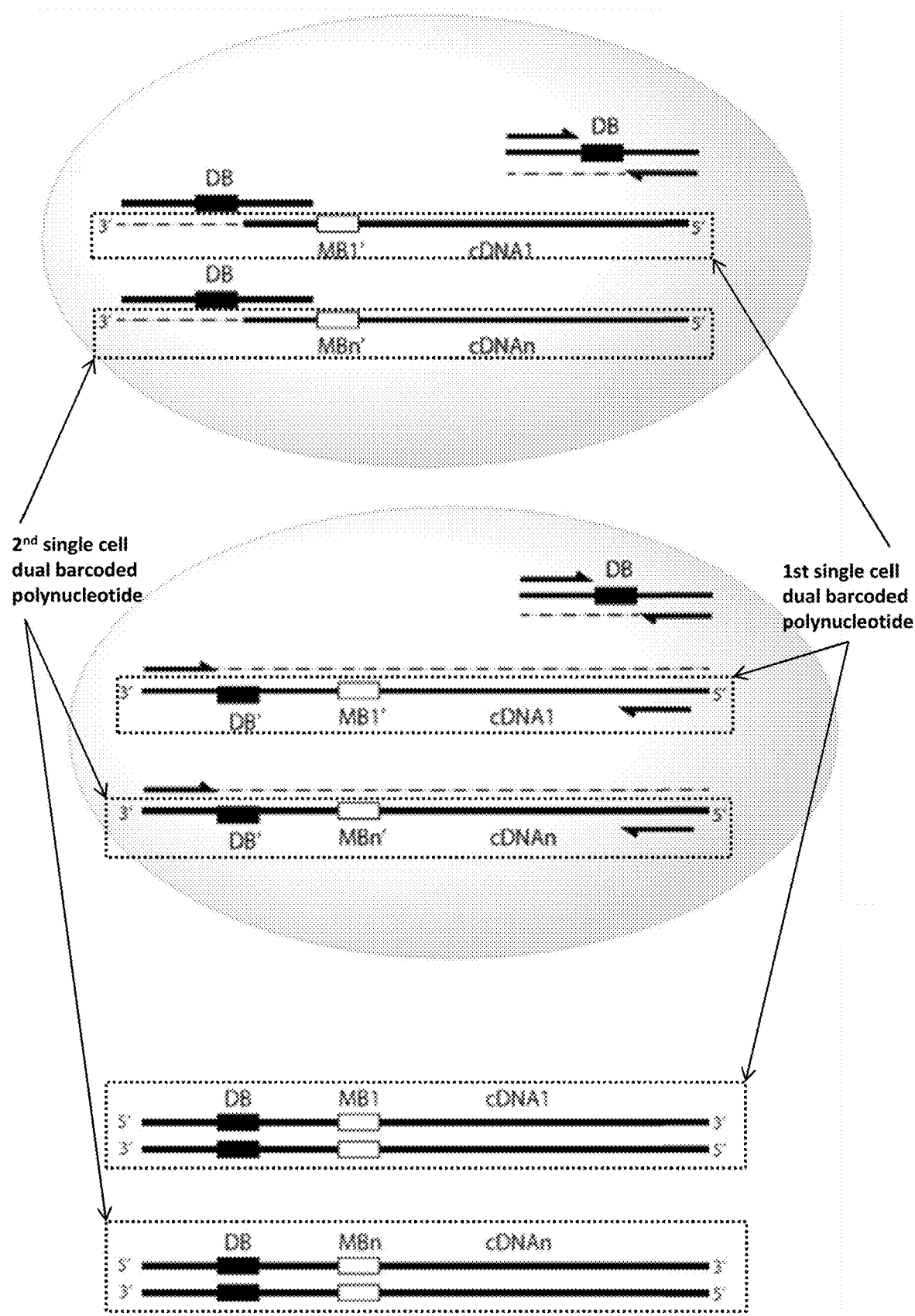
FIG. 7B depicts a schematic of an exemplary method described herein. The sketch represents a method of amplifying and barcoding two or more polynucleotides, such as paired variable Ig (e.g., $V_H$ and $V_L$ mRNAs) and TCR sequences (e.g., Vα/Vβ and Vγ/Vδ mRNAs), such as for library preparation and immune sequencing.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

T cell receptor chain pairs and antibody immunoglobulin chain pairs are both types of immune receptors and are related evolutionarily. It is an object of the invention to generate polynucleotide libraries for high-throughput sequencing and diagnostics. It is also an object of the invention to develop human derived library panels for antibody and/or TCR discovery from patient or cohorts with specific common attributes. Starting material can be peripheral blood or from a tissue biopsy, from which immune cells are globally isolated or sub-sorted for naive, memory and ASC if desired. The disclosed invention can be applied to multiple different types of paired variable sequences, e.g., T-cell receptor chain pairs and antibody immunoglobulin chain pairs.

Isolated cells, such as immune cells, can be encapsulated in vessels, such as water in oil emulsions (droplets), in such a way to create individual picoliter compartments containing a single immune cell or less per droplet. Millions of cells can be processed for each sample, such as a biological sample from a subject, allowing high throughput in single cell sequencing technology. The use of a solid support, such as a bead, can be avoided using the methods described herein. The need to generate to separate populations of vessels can also be avoided using the methods described herein. For example, libraries of sequences can be generated in a same or a single reaction, or in a single plurality or population of vessels. Polynucleotides complementary to cell polynucleotides, such as $V_H$ and $V_L$ antibody chains and/or Vα/Vβ and Vγ/Vδ T-cell receptor (TCR) chains, are introduced during formation of the vessels. A polynucleotide harboring a vessel barcode can also be introduced during formation of the vessels. These vessel barcoded polynucleotides can carry degenerate barcodes such that each cell polynucleotide containing a vessel barcode contains a unique identity code corresponding to the vessel they are in. A plurality of polynucleotides harboring a molecular barcode can also be introduced during formation of the vessels. These molecular barcoded polynucleotides can carry degenerate barcodes such that each cell polynucleotide molecule containing a molecular barcode contains a unique identity code corresponding to a single cell polynucleotide molecule from which they came. The millions of single immune cells can be lysed inside the emulsion and cell transcripts, such as $V_H$ and $V_L$ and/or Vα/Vβ and/or Vγ/Vδ chain transcripts, can be reverse transcribed or copied using primers, followed by tagging with a vessel barcode and a molecular barcode, and PCR amplification of the barcoded polynucleotides. Each $V_H$ and $V_L$ and/or Vα/Vβ and/or Vγ/Vδ chain stemming from a single immune cell (e.g., a B-cell or T-cell) can be virtually linked to each other with the same vessel barcode identity.

The $V_H$ and $V_L$ and/or Vα/Vβ and/or Vγ/Vδ chains can then be recovered from the vessels and PCR enriched in order to add next-generation sequencing (NGS) tags. The library can be sequenced using a high throughput sequencing platform followed by analysis of repertoire diversity, antibody frequency, CDR3 characterization, somatic hypermutation phylogeny analysis, etc. A database of correctly matched $V_H$ and $V_L$ and/or Vα/Vβ and/or Vγ/Vδ pairs can be generated by deconvoluting the vessel and molecular barcode sequences. Because each single immune cell are isolated in their respective vessel, for each vessel barcode observed twice, the transcripts sequenced originated from the same emulsion droplets and therefore from a unique single cell. For each different molecular barcode observed, for sequences containing the same vessel barcode, the transcripts sequenced originated from a different transcript molecule from a single cell. For each same molecular barcode observed, for sequences containing the same vessel barcode, the transcripts sequenced originated from a same transcript molecule from a single cell (e.g., PCR duplicates).

In parallel to the sequencing, a library of $V_H$ and $V_L$ and/or $V\alpha/V\beta$ and/or $V\gamma/V\delta$ chains recovered from the vessels can be cloned into antibody expression vectors and co-transfected for yeast display screening. Cloning this identical library pool is the preferred method compared to splitting a biological sample at the beginning, as some rare immune cells would only be captured in one, or the other assay. The library of human derived $V_H$ and $V_L$ and/or $V\alpha$ and $V\beta$ and/or $V\gamma$ and $V\delta$ chains can be expressed regardless of correct or incorrect pair matching as with classic display assays. Yeast display can then be performed against one or more antigen targets to enrich for potential antibody candidates.

Positive candidate antibodies emerging from display technologies, such as a yeast display, can be sequenced and queried against the barcode database of matched pairs. Each yeast displayed $V_H$ and/or $V\alpha$ and/or $V\gamma$ chain can be matched back to its respective $V_L$ or $V\beta$ or $V\delta$ chain, respectively, and each yeast displayed $V_L$ and/or $V\beta$ and/or $V\delta$ chain can be matched back to its respective $V_H$ or $V\alpha$ or $V\gamma$ chain, respectively. These correctly paired candidates can be gene synthesized and expressed in mammalian cell lines and functionally validated against the target of interest. These candidates can be fully human antibodies and/or TCRs.

An "antibody" refers to an immunoglobulin (Ig) whether natural or partly or wholly synthetically produced. A "T-cell receptor" ("TCR") refers to a molecule, whether natural or partly or wholly synthetically produced, found on the surface of T lymphocytes (T-cells) that recognizes antigens bound to major histocompatibility complex (MHC) molecules. Polypeptides or proteins having a binding domain which is an antigen-binding domain or is homologous to an antigen-binding domain are included. The term further includes "antigen-binding fragments" and other interchangeable terms for similar binding fragments such as described below. Complementarity determining region (CDR) grafted antibodies and TCRs and other humanized antibodies and TCRs (including CDR modifications and framework region modifications) are also contemplated by these terms. It should be noted that while reference may be made only to immunoglobulin chains (e.g., heavy chains and lights chains), the disclosed invention can be applied to multiple other different types of paired sequences, e.g., T-cell receptor chain pairs (TCR$\alpha$ and TCR$\beta$ chains and TCR$\gamma$ and TCR$\delta$ chains), and is not limited to immunoglobulins.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains ($C_H$). Each light chain has a variable domain at one end ($V_L$) and a constant domain ($C_L$) at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. Antibodies can be assigned to different classes Depending on the amino acid sequence of the constant domain of their heavy chains, including IgA, IgD, IgE, IgG, and IgM, and several of these may be further divided into subclasses (isotypes), e.g., $IgG_1$, $IgG_2$, $IgG_3$, $IgG_4$, IgA, and $IgA_2$. The heavy chains (IgHs) of antibodies correspond to different classes of immunoglobulins called $\alpha$, $\delta$, $\epsilon$, $\gamma$, and $\mu$, respectively, based on the amino acid sequences of their constant domains. The light chains (IgLs) of antibodies from any vertebrate species can be assigned to one of two clearly distinct types, called kappa ($\kappa$) and lambda ($\lambda$), based on the amino acid sequences of their constant domains.

The ability of T-cells to recognize antigens associated with various cancers or infectious organisms is conferred by its TCR, which is made up of both an alpha ($\alpha$) chain and a beta ($\beta$) chain or a gamma ($\gamma$) and a delta ($\delta$) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC is a central event in T-cell activation, which occurs at an immunological synapse at the point of contact between the T-cell and the APC.

Each TCR contains variable complementarity determining regions (CDRs), as well as framework regions (FRs) and a constant region. The amino acid sequence of the third complementarity-determining region (CDR3) loops of the $\alpha$ and $\beta$ chain variable domains is largely determines the sequence diversity of $\alpha\beta$ T-cells arising from recombination between variable (V$\beta$), diversity (D$\beta$), and joining (J$\beta$) gene segments in the $\beta$ chain locus, and between analogous V$\alpha$ and J$\alpha$ gene segments in the $\alpha$ chain locus, respectively. The existence of multiple such gene segments in the TCR $\alpha$ and $\beta$ chain loci allows for a large number of distinct CDR3 sequences to be encoded. Independent addition and deletion of nucleotides at the V$\beta$-D$\beta$, D$\beta$-J$\beta$, and V$\alpha$-J$\alpha$ junctions during the process of TCR gene rearrangement further increases CDR3 sequence diversity. In this respect, immunocompetence is reflected in the diversity of TCRs.

The $\gamma\delta$ TCR is distinctive from the TCR in that it encodes a receptor that interacts closely with the innate immune system. TCR$\gamma\delta$, is expressed early in development, has specialized anatomical distribution, has unique pathogen and small-molecule specificities, and has a broad spectrum of innate and adaptive cellular interactions. Early in ontogeny, as the restricted subsets of TCR$\gamma\delta$ cells populate various tissues prenatally, a biased pattern of TCR$\gamma$ V and J segment expression is established. Thus, extensive peripheral expansion following stimulation by environmental exposure to pathogens and toxic molecules causes much of the diverse TCR$\gamma$ repertoire in adult tissues.

Igs expressed by B-cells are proteins consisting of four polypeptide chains, two heavy chains (IgHs) and two light chains (IgLs), forming an $H_2L_2$ structure. Each pair of IgH and IgL chains contains a hypervariable domain, consisting of a $V_L$ and a $V_H$ region, and a constant domain. The IgH chains of Igs are of several types, $\mu$, $\delta$, $\gamma$, $\alpha$, and $\beta$. The diversity of Igs within an individual is mainly determined by the hypervariable domain. Similar to the TCR, the V domain of IgH chains is created by the combinatorial joining of the $V_H$, $D_H$, and $J_H$ gene segments. Independent addition and deletion of nucleotides at the $V_H$-$D_H$, $D_H$-$J_H$, and $V_H$-$J_H$ junctions during the process of Ig gene rearrangement further increases hypervariable domain sequence diversity. Here, immunocompetence is reflected in the diversity of Igs.

"Variable" with reference to antibody chains, e.g., heavy and light chains, or TCR chains, e.g., alpha (α) and beta chains or gamma (γ) and delta (δ) chains, refers to portions of the antibody or TCR chains which differ in sequence among antibodies or TCRs and participate in the binding and specificity of each particular antibody or TCR for its particular antigen. Such variability is concentrated in three segments called hypervariable regions both in the light chain and the heavy chain variable domains or the alpha and beta variable domains. The more highly conserved portions of variable domains are called the framework region (FR). The variable domains of native heavy and light chains each comprise four FRs (FR1, FR2, FR3 and FR4, respectively), connected by three hypervariable regions. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody or TCR to an antigen, but exhibit various effector functions, e.g., participation of the antibody in antibody-dependent cellular toxicity.

A "hypervariable region" refers to the amino acid residues of an antibody or TCR which are responsible for antigen-binding. The hypervariable region comprises amino acid residues from a "complementarity determining region" or "CDR." "Framework" or "FR" residues are those variable domain residues other than the hypervariable region residues as herein defined.

"Antibody fragments" and "TCR fragments" comprise a portion of a full length antibody or TCR, generally the antigen binding or variable domain thereof. Examples of antibody and TCR fragments include, but are not limited to, Fab, Fab', F(ab')$_2$, Fv, and scFv fragments, linear antibodies or TCRs, single-chain antibody or TCR molecules, diabodies, and multispecific antibodies or TCRs formed from antibody or TCR fragments.

A "monoclonal antibody" refers to an antibody molecule synthesized by a single clone of immune cells. The modifier "monoclonal" indicates the character of the antibody as being obtained from a substantially homogeneous population of antibodies, and is not to be construed as requiring production of the antibody by any particular method. Thus, monoclonal antibodies may be made by the hybridoma method first described by Kohler and Milstein, Nature 256:495 (1975); Eur. J. Immunol. 6:511 (1976), by recombinant DNA techniques, or may also be isolated from phage antibody libraries.

A "polyclonal antibody" refers to a population of antibody molecules synthesized by a population of immune cells.

A "single-chain Fv" or "scFv" refers to antibody or TCR fragments that comprise the variable heavy chain ($V_H$) and variable light chain ($V_L$) domains of an antibody or the variable alpha or gamma chain (Vα or Vγ) and variable beta or delta chain (Vβ or Vδ) domains of a TCR, wherein these domains are present in a single polypeptide chain. Generally, the Fv polypeptide further comprises a polypeptide linker between the $V_H$ and $V_L$ domains or Vα and Vβ domains or Vγ and Vδ domains which enables the sFv to form the desired structure for antigen binding.

A "diabody" refers to small antibody and/or TCR fragments with two antigen-binding sites, which fragments comprise a $V_H$ connected to a $V_L$ in the same polypeptide chain ($V_H$-$V_L$) or a Vα connected to a Vβ in the same polypeptide chain (Vα-Vβ) or a Vγ connected to a Vδ in the same polypeptide chain (Vγ-Vδ). By using a linker that is too short to allow pairing between the two domains on the same chain, the domains are forced to pair with the complementary domains of another chain and create two antigen-binding sites. Exemplary diabodies are described more fully in, for example, EP404097 and WO93111161.

A "bispecific antibody" or "bispecific TCR" refers to an antibody or TCR that shows specificities to two different types of antigens. The terms as used herein specifically include, without limitation, antibodies and TCRs which show binding specificity for a target antigen and to another target that facilitates delivery to a particular tissue. Similarly, multi-specific antibodies and TCRs have two or more binding specificities.

A "linear antibody" or "linear "TCR" refers to a pair of tandem Fd segments (e.g., $V_H$-$C_{H1}$-$V_H$-$C_{H1}$ or Vα-Cα$_1$-Vα-Cα$_1$) which form a pair of antigen binding regions. Linear antibodies and TCRs can be bispecific or monospecific, for example, as described by Zapata et al., Protein Eng. 8(10): 1057-1062 (1995).

An "antigen-binding domain" refers to one or more fragments of an antibody or TCR that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are antibodies comprising a single heavy chain and a single light chain or TCRs with a single alpha chain or a single beta chain.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which a light chain composed of $V_L$ and $C_L$, and a heavy chain fragment composed of $V_H$ and $C_{H\gamma 1}$ (γ1 region in the constant region of the heavy chain) are connected at their C terminal regions through a disulfide bond. Each of these two homologous antibody fragments is called 'Fab'. Pepsin also cleaves IgG downstream of the disulfide bonds existing between the hinge regions in each of the two heavy chains to generate an antibody fragment slightly larger than the fragment in which the two above-mentioned 'Fab' are connected at the hinge region. This antibody fragment is called F('ab')$_2$. The Fab fragment also contains the constant domain of the light chain and the first constant domain ($C_H$1) of the heavy chain. 'Fab' fragments differ from Fab fragments by the addition of a few residues at the carboxyl terminus of the heavy chain $C_H$1 domain including one or more cysteine(s) from the antibody hinge region. Fab'-SH is the designation herein for Fab' in which the cysteine residue(s) of the constant domains bear a free thiol group. F(ab')$_2$ antibody fragments originally are produced as pairs of Fab' fragments which have hinge cysteines between them.

"Fv" refers to an antibody or TCR fragment which contains a complete antigen-recognition and antigen-binding site. This region consists of a dimer of one heavy chain and one light chain variable domain or one TCRα chain and one TCRβ chain or one TCRγ chain and one TCRδ chain in tight, noncovalent association. It is in this configuration that the three CDRs of each variable domain interact to define an antigen-binding site on the surface of the $V_H$-$V_L$ dimer or Vα-Vβ dimer or Vγ-Vδ dimer. Collectively, a combination of one or more of the CDRs from each of the $V_H$ and $V_L$ chains or Vα-Vβ chains or Vγ-Vδ chains confers antigen-binding specificity to the antibody or TCR. For example, it would be understood that, for example, the CDRH3 and CDRL3 could be sufficient to confer antigen-binding specificity to an antibody or TCR when transferred to $V_H$ and $V_L$ chains or Vα and Vβ chains or Vγ-Vδ chains of a recipient selected antibody, TCR, or antigen-binding fragment thereof and this combination of CDRs can be tested for binding, affinity, etc. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$ or Vα and Vβ or Vγ and Vδ), are coded for by separate genes, they can be joined using recombinant methods by a synthetic linker that enables them to be made as a single protein chain in which the $V_L$ and $V_H$ or Vα and Vβ or Vγ and Vδ chain regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129).

"Humanized" forms of non-human (e.g., murine) antibodies or TCRs include chimeric antibodies or TCRs which contain minimal sequence derived from a non-human Ig or TCR. For the most part, humanized antibodies or TCRs are human Igs or TCRs (recipient antibody or TCR) in which one or more of the CDRs of the recipient are replaced by CDRs from a non-human species antibody or TCR (donor antibody or TCR) such as mouse, rat, rabbit or non-human primate having the desired specificity, affinity and binding function. In some instances, one or more FR amino acid residues of the human Ig or TCR are replaced by corresponding non-human amino acid residues. Furthermore, humanized antibodies or TCRs can contain residues which are not found in the recipient antibody or TCR, or in the donor antibody or TCR. These modifications can be made to refine antibody or TCR performance, if needed. A humanized antibody or TCR can comprise substantially all of at least one and, in some instances two, variable domains, in which all or substantially all of the hypervariable regions correspond to those of a non-human immunoglobulin or TCR and all, or substantially all, of the FRs are those of a human immunoglobulin or TCR sequence. The humanized antibody or TCR optionally can also include at least a portion of an immunoglobulin or TCR constant region (Fc), typically that of a human immunoglobulin or TCR. See, e.g., Jones et al., Nature 321: 522-525 (1986); Reichmann et al., Nature 332: 323-329 (1988); and Presta, Curr. Op. Struct. Biol. 2: 593-596 (1992).

A "germline sequence" refers to a genetic sequence from the germline (the haploid gametes and those diploid cells from which they are formed). Germline DNA contains multiple gene segments that encode a single Ig heavy or light chain, or a single TCRα or TCRβ chain, or a single TCRγ or TCRδ chain. These gene segments are carried in the germ cells but cannot be transcribed and translated until they are arranged into functional genes. During B-cell and T-cell differentiation in the bone marrow, these gene segments are randomly shuffled by a dynamic genetic system capable of generating more than $10^8$ specificities. Most of these gene segments are published and collected by the germline database.

"Affinity" refers to the equilibrium constant for the reversible binding of two agents and is expressed as $K_D$. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

An "epitope" refers to that portion of an antigen or other macromolecule capable of forming a binding interaction with the variable region binding pocket of an antibody or TCR. Such binding interactions can be manifested as an intermolecular contact with one or more amino acid residues of one or more CDRs. Antigen binding can involve, for example, a CDR3, a CDR3 pair, or in some instances, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody or TCR can recognize one or more amino acid sequences; therefore an epitope can define more than one distinct amino acid sequence. Epitopes recognized by antibodies and TCRs can be determined by peptide mapping and sequence analysis techniques well known to one of skill in the art. Binding interactions are manifested as intermolecular contacts with one or more amino acid residues of a CDR.

"Specific" refers to a situation in which an antibody or TCR will not show any significant binding to molecules other than the antigen containing the epitope recognized by the antibody or TCR. The term is also applicable where for example, an antigen binding domain is specific for a particular epitope which is carried by a number of antigens, in which case the selected antibody, TCR, or antigen-binding fragment thereof carrying the antigen binding domain will be able to bind to the various antigens carrying the epitope. The terms "preferentially binds" or "specifically binds" mean that the antibodies, TCRs, or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody, TCR, or fragment thereof for unrelated amino acid sequences. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

"Pharmaceutically acceptable" refers to molecular entities and compositions that are physiologically tolerable and do not typically produce an allergic or similar untoward reaction, such as gastric upset, dizziness and the like, when administered to a human.

A "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

A "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

"Prevention" refers to prophylaxis, prevention of onset of symptoms, prevention of progression of a disease or disorder associated with excess levels of protein or correlated with protein activity.

"Inhibition," "treatment" and "treating" are used interchangeably and refer to, for example, stasis of symptoms, prolongation of survival, partial or full amelioration of symptoms, and partial or full eradication of a condition, disease or disorder associated with excess levels of protein or correlated with protein activity. For example, treatment of cancer includes, but is not limited to, stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

A "neutralizing antibody" or "neutralizing TCR" refers to any antibody or TCR that inhibits replication of a pathogen, such as a virus or bacteria, regardless of the mechanism by which neutralization is achieved.

An "antibody repertoire" or "TCR repertoire" refers to a collection of antibodies, TCR, or fragments thereof. An antibody repertoire can, for example, be used to select a particular antibody or screen for a particular property, such as binding ability, binding specificity, ability of gastrointestinal transport, stability, affinity, and the like. The term specifically includes antibody and TCR libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

A "target nucleic acid molecule," "target molecule," "target polynucleotide," "target polynucleotide molecule," refers to any nucleic acid of interest.

A polymerase chain reaction (PCR) refers to an in vitro amplification reaction of polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. (McPherson et al., IRL Press, Oxford (1991 and 1995)). For example, in a conventional PCR using Taq DNA polymerase, a double stranded template polynucleotide can be denatured at a temperature >90° C., primers can be annealed at a temperature in the range 50-75° C., and primers can be extended at a temperature in the range 72-78° C. In some embodiments, PCR comprises Reverse transcription PCR (RT-PCR), real-time PCR, nested PCR, quantitative PCR, multiplexed PCR, or the like. In some embodiments, PCR does not comprise RT-PCR. (U.S. Pat. Nos. 5,168,038, 5,210,015, 6,174,670, 6,569,627, and 5,925,517; Mackay et al., Nucleic Acids Research, 30: 1292-1305 (2002)). RT-PCR comprises a PCR reaction preceded by a reverse transcription reaction and a resulting cDNA is amplified, Nested PCR comprises a two-stage PCR wherein an amplicon of a first PCR reaction using a first set of primers becomes the sample for a second PCR reaction using a second primer set, at least one of which binds to an interior location of an amplicon of a first PCR reaction. Multiplexed PCR comprises a PCR reaction, wherein a plurality of polynucleotide sequences is subjected to PCR in the same reaction mixture simultaneously. PCR reaction volumes can be anywhere from 0.2 pL-1000 µL. Quantitative PCR comprises a PCR reaction designed to measure an absolute or relative amount, abundance, or concentration of one or more sequences in a sample. Quantitative measurements can include comparing one or more reference sequences or standards to a polynucleotide sequence of interest. (Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989)).

In other embodiments, the methods, kits, and compositions disclosed herein may comprise a support. In some embodiments, the methods, kits, and compositions disclosed herein do not comprise a support. Typically, a solid support comprises one or more materials comprising one or more rigid or semi-rigid surfaces. In some embodiments, the support is a non-solid support. The support or substrate may comprise a membrane, paper, plastic, coated surface, flat surface, glass, slide, chip, or any combination thereof. In some embodiments, one or more surfaces of a support are substantially flat, although in some embodiments it may be desirable to physically separate synthesis regions for different compounds with, for example, wells, raised regions, pins, etched trenches, or the like. In some embodiments, solid supports comprise beads, resins, gels, microspheres, or other geometric configurations. Alternatively, solid supports can comprises silica chips, microparticles, nanoparticles, plates, and arrays. The solid support can comprise the use of beads that self-assemble in microwells. For example, the solid support comprises Illumina's BeadArray Technology. Alternatively, the solid support comprises Abbott Molecular's Bead Array technology, and Applied Microarray's FlexiPlex™ system. In other instances, the solid support is a plate. Examples of plates include, but are not limited to, MSD multi-array plates, MSD Multi-Spot® plates, microplate, ProteOn microplate, AlphaPlate, DELFIA plate, IsoPlate, and LumaPlate. In some embodiments, a support can comprise a plurality of beads. In some embodiments, a support can comprise an array. In some embodiments, a support can comprise a glass slide. Methods, substrates, and techniques applicable to polymers (U.S. Pat. Nos. 5,744,305, 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752; US Patent Pub. Nos. 20090149340, 20080038559, 20050074787; and in PCT Publication Nos. WO 00/58516, WO 99/36760, and WO 01/58593). The attachment of the polynucleotides to a support may comprise amine-thiol crosslinking, maleimide crosslinking, N-hydroxysuccinimide or N-hydroxysulfosuccinimide, Zenon or SiteClick. Attaching the labeled nucleic acids to the support may comprise attaching biotin to the plurality of polynucleotides and coating the one or more beads with streptavidin. In some embodiments, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide dT conjugated beads, silica beads, silica-like beads, anti-biotin microbead, anti-fluorochrome microbead, and BcMag™ Carboxy-Terminated Magnetic Beads. The diameter of the beads may be about 5 µm, 10 µm, 20 µm, 25 µm, 30 µm, 35 µm, 40 µm, 45 µm or 50 µm. The solid support may be an array or microarray. The solid support may comprise discrete regions. The solid support may be an array, e.g., an addressable array.

"Nucleotide," "nucleoside," "nucleotide residue," and "nucleoside residue," as used herein, can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate. In some embodiments, nucleotide analogs can stabilize hybrid formation. In some embodiments, nucleotide analogs can destabilize hybrid formation. In some embodiments, nucleotide analogs can enhance hybridization specificity. In some embodiments, nucleotide analogs can reduce hybridization specificity.

A "nucleic acid", or grammatical equivalents, refers to either a single nucleotide or at least two nucleotides covalently linked together.

A "polynucleotide" or "polynucleotide" or "polynucleotide" or grammatical equivalents refers to at least two nucleotides covalently linked together. A polynucleotide comprises a molecule containing two or more nucleotides. A polynucleotide comprises polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatives of nucleotide bases. The backbone of the polynucleotide can comprise sugars and phosphate groups, or modified or substituted sugar or phosphate groups. A polynucleotide may comprise modified nucleotides, such as methylated nucleotides and nucleotide analogs. The sequence of nucleotides may be interrupted by non-nucleotide components. A polynucleotide can include other molecules, such as another hybridized polynucleotide. Polynucleotides include sequences of deoxyribonucleic acid (DNA), ribonucleic acid (RNA), or both. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Polynucleotides can be isolated from natural sources, recombinant, or artificially synthesized.

A polynucleotide comprises a specific sequence of four nucleotide bases: adenine (A); cytosine (C); guanine (G); and thymine (T) (uracil (U) for thymine (T) when the polynucleotide is RNA). Thus, a polynucleotide sequence is the alphabetical representation of a polynucleotide molecule; alternatively, the term may be applied to the polynucleotide molecule itself. This alphabetical representation can be input into databases in a computer having a central processing unit and used for bioinformatics applications such as functional genomics, homology searching, binning sequences, aligning sequences, and determining consensus sequences.

Polynucleotides can include nonstandard nucleotides, such as nucleotide analogs or modified nucleotides. In some embodiments, nonstandard nucleotides can stabilize hybrid formation. In some embodiments, nonstandard nucleotides can destabilize hybrid formation. In some embodiments, nonstandard nucleotides can enhance hybridization specificity. In some embodiments, nonstandard nucleotides can reduce hybridization specificity. Examples of nonstandard nucleotide modifications include 2' O-Me, 2' O-allyl, 2' O-propargyl, 2' O-alkyl, 2' fluoro, 2' arabino, 2' xylo, 2' fluoro arabino, phosphorothioate, phosphorodithioate, phosphoroamidates, 2' Amino, 5-alkyl-substituted pyrimidine, 3' deoxyguanosine, 5-halo-substituted pyrimidine, alkyl-substituted purine, halo-substituted purine, bicyclic nucleotides, 2'MOE, PNA molecules, LNA-molecules, LNA-like molecules, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methyl guanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxy acetic acid (v), 5-methyl-2-thiouracil, 3-(3-amino-3-N-2-carboxypropyl) uracil, (acp3)w, 2,6-diaminopurine, and derivatives thereof.

A "subject", "individual", "host" or "patient" refers to a living organisms such as mammals. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof. In certain aspects, a subject refers to a single organism (e.g., human). In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

A "kit" refers to a delivery system for delivering materials or reagents for carrying out a method disclosed herein. In some embodiments, kits include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains a plurality of primers.

A "polypeptide" refers to a molecule comprising at least two amino acids. In some embodiments, the polypeptide consists of a single peptide. In some embodiments, a polypeptide comprises two or more peptides. For example, a polypeptide can comprise at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides or amino acids. Examples of polypeptides include, but are not limited to, amino acid chains, proteins, peptides, hormones, polypeptide saccharides, lipids, glycolipids, phospholipids, antibodies, enzymes, kinases, receptors, transcription factors, and ligands.

A "sample" refers to a biological, environmental, medical, subject, or patient sample or a sample containing a polynucleotide, such as a target polynucleotide.

Samples

Any biological sample containing polynucleotides can be used in the methods described herein. For example, a sample can be a biological sample from a subject containing RNA or DNA. The polynucleotides can be extracted from the biological sample, or the sample can be directly subjected to the methods without extraction or purification of the polynucleotides. The sample can be extracted or isolated DNA or RNA. A sample can also be total RNA or DNA extracted from a biological specimen, a cDNA library, viral, or genomic DNA. In one embodiment, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the polynucleotides are obtained from a single cell. Polynucleotides can be obtained directly from an organism or from a biological sample obtained from an organism. Any tissue or body fluid specimen may be used as a source for nucleic acid for use in the invention. Polynucleotides can also be isolated from cultured cells, such as a primary cell culture or a cell line. The cells or tissues from which template nucleic acids are obtained can be infected with a virus or other intracellular pathogen.

In certain embodiments, antibody or TCR-producing immune cells can be isolated from the blood or other biological samples of a subject or host, such as a human or other animal, such as a human or other animal that has been immunized or that is suffering from an infection, cancer, an autoimmune condition, or any other diseases to identify a pathogen-, tumor-, and/or disease specific antibody or TCR of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies or TCRs against an infectious agent (e.g., viruses, bacteria, parasites, prions, etc), antigen, or disease. For example, the animal may be one that was exposed to and/or who can make useful antibodies or TCRs against an infectious agent (e.g., viruses, bacteria, parasites, prions, etc), antigen, or disease. Certain immune cells from immunized hosts make antibodies or TCRs to one or more target antigens in question and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as an immune cell library, before antibody chains are sequenced, antibodies are made, or an expression library is/are made. In contrast to prior art enrichment methods, which provide only a few subsets of immune cells expressing different antibodies, and therefore only a few naturally occurring combinations of variable domains, the immune cell library of the present invention contains at least 2 subsets of or individual immune cells expressing different antibodies or TCRs. For example, the immune cell library of the present invention can contain at least 5, 10, 100, 250, 500, 750, 1000, 2500, 5000, 10000, 25000, 50000, 75000, 10000, 250000, 500000, 750000, 1000000, 2500000, 5000000, 7500000, or 10000000 subsets of or individual immune cells expressing different antibodies or TCRs. The methods of the present invention maximize immune cell recovery, and afford very high diversity.

In some embodiments, immune cells from non-immunized human or non-human donors are utilized. The naive repertoire of an animal (the repertoire before antigen challenge) provides the animal with antibodies or TCRs that can bind with moderate affinity ($K_A$ of about $1 \times 10^{-6}$ to $1 \times 10^{-7}$ M) to essentially any non-self molecule. The sequence diversity of antibody or TCR binding sites is not encoded directly in the germline but is assembled in a combinatorial manner from V gene segments. Immunizations trigger any immune cell making a $V_H$-$V_L$ or Vα-Vβ or Vγ-Vδ combination that binds the immunogen to proliferate (clonal expansion) and to secrete the corresponding antibody as noted above. However, the use of spleen cells and/or immune cells or other peripheral blood lymphocytes (PBLs) from an unimmunized subject can provide a better representation of the possible antibody or TCR repertoire, and also permits the construction of a subsequent B-cell or T-cell antibody or TCR library using any animal species.

In some cases, in order to obtain sufficient nucleic acid for testing, a blood volume of at least 0.001, 0.005, 0.01, 0.05, 0.1, 0.5, 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; $CD4^+$ cells; $CD8^+$ cells; immune cells; T cells, NK cells, or the like). The peripheral blood cells can also be selectively depleted of a particular cell type (e.g., mononuclear cells; red blood cells; $CD4^+$ cells; $CD8^+$ cells; immune cells; T cells, NK cells, or the like).

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular B-cells or T-cells. In some cases, the starting material can be a sample containing nucleic acids, from any organism, from which genetic material can be obtained. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, non-nucleic acid materials can be removed from the starting material using enzymatic treatments (such as protease digestion).

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi et al., Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (e.g., J. Sambrook et al., "Molecular Cloning: A Laboratory Manual" 1989, 211d Ed., Cold Spring Harbour Laboratory Press: New York) and kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

One or more samples can be from one or more sources. One or more of samples may be from two or more sources. One or more of samples may be from one or more subjects. One or more of samples may be from two or more subjects. One or more of samples may be from the same subject. One or more subjects may be from the same species. One or more subjects may be from different species. The one or more subjects may be healthy. The one or more subjects may be affected by a disease, disorder or condition.

In some embodiments, a sample is a fluid, such as blood, saliva, lymph, urine, cerebrospinal fluid, seminal fluid, sputum, stool, or tissue homogenates.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some embodiments, the polynucleotides are bound to other target molecules such as proteins, enzymes, substrates, antibodies, binding agents, beads, small molecules, peptides, or any other molecule. In some embodiments, the polynucleotides are not bound to a solid support. Nucleic acids can be extracted from a biological sample by a variety of techniques (Sambrook et al., Molecular Cloning: A Laboratory Manual, Third Edition, Cold Spring Harbor, N.Y. (2001)).

In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some embodiments, blood can be collected into an apparatus containing a magnesium chelator including but not limited to EDTA, and is stored at 4° C. Optionally, a calcium chelator, including but not limited to EGTA, can be added.

In some embodiments, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers. In some embodiments, non-nucleic acid materials can be removed from the starting material using enzymatic treatments (such as protease digestion).

A plurality of samples may comprise at least 2, 3, 4, 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more polynucleotides in a first sample may be different from one or more polynucleotides in a second sample. The one or more polynucleotides in a first sample may be different from one or more polynucleotides in a plurality of samples. One or more polynucleotides in a sample can comprise at least about 80%, 85%, 90%, 95%, 96%, 97%, 98%, 99%, or 100% sequence identity. In some embodiments, one or more polynucleotides in a sample can differ by less than about 100, 90, 80, 70, 60, 50, 40, 30, 25, 20, 25, 10, 9, 8, 7, 6, 5, 4, 3, 2, or 1 nucleotide or base pair. A plurality of polynucleotides in one or more samples of the plurality of samples can comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99% or 100% of the total polynucleotides in one or more of the plurality of samples can comprise the same sequence. A plurality of polynucleotides in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the total polynucleotides in one or more of the plurality of samples may comprise at least two different sequences. In some embodiments, one or more polynucleotides are variants of each other. For example, one or more polynucleotides may contain single nucleotide polymorphisms or other types of mutations. In another example, one or more polynucleotides are splice variants.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, e.g., 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or 1 day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 seconds, 45 seconds, 30 seconds, 20 seconds, 10 seconds, 5 seconds, 2 seconds or 1 second of obtaining one or more different samples. One or more samples can be obtained within less than one second of obtaining one or more different samples.

The different polynucleotides of a sample can be present in the sample at different concentrations or amounts (e.g., different number of molecules). For example, the concentration or amount of one polynucleotide can be greater than the concentration or amount of another polynucleotide in the sample. In some embodiments, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one other polynucleotide in the sample. In another example, the concentration or amount of one polynucleotide is less than the concentration or amount of another polynucleotide in the sample. The concentration or amount of at least one polynucleotide in the sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one other polynucleotide in the sample.

In some embodiments, two or more samples may contain different amounts or concentrations of the polynucleotides. In some embodiments, the concentration or amount of one polynucleotide in one sample may be greater than the concentration or amount of the same polynucleotide in a different sample. For example, a blood sample might contain a higher amount of a particular polynucleotide than a urine sample. Alternatively, a single sample can divided into two or more subsamples. The subsamples may contain different amounts or concentrations of the same polynucleotide. The concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of the same polynucleotide in another sample. Alternatively, the concentration or amount of one polynucleotide in one sample may be less than the concentration or amount of the same polynucleotide in a different sample. For example, the concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of the same polynucleotide in another sample.

Target Polynucleotides

In some cases, methods provided herein are directed to amplification and sequencing of a target polynucleotide molecule, such as a polynucleotide molecule from a cell. In some cases, methods provided herein are directed to amplification and sequencing of two or more regions of a target polynucleotide molecule. In some cases, methods provided herein are directed to amplification and sequencing of two or more target polynucleotide molecules. In one aspect, target polynucleotides are RNA. In one aspect, target polynucleotides are genomic nucleic acids. DNA derived from the genetic material in the chromosomes of a particular organism can be genomic DNA. In preferred embodiments, target polynucleotides include sequences comprising variable regions of an antibody or TCR produced by an immune cell. In some embodiments, target polynucleotides include sequences comprising a variable region of a heavy chain of an antibody produced by an immune cell. In some embodiments, target polynucleotides include sequences comprising a variable region of a light chain of an antibody produced by an immune cell. In some embodiments, target polynucleotides include sequences comprising a variable region of an alpha chain of a TCR produced by an immune cell. In some embodiments, target polynucleotides include sequences comprising a variable region of a beta chain of a TCR produced by an immune cell. In some embodiments, target polynucleotides include sequences comprising a variable region of a gamma chain of a TCR produced by an immune cell. In some embodiments, target polynucleotides include sequences comprising a variable region of a delta chain of a TCR produced by an immune cell.

Target polynucleotides can be obtained from virtually any source and can be prepared using methods known in the art. For example, target polynucleotides can be directly isolated without amplification using methods known in the art, including without limitation extracting a fragment of genomic DNA or mRNA from an organism or a cell (e.g., an immune cell) to obtain target polynucleotides. A target polynucleotide can also encompass cDNA generated from RNA (such as mRNA) through reverse transcription-PCR. In some cases, a target polynucleotide is an RNA molecule. In some cases, a target polynucleotide is an mRNA molecule, or a cDNA produced from the mRNA molecule. In some cases, a target polynucleotide is an mRNA molecule, or cDNA molecule produced from the mRNA molecule, from a single immune cell. In some cases, target polynucleotides are mRNA molecules, or cDNA molecules produced from the mRNA molecules, from individual immune cells. In some cases, target polynucleotides are mRNA molecules encoding an antibody sequence from a single immune cell. In some cases, target polynucleotides are mRNA molecules encoding heavy chain antibody sequences from individual immune cells. In some cases, target polynucleotides are mRNA molecules encoding a heavy chain antibody sequence from a single immune cell. In some cases, target polynucleotides are mRNA molecules encoding light chain antibody sequences from individual immune cells. In some cases, target polynucleotides are mRNA molecules encoding a light chain antibody sequence from a single immune cell. In some cases, target polynucleotides are mRNA molecules encoding antibody variable sequences from individual immune cells. In some cases, target polynucleotides are mRNA molecules encoding a variable antibody sequence from a single immune cell. In some cases, target polynucleotides are mRNA molecules encoding variable light chain antibody sequences from individual immune cells. In some cases, target polynucleotides are mRNA molecules encoding a variable light chain antibody sequence from a single immune cell. In some cases, target polynucleotides are mRNA molecules encoding variable heavy chain antibody sequences from individual immune cells. In some cases, target polynucleotides are mRNA molecules encoding a variable heavy chain antibody sequence from a single immune cell. In some cases, a target polynucleotide can be a cell-free nucleic acid, e.g., DNA or RNA. In some cases, target polynucleotides are mRNA molecules encoding variable alpha, beta, gamma, and/or delta chain TCR sequences from individual immune cells.

The methods described herein can be used to generate a library of polynucleotides from one or more target polynucleotides for sequencing. Target polynucleotides include any polynucleotides of interest that are not products of an amplification reaction. For example, a target polynucleotide can include a polynucleotide in a biological sample. For example, target polynucleotides do not include products of a PCR reaction. For example, target polynucleotides may include a polynucleotide template used to generate products of an amplification reaction, but do not include the amplification products themselves. For example, target polynucleotides may include a polynucleotide template used to generate products of a reverse transcription reaction or primer extension reaction, and also include the reverse transcription reaction or primer extension reaction products themselves. For example, target polynucleotides include polynucleotides of interest that can be subjected to a reverse transcription reaction or a primer extension reaction. For example, target polynucleotides include RNA or DNA. For example, target polynucleotides include cDNA. In some embodiments, target RNA polynucleotides are mRNA. In some embodiments, target RNA polynucleotides are polyadenylated. In some embodiments, the RNA polynucleotides are not polyadenylated. In some embodiments, the target polynucleotides are DNA polynucleotides. The DNA polynucleotides may be genomic DNA. The DNA polynucleotides may comprise exons, introns, untranslated regions, or any combination thereof.

In some embodiments, libraries can be generated from two or more regions of a target polynucleotide. In some embodiments, methods libraries can be generated from two or more target polynucleotides. In some embodiments, target polynucleotides are genomic nucleic acids or DNA derived from chromosomes. In some embodiments, target polynucleotides include sequences comprising a variant, such as a polymorphism or mutation. In some embodiments, target polynucleotides include DNA and not RNA. In some embodiments, target polynucleotides include RNA and not DNA. In some embodiments, target polynucleotides include DNA and RNA. In some embodiments, a target polynucleotide is an mRNA molecule. In some embodiments, a target polynucleotide is a DNA molecule. In some embodiments, a target polynucleotide is a single stranded polynucleotide. In some embodiments, a target polynucleotide is a double stranded polynucleotide. In some embodiments, a target polynucleotide is a single strand of a double stranded polynucleotide.

Target polynucleotides can be obtained from any biological sample and prepared using methods known in the art. In some embodiments, target polynucleotides are directly isolated without amplification. Methods for direct isolation are known in the art. Non-limiting examples include extracting genomic DNA or mRNA from a biological sample, organism or, cell.

In some embodiments, one or more target polynucleotides are purified from a biological sample. In some embodiments, a target polynucleotide is not purified from the biological sample in which it is contained. In some embodiments, a target polynucleotide is isolated from a biological sample. In some embodiments, a target polynucleotide is not isolated from the biological sample in which it is contained. In some embodiments, a target polynucleotide can be a cell-free nucleic acid. In some embodiments, a target polynucleotide can be a fragmented nucleic acid. In some embodiments, a target polynucleotide can be a transcribed nucleic acid. In some embodiments, a target polynucleotide is a modified polynucleotide. In some embodiments, a target polynucleotide is a non-modified polynucleotide.

In some embodiments, a target polynucleotide is polynucleotide from a single cell. In some embodiments, target polynucleotides are from individual cells. In some embodiments, a target polynucleotide is polynucleotide from a sample containing a plurality of cells.

In some embodiments, a target polynucleotide encodes a biomarker sequence. In some embodiments, a target polynucleotide encodes two or more biomarker sequences. In some embodiments, a plurality of target polynucleotides encodes a biomarker sequence. In some embodiments, a plurality of target polynucleotides encodes two or more biomarker sequences. In some embodiments, a plurality of target polynucleotides encodes 3, 4, 5, 6, 7, 8, 9, 10, 20, 30, 40, 50, 60, 70, 80, 90, or 100 or more biomarker sequences.

In some embodiments, a plurality of target polynucleotides comprises a panel of immunoglobulin sequences. In some embodiments, a plurality of target polynucleotides comprises a panel of TCR sequences. For example, a panel of immunoglobulin sequences can be $V_H$ and/or $V_L$ sequences. In some embodiments, a panel of immunoglobulin or TCR sequences contains 1, 2, 3, 4, 5, 6, 7, 8, 9, or 10 immunoglobulin or TCR sequences. In some embodiments, a panel of immunoglobulin or TCR sequences contains at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin or TCR sequences. In some embodiments, a panel of immunoglobulin or TCR sequences contains at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin or TCR sequences. In some embodiments, a panel of immunoglobulin or TCR sequences contains from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, 5000-10000, $1\text{-}1\times10^5$, $1\text{-}2\times10^5$, $1\text{-}3\times10^5$, $1\text{-}4\times10^5$, $1\text{-}5\times10^5$, $1\text{-}6\times10^5$, $1\text{-}7\times10^5$, $1\text{-}8\times10^5$, $9\times10^5$, $1\text{-}1\times10^6$, $1\text{-}2\times10^6$, $1\text{-}3\times$ $10^6$, $1\text{-}4\times10^6$, $1\text{-}5\times10^6$, $1\text{-}6\times10^6$, $1\text{-}7\times10^6$, $1\text{-}8\times10^6$, $9\times10^6$, $1\times10^7$, $1\text{-}2\times10^7$, $1\text{-}3\times10^7$, $1\text{-}4\times10^7$, $1\text{-}5\times10^7$, $1\text{-}6\times10^7$, $1\text{-}7\times10^7$, $1\text{-}8\times10^7$, $1\text{-}9\times10^7$, $1\times10^8$, $1\text{-}2\times10^8$, $1\text{-}3\times10^8$, $1\text{-}4\times10^8$, $1\text{-}5\times10^8$, $1\text{-}6\times10^8$, $1\text{-}7\times10^8$, $1\text{-}8\times10^8$, $1\text{-}9\times10^8$, $1\times10^9$, $1\text{-}2\times10^9$, $1\text{-}3\times10^9$, $1\text{-}4\times10^9$, $1\text{-}5\times10^9$, $1\text{-}6\times10^9$, $1\text{-}7\times10^9$, $1\text{-}8\times10^9$, $1\text{-}9\times10^9$, $1\text{-}1\times10^{10}$, $1\text{-}2\times10^{10}$, $1\text{-}3\times10^{10}$, $1\text{-}4\times10^{10}$, $1\text{-}5\times10^{10}$, $1\text{-}6\times10^{10}$, $1\text{-}7\times10^{10}$, $1\text{-}8\times10^{10}$, $1\text{-}9\times10^{10}$, $1\text{-}1\times10^{11}$, $1\text{-}2\times10^{11}$, $1\text{-}3\times10^{11}$, $1\text{-}4\times10^{11}$, $1\text{-}5\times10^{11}$, $1\text{-}6\times10^{11}$, $1\text{-}7\times10^{11}$, $1\text{-}8\times10^{11}$, $1\text{-}9\times10^{11}$, $1\text{-}1\times10^{12}$, $1\text{-}2\times10^{12}$, $1\text{-}3\times10^{12}$, $1\text{-}4\times10^{12}$, $1\text{-}5\times10^{12}$, $1\text{-}6\times10^{12}$, $1\text{-}7\times10^{12}$, $1\text{-}8\times10^{12}$, or $1\text{-}9\times10^{12}$ immunoglobulin or TCR sequences.

In some embodiments, a target polynucleotide is about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, or 5000-10000 bases or base-pairs in length. In some embodiments, the average length of the target polynucleotides, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some embodiments, a target sequence from a relative short template, such as a sample containing a target polynucleotide, is about 40, 45, 50, 55, 60, 65, 70, 75, 80, 85, 90, 95, or 100 bases. In certain embodiments, sequencing data are aligned against known or expected sequences using a database containing sequences or immunoglobulin or TCR sequences associated with a disease or condition.

Immune Repertoire Sequencing

The present invention utilizes steps in which nucleic acids are manipulated in order to generate libraries of polynucleotides for sequencing. In some embodiments, the present invention utilizes steps in which nucleic acids are manipulated in order to produce recombinant monoclonal antibodies. In a general sense, in some embodiments of the invention, amplification of immune cell and/or T cell genetic material, e.g. reverse transcription polymerase chain reaction (reverse transcription-PCR) is employed to generate cDNA amplification of immune cell genetic material. For antibody molecules, the immunoglobulin genes can be obtained from genomic DNA or mRNA of immune cells or T cells. RNA can be heavy chain (V, D, J segments), or light chain (V, J segments). In some embodiments, the starting material is RNA from immune cells composed of V, D, J gene segments that encodes for an antibody, and contains a constant region.

The polynucleotide starting material, such as RNA, can be reverse transcribed into cDNA using one or a pool of polynucleotides. The polynucleotides can comprise a portion complementary to a region of the RNA, such as in a constant region or to a poly-A tail of the mRNA. A vessel barcode, which can be a stretch of ~20 degenerate nucleotide with or without a known intercalating base position, such as NNNNWNNNNWNNNNWNNNNW, where W means A or T (SEQ ID NO: 22).

cDNA resulting from reverse transcription can be tagged with one or more barcodes, for example, with a vessel barcode and a molecular barcode. Various oligonucleotides of particular design can be used for tagging. Tagged cDNA resulting from reverse transcription can be amplified one or more times, such as by PCR amplification. Various primers of particular design can be used for the amplification. A product of a first amplification reaction, such as PCR, can be amplified using a second amplification reaction, such as a first or second PCR phase. Various primers can be used for the amplification step. A library of amplified polynucleotides can be generated using the methods described herein. A resulting library can comprise a full or partial antibody or TCR sequence with appropriate molecular and vessel barcodes.

In other embodiments, template switching can be used to generate libraries, such as for immune repertoire sequencing. For example, template switching can be employed during reverse transcription to generate a region on the product of the reverse transcription that is complementary to a polynucleotide harboring a barcode, such as a vessel barcoded polynucleotide or a molecular barcoded polynucleotide. Template switching can be employed during reverse transcription to remove issues of PCR bias. These methods can be used for antibody sequencing, such as through the use of a high-throughput sequencing platform.

Starting material can be RNA or DNA, such as from immune cells or T-cells comprising the V, D, J gene segments that encode for an antibody, and contains the constant region. In some embodiments, the target polynucleotide comprises heavy chain segments (V, D, J segments), or light chain segments (V, J segments).

Target polynucleotides can be reverse transcribed into cDNA using one or a pool of polynucleotides. Examples of primers in a pool of polynucleotides for reverse transcribing a target polynucleotide can comprise a portion complementary to a region of the target polynucleotide. In some embodiments, the portion complementary to a region of the target polynucleotide can be complementary to a constant region or to a poly-A tail of the target polynucleotide, such as mRNA. Multiple oligonucleotides, such as primers, can be used to anneal one or more constant regions. A reverse transcriptase can be employed to carry out the reverse transcription reaction. In particular embodiments, a reverse transcriptase can comprise a non-template terminal transferase activity. When a reverse transcriptase comprising non-template terminal transferase activity reaches the end of a template, it can add three or more non-template residues, such as three or more non-template cytosine residues. In some embodiments, Superscript II™ reverse transcriptase is used for this purpose. In some embodiments, Maxima™ reverse transcriptase is used for this purpose. In some embodiments, Protoscript II™ reverse transcriptase is used for this purpose. In some embodiments, moloney murine leukemia virus reverse transcriptase (MMLV-RT) is used for this purpose. In some embodiments, HighScriber™ Reverse Transcriptase is used for this purpose. In some embodiments a terminal deoxynucleotidyl transferase is used for this purpose. In some embodiments avian myeloblastosis virus (AMV) reverse transcriptase is used for this purpose. Any reverse transcriptase capable of transcribing RNA that has non-template terminal transferase activity can be used. Any reverse polymerase capable of transcribing RNA that has non-template terminal transferase activity can be used. Any reverse polymerase capable of transcribing DNA that has non-template terminal transferase activity can be used.

Reverse transcription reactions, such as those described above, can be conducted in the presence of a 3' tagging polynucleotide. A 3' tagging polynucleotide can be a polynucleotide used to add nucleic acids to a 3' end of a target polynucleotide, such as a cDNA. A 3' tagging polynucleotide can be a polynucleotide used as a template to add nucleic acids to a 3' end of a target polynucleotide, such as a cDNA. A 3' tagging polynucleotide can be a polynucleotide that hybridizes to a 3' end of a target polynucleotide, such as a cDNA. A 3' tagging polynucleotide can be a polynucleotide that contains a 3' region, such as a 3' terminal region, that hybridizes to a 3' end of a target polynucleotide, such as a cDNA. For example, a 3' tagging polynucleotide can comprise a segment, such as a segment that anneals to three or more non-template residues. In some embodiments, a 3' tagging polynucleotide is a molecular barcode polynucleotide. In some embodiments, a 3' tagging polynucleotide can comprise a molecular barcode. In some embodiments, a 3' tagging polynucleotide can comprise 3 ribo-guanine residues or analogues thereof on the 3' end (rGrGrG) (RNA bases) that are complementary to and annealed to the strand produced by the reverse transcription enzyme. In some embodiments, three or more guanine residues can be used instead of ribo-guanine (DNA nucleotide instead of RNA nucleotide). In some embodiments, a 3' tagging polynucleotide can comprise 1 or 2 ribo-guanine residues on the 3' end and a deoxyribo-guanine residue or analogue thereof on the 3' end (rGrGG) that are complementary to and annealed to the strand produced by the reverse transcription enzyme.

Upon annealing of a 3' tagging polynucleotide to a CCC of the cDNA strand, a reverse transcriptase can continue extending the cDNA into the tagging polynucleotide, thereby attaching a molecular barcode or complement thereof, to a target population of polynucleotides, such as cDNAs, in the reaction. For example, 3' tagging polynucleotide can be a polynucleotide that contains a region 5' to the 3' region that hybridizes to a 3' end of a target polynucleotide. The region 5' to the 3' region that hybridizes to a 3' end of a target polynucleotide can comprise a region that is not complementary to the target polynucleotide, such as a cDNA. The region 5' to the 3' region that hybridizes to a 3' end of a target polynucleotide can comprise a molecular barcode. The region 5' to the 3' region that hybridizes to a 3' end of a target polynucleotide can comprise a region complementary to a vessel barcoded polynucleotide or complement thereof. In other experiments, template switching can be performed in separate reactions. For example, a 3' tagging polynucleotide can be added after the reverse transcription reaction, and enzymes such as a reverse transcriptase or polymerase can be used to extend into a tagging polynucleotide. Because a tagging polynucleotide can harbor a unique degenerate molecular barcode on each molecule in a vessel, each cDNA in a vessel can be uniquely tagged with a molecular barcode. In some embodiments, template switching can be performed at the same time as a reverse transcription reaction is conducted.

In some embodiments, a 3' tagging polynucleotide, such as a molecular barcoded polynucleotide, can further comprise a 5' region, such as a 5' terminal region that is complementary to a 3' tagging polynucleotide or complement thereof containing another barcode, such as a vessel barcode. In some embodiments, a target polynucleotide that contains a molecular barcode or complement thereof, such as a tagged cDNA molecule, can comprise a 3' region, such as a 3' terminal region that is complementary to a 3' tagging polynucleotide or complement thereof containing another barcode, such as a vessel barcode.

In some embodiments, a 3' tagging polynucleotide is a vessel barcoded polynucleotide. Upon generation of a polynucleotide containing a molecular barcode or complement thereof from a target polynucleotide, a vessel barcode can be added to the molecular barcoded target polynucleotide. A 3' tagging polynucleotide can be a polynucleotide used to add nucleic acids to a 3' end of a target polynucleotide, such as a molecular barcoded target polynucleotide. A 3' tagging polynucleotide can be a polynucleotide used as a template to add nucleic acids to a 3' end of a target polynucleotide, such as a molecular barcoded target polynucleotide. A 3' tagging polynucleotide can be a polynucleotide that hybridizes to a 3' end of a target polynucleotide, such as a molecular barcoded target polynucleotide. A 3' tagging polynucleotide can be a polynucleotide that contains a 3' region, such as a 3' terminal region, that hybridizes to a 3' end of a target polynucleotide, such as a molecular barcoded target polynucleotide. A vessel barcoded polynucleotide can comprise a 3' region, such as a 3' terminal region, that hybridizes to a 3' end of a molecular barcoded target polynucleotide.

Upon annealing of a 3' tagging polynucleotide to a molecular barcoded target polynucleotide, a reverse transcriptase can continue extending the cDNA into the 3' tagging polynucleotide, such as a vessel barcoded polynucleotide, thereby attaching a vessel barcode or complement thereof, to a target population of polynucleotides, such as molecular barcoded target polynucleotides, in the reaction. For example, 3' tagging polynucleotide can be a polynucleotide that contains a region 5' to the 3' region that hybridizes to a 3' end of a molecular barcoded target polynucleotide. The region 5' to the 3' region that hybridizes to a 3' end of a molecular barcoded target polynucleotide can comprise a region that is not complementary to the target polynucleotide or the molecular barcoded target polynucleotide. The region 5' to the 3' region that hybridizes to a 3' end of a molecular barcoded target polynucleotide can comprise a vessel barcode.

In some embodiments, a 3' tagging polynucleotide is an amplified product. In some embodiments, a 3' tagging polynucleotide is an amplified product originating from a single molecule. In some embodiments, a 3' tagging polynucleotide is an amplified product of a vessel barcoded polynucleotide. In some embodiments, a 3' tagging polynucleotide is an amplified product originating from a single vessel barcoded polynucleotide. The region 5' to the 3' region that hybridizes to a 3' end of a molecular barcoded target polynucleotide can comprise a region complementary to a primer or complement thereof. The region 5' to the 3' region that hybridizes to a 3' end of a molecular barcoded target polynucleotide can comprise a region complementary to a primer or complement thereof that was used to amplify the vessel barcoded polynucleotide.

A dual barcoded target polynucleotide, such as a cDNA containing a molecular barcode and a vessel barcode can then be amplified, such as by PCR. The PCR can then be conducted, for example, by using a primer set. A product of the aforementioned PCR reaction can then be amplified one or more times, such as by one or more rounds of PCR, or directly sequenced.

A library produced according to the methods described herein can be a library comprising a large or full antibody or TCR sequence with appropriate barcodes, such as vessel barcodes and molecular barcodes, which are sequenced. In some embodiments, a library produced according to the methods described herein can contain appropriate clustering segments for sequencing. In some embodiments, many copies of identical molecular barcodes can be generated. In some embodiments, many copies of polynucleotides containing identical molecular barcodes can be generated for each starting unique target polynucleotide molecule. In some embodiments, many copies of polynucleotides containing identical molecular barcodes can be generated for each starting unique target polynucleotide molecule tagged with a vessel barcode.

Upon sequencing, sequences with identical molecular barcodes can be matched or paired. Upon sequencing, sequences with identical vessel barcodes can be matched or paired. Upon sequencing, sequences with identical target sequences can be matched or paired. In some embodiments, sequencing reads can be collapsed into consensus sequences. Collapsing matched or paired sequencing reads into a consensus sequence can thereby reduce or eliminate sequencing and PCR errors. Sequencing can be performed using a first primer site for a first read. Sequencing can be performed using the first primer site for a second read. Sequencing can be performed using a second primer site for a second read.

Antibody heavy and light chains containing the same vessel barcodes, can be paired, and in some embodiments, cloned in a mammalian vector system. The antibody construct can be expressed in other human or mammalian host cell lines. The construct can then be validated by transient transfection assays and Western blot analysis of the expressed antibody or TCR of interest.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800, 159, 4,965,188, to Mullis, et al.; U.S. Pat. Nos. 4,795,699 and 4,921,794 to Tabor, et al.; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al.; U.S. Pat. No. 4,889,818 to Gelfand, et al.; U.S. Pat. No. 4,994,370 to Silver, et al.; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

Conveniently, the method steps described herein, such as amplification, sequencing, and the like, may or may not be carried out in a multiplex assay format employing a solid phase on which a plurality of substrates, e.g., antigens, and the like, are immobilized, such as an array. In some embodiments, the array is a protein biochip. Using protein biochips, hundreds and even thousands of antigens can be screened. As used herein, "array," "microarray," or "biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes. A "protein biochip" refers to a biochip adapted for the capture of polypeptides. Many protein biochips are described in the art. Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, 1-$V_H$; MacBeath and Schreiber, 2000, Science 289: 1760-1763; WO 01/40803 and WO 99/51773A1. Use of arrays allows a number of the steps, such as screening, to be performed robotically and/or in a high-throughput manner. Polypeptides for the array can be spotted at high speed, e.g., using a commercially available robotic apparatus, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer. Upon capture on a biochip, analytes can be detected by a variety of detection methods selected from, for example, a gas phase ion spectrometry method, an optical method, an electrochemical method, atomic force microscopy and a radio frequency method. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and nonconfocal), imaging methods and non-imaging methods Immunoassays in various formats (e.g., ELISA) are popular methods for detection of analytes captured on a solid phase. Electrochemical methods include voltammetry and amperometry methods. Radio frequency methods include multipolar resonance spectroscopy.

In some embodiments of the invention, e.g., the natural diversity approach for preparing monoclonal antibodies, techniques which have been established for working with single cells are employed. One technique incorporates a special accessory which can be used in FACS to deflect single cells into separate containers. Such accessories are commercially available and well-known in the art. Such accessories are useful for dispensing single cells into selected compartments of, for example, standard 96 well microtiter culture plates. Alternatively, cells may be deposited into a microtiter plate at a limiting dilution to ensure single cell deposition.

A second technique is PCR performed on single immune cells to amplify the $V_H$ and $V_L$ segments. In the natural diversity approach, single cell PCR is used to retain the native pairing of $V_L$ and $V_H$ in the single cell. The specificity of an antibody is determined by the complementarity determining regions (CDRs) within the $V_L$ region and $V_H$ region.

Methods for performing single-cell PCR are well known in the art (e.g., Larrick, J. W. et al., Bio/Technology 7:934 (1989)). For example, antibody-producing B-cells from the B cell library or TCR-producing T-cells from the T-cell library may be fixed with a fixative solution or a solution containing a chemical such as formaldehyde, glutaraldehyde or the like. The cells are then permeabilized with a permeabilization solution comprising for example a detergent. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and $V_L$ or $V\alpha$ and $V\beta$ or $V\gamma$ and $V\delta$ mRNA, for example, into the corresponding cDNA sequences. Reverse transcription may be performed in a single step or optionally together with a PCR procedure, using a reverse transcriptase, sufficient quantities of the four dNTPs, and primers that bind to the mRNA providing a 3' hydroxyl group for reverse transcriptase to initiate polymerization. Any primer complementary to the mRNA may be used, but it is preferred to use primers complementary to a 3'-terminal end of the $V_H$ and $V_L$ or $V\alpha$ and $V\beta$ or $V\gamma$ and $V\delta$ molecules so as to facilitate selection of variable region mRNA. Numerous studies have indicated that degenerate polynucleotides can be prepared to serve as the 5'-end primers for $V_H$ and $V_L$ or $V\alpha$ and $V\beta$ or $V\gamma$ and V. The combinatorial library method of making targeting molecules relies on such primers. Furthermore, numerous experiments have shown that PCR can amplify the gene segments of interest, such as $V_H$ and $V_L$ or $V\alpha$ and $V\beta$ or $V\gamma$ and $V\delta$, from a single cell. Because of the ability to work with even a single cell, this PCR approach can generate antibodies even where the immune cells of interest occur at low frequency.

In the high diversity embodiment, after FACS sorting, the cells of immune cell library are pooled and the reverse transcription-PCR is performed on the entire pool of cells. Generation of mRNA for cloning antibody or TCR purposes is readily accomplished by well-known procedures for preparation and characterization of antibodies or TCRs (see, e.g., Antibodies: A Laboratory Manual, 1988; incorporated herein by reference). For example, total RNA from the B-cell library is extracted by appropriate methods which are standard and conventional in the art. cDNA is then synthesized from the RNA by appropriate methods, e.g. using random hexamer polynucleotides, or C-gene or C-gene family-specific primers, or V-gene or V-gene family-specific primers. Again these are processes known to persons skilled in the art as explained above. Libraries of nucleic acid molecules derived from B-cell or T-cell libraries, e.g. a library of RNA or cDNA molecules derived from such B or T lymphocytes, may be cloned into expression vectors to form expression libraries. In some embodiments, only the $V_H$ or $V\alpha$ or $V\gamma$ domain derived from the immune cell library is amplified to generate a library of $V_H$ or $V\alpha$ or $V\gamma$ domains. A $V_L$ or $V\beta$ or $V\delta$ library from another source is used in combination with the $V_H$ or $V\alpha$ or $V\gamma$ library to generate antibodies or TCRs using methods described herein. Libraries of antibody or TCR fragments can be constructed by combining $V_H$ and $V_L$ or $V\alpha$ and $V\beta$ or $V\gamma$ and $V\delta$ libraries together in any number of ways as known to the skilled artisan. For example, each library can be created in different vectors, and the vectors recombined in vitro, or in vivo. Alternatively, the libraries may be cloned sequentially into the same vector, or assembled together by PCR and then cloned. PCR assembly can also be used to join $V_H$ and $V_L$ or $V\alpha$ and $V\beta$ or $V\gamma$ and $V\delta$ DNAs with DNA encoding a flexible peptide spacer to form single chain Fv (scFv) libraries as described elsewhere herein. In yet another technique, in-cell PCR assembly is used to combine $V_H$ and $V_L$ or $V\alpha$ and $V\beta$ or $V\gamma$ and $V\delta$ genes within lymphocytes by PCR and then clone repertoires of linked genes.

Single Cell Barcoding

For single cell barcoding with a vessel barcode and molecular barcode, vessels, such as water in oil emulsions, can be created in such way that resulting vessels contain 1 cell or less per vessel. The vessels can be created in such way that resulting vessels also contain 1 vessel barcode per vessel. The vessels can be created in such way that resulting vessels also contain 1 molecular barcoded polynucleotide per vessel. The vessels can be created in such way that resulting vessels also contain two or more, or a plurality of, molecular barcoded polynucleotides per vessel. The cells/vessels can be subject to an RNA or DNA single barcoding protocol as described herein, and the vessel barcode and one or more molecular barcode of each vessel can be fused with a target of interest, such as a cell polynucleotide. In some embodiments, matching vessel barcoded polynucleotides can be fused to cell components present in the same vessel as the one or more molecular barcoded polynucleotides. Following sequencing, vessel barcode and molecular barcode deconvolution can be used to identify which RNA (or DNA) originated from which cell. In some embodiments, vessels, such as water in oil emulsions, can be created in such way that resulting emulsions contained 1 cell or more per emulsion. In some embodiments, water in oil emulsions can be created in such way that resulting emulsions contain 1 vessel barcoded polynucleotide and two or more molecular barcoded polynucleotides per vessel. In some embodiments, vessels can be created in such way that resulting vessels contain more than 1 vessel barcoded polynucleotide and two or more molecular barcoded polynucleotides per vessel. In some embodiments, a vessel barcode and molecular barcode can be introduced into vessels when in solution. In some embodiments, a vessel barcode and molecular barcode can be introduced into vessels when not attached to a solid support, such as a bead.

In some aspects, single cells can be isolated inside an emulsion, which can act as a compartment. The cells can be lysed and transcripts from the cell can be barcoded. Each of the transcripts can be fused with a molecular barcode or vessel barcode, in such way that when two or more RNA transcripts are detected with the same vessel barcode, they can be determined to have originated from the same starting cell. This can be applied to many different types of sequences. One particular application can be linking $V_H$ and $V_L$ or $V\alpha$ and $V\beta$ or $V\gamma$ and $V\delta$ chains of antibody and TCR sequences.

One or more single cells can be isolated in one or more emulsions, in the presence of a vessel barcode and molecular barcodes, so that one droplet of the one or more emulsions can contain a maximum of 1 cell or less. Cells can be lysed chemically by a buffer contained in an emulsion or by freeze thaw, thereby releasing the contents of a cell in an emulsion.

RNAs of a single cell can be reverse transcribed into cDNA. A reverse transcription reaction can be done with a reverse transcriptase that possesses non-template terminal transferase activity which adds about 3 cytosine residues as described above. All reverse transcription buffers, enzymes, and nucleotides can be present when forming an emulsion. In some embodiments, a primer can be generalized (such as polynucleotide comprising a poly dT sequence) to target all mRNA. In some embodiments, DNA can be used. In some embodiments, more than 2 RNAs can be targeted.

In some embodiments, a vessel barcode can be linked to a RNA during reverse transcription. In some embodiments, a molecular barcode can be linked to a RNA during reverse transcription. In some embodiments, a vessel barcode and molecular barcode can be linked to a RNA during reverse transcription.

A reverse transcription reaction can be conducted in a presence of a 3' tagging polynucleotide. A 3' tagging polynucleotide can comprise a P7 segment which can be used for annealing a sequencing primer. A 3' tagging polynucleotide can comprise a vessel barcode or a molecular barcode. A 3' tagging polynucleotide can comprise 3 ribo-guanine residues on a 3' end (rGrGrG) (RNA bases) that can be complementary to and annealed to a strand produced by a reverse transcription enzyme. Thus, a vessel barcode and molecular barcode can be added to a terminal end of a cDNA in this same emulsion by reverse transcription enzymes. In some embodiments, guanine residues can be used instead of ribo-guanine (DNA nucleotide instead of RNA nucleotide). Upon annealing of a 3' tagging polynucleotide to a CCC of a cDNA strand, a reverse transcriptase continues extending a cDNA into a 3' tagging polynucleotide, thereby creating a molecular barcoded tag to all cDNAs in a reaction. Upon annealing of a 3' tagging polynucleotide to a region of a molecular barcoded cDNA, a reverse transcriptase or polymerase continues extending a molecular barcoded cDNA into another 3' tagging polynucleotide, thereby creating a vessel barcoded tag to all cDNAs in a reaction. In some embodiments, template switching can be done in a separate reaction instead of being done at the same time a reverse transcription reaction can be conducted. In some embodiments, a 3' tagging polynucleotide can be added after a reverse transcription reaction, and enzymes such as a reverse transcriptase or polymerase can be used to extend into a tagging polynucleotide in a similar fashion. Because a 3' tagging polynucleotide can harbor a unique degenerate molecular barcode on each single molecule, each cDNA can be uniquely tagged with a molecular barcode. Because a 3' tagging polynucleotide can harbor a same degenerate vessel barcode on each single molecule from a single vessel, each cDNA can be tagged with a vessel barcode unique to the vessel.

Cloning and Expression of B-Cell Library Genetic Material

"Antibody expression library" or "TCR expression library" or "expression library" as used herein can refer to a collection of molecules (i.e. two or more molecules) at either the nucleic acid or protein level. Thus, this term can refer to a collection of expression vectors which encode a plurality of antibody pr TCR molecules (i.e. at the nucleic acid level) or can refer to a collection of antibody or TCR molecules after they have been expressed in an appropriate expression system (i.e. at the protein level). Alternatively the expression vectors/expression library may be contained in suitable host cells in which they can be expressed. The antibody molecules which are encoded or expressed in the expression libraries of the invention can be in any appropriate format, e.g., may be whole antibody or TCR molecules or may be antibody or TCR fragments, e.g., single chain antibodies (e.g. scFv antibodies), Fv antibodies, Fab' antibodies, (Fab')$_2$ fragments, diabodies, etc. The terms "encoding" and "coding for" as is nucleic acid sequence "encoding"/"coding for" or a DNA coding sequence of or a nucleotide sequence "encoding"/"coding for" a particular enzyme, as well as other synonymous terms, refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence includes the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promoter sequence will be found a transcription initiation site (conveniently defined by mapping with nuclease S1) as well as protein binding domains (consensus sequences) responsible for the binding of RNA polymerase.

Antibody or TCR molecules identified by, derived from, selected from, or obtainable from the antibody or TCR expression libraries of the invention form a yet further aspect of the invention. Again these antibody or TCR molecules may be proteins or nucleic acids encoding antibody or TCR molecules, which nucleic acids may in turn be incorporated into an appropriate expression vector and/or be contained in a suitable host cell.

The cDNA pool can be subjected to a PCR reaction with polynucleotides that hybridize to a constant region of the heavy chain of antibody genes and polynucleotides that hybridize to the 5' end of the $V_H$ or Vα or Vγ chain region of antibody or TCR genes. The cDNA pool can be subjected to a PCR reaction with polynucleotides that hybridize to a constant region of the heavy chain or alpha or gamma chain of antibody or TCR genes and polynucleotides that hybridize to region 5' to the 5' end of the $V_H$ or Vα or Vγ chain region of a barcoded polynucleotide comprising an antibody or TCRδ sequence. A PCR reaction is can also set up for the amplification of the $V_L$ or Vβ or Vδ chain pool of e.g., kappa and lambda classes. The cDNA pool can be subjected to a PCR reaction with polynucleotides that hybridize to a constant region of the light chain of antibody genes and polynucleotides that hybridize to the 5' end of the $V_L$ or Vβ or Vδ chain region of antibody or TCR genes. The cDNA pool can be subjected to a PCR reaction with polynucleotides that hybridize to a constant region of the light chain of antibody genes and polynucleotides that hybridize to region 5' to the 5' end of the $V_L$ or Vβ or Vδ chain region of a barcoded polynucleotide comprising an antibody or TCRδ sequence. Such oligonucleotides or primers may be designed based on known and publicly available immunoglobulin or TCR gene sequence database information.

In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using one or more primers that are not specific for heavy or light chain genes and, in particular, for one or both the terminal regions of the $V_H$ and $V_L$ or Vα and Vβ or Vγ and Vδ polynucleotides. In some embodiments, $V_H$ and $V_L$ sequences can be conveniently obtained from a library of $V_H$ and $V_L$ or Vα and Vβ or Vγ and Vδ sequences produced by PCR amplification using primers specific to a region of the vessel barcoded polynucleotide. In some embodiments, $V_H$ and $V_L$ sequences can be conveniently obtained from a library of $V_H$ and $V_L$ or Vα and Vβ or Vγ and Vδ sequences produced by PCR amplification using C-gene family-specific primers or C-gene-specific primers. In some embodiments, $V_H$ and $V_L$ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer or plurality of second primers that are C-gene family-specific primers or C-gene-specific primers. In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer specific to a universal sequence.

In some embodiments, upon reverse transcription, the resulting cDNA sequences may be amplified by PCR using one or more primers specific for immunoglobulin genes and, in particular, for one or both the terminal regions of the $V_H$ and $V_L$ or Vα and Vβ or Vγ and Vδ polynucleotides. In some embodiments, $V_H$ and $V_L$ sequences can be obtained from a library of $V_H$ and $V_L$ or Vα and Vβ or Vγ and Vδ sequences produced by PCR amplification using V-gene family-specific primers or V-gene-specific primers (Nicholls et al., J. Immunol. Meth., 1993, 165:81; WO93/12227) or are designed according to standard art-known methods based on available sequence information. (The $V_H$ and $V_L$ or Vα and Vβ or Vγ and Vδ sequences can be ligated, usually with an intervening spacer sequence (e.g., encoding an in-frame flexible peptide spacer), forming a cassette encoding a single-chain antibody). V region sequences can be conveniently cloned as cDNAs or PCR amplification products for immunoglobulin-express sing cells. The $V_H$ and $V_L$ or Vα and Vβ or Vγ and Vδ regions are sequenced, optionally, in the methods described herein and particularly after certain steps as noted (e.g., after single cell PCR; after mammalian or other cell surface display, after FACS screening, and the like). Sequencing can be used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments, it is unnecessary to physically link the natural $V_H$ and $V_L$ or Vα and Vβ or Vγ and Vδ combinations using the methods described herein. In some embodiments, cDNAs, barcoded polynucleotides, or PCR amplified barcoded cDNAs are not physically linked. In some embodiments, cDNAs, barcoded polynucleotides, or PCR amplified barcoded cDNAs are not physically linked in the same reaction or vessel.

In some embodiments, the natural $V_H$ and $V_L$ or Vα and Vβ or Vγ and Vδ combinations are physically linked, using, in addition to the cDNA primers, one primer or plurality of primers for the 5' end of the $V_H$ or Vα or Vγ gene and another primer or plurality of primers for the 5' end of the $V_L$ or Vβ or Vδ gene. These primers also contain complementary tails of extra sequence, to allow the self-assembly of the $V_H$ and $V_L$ or Vα and Vβ or Vγ and Vδ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

In some embodiments in which it is desired to provide additional $V_H$ and $V_L$ or Vα and Vβ or Vγ and Vδ combinations, an expression system is chosen to facilitate this. For example, bacteriophage expression systems allow for the random recombination of heavy- and light-chain sequences. Other suitable expression systems are known to those skilled in the art.

It should be noted that in the case of $V_H$ and $V_L$ or Vα and Vβ or Vγ and Vδ sequences derived from nonhumans, in some embodiments, it can be preferable to chimerize these sequences with a fully human Fc. As used herein "chimerized" refers to an immunoglobulin or TCR, wherein the heavy and light chain variable regions or Vα and Vβ or Vγ and Vδ regions are not of human origin and wherein the constant regions of the heavy and light chains or Vα and Vβ or Vγ and Vδ chains are of human origin. This is affected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies or TCRs are characterized, by either sequencing followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, polynucleotides can be designed which will allow the cloning of one or more of the other forms of immunoglobulin molecules, e.g., IgM, IgA, IgE and IgD if desired or appropriate.

Once an antibody or TCR has been identified and the appropriate population of said cells have been isolated at an appropriate time and optionally enriched as described above, the antibody or TCR expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus the above defined method of the invention may comprise the further steps of expressing the library of expression vectors in an appropriate expression system and screening the expressed library for antibodies with desired properties, as explained in further detail below.

As indicated herein, polynucleotides prepared by the methods of the disclosure which comprise a polynucleotide encoding antibody or TCR sequences can include, but are not limited to, those encoding the amino acid sequence of an antibody or TCR fragment, by itself, the noncoding sequence for the entire antibody or TCR or a portion thereof, the coding sequence for an antibody or TCR, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, nontranslated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody or TCR comprising an antibody or TCR fragment or portion.

The primary PCR products can then optionally be subjected to a secondary PCR reaction with new polynucleotide sets that hybridize to the 5' and 3' ends of the antibody or TCR variable domains $V_H$, $V_L$ kappa and $V_L$ lambda or Vα and Vβ or Vγ and Vδ (as appropriate depending on whether the primary PCR reaction with which the new polynucleotide sets are used was designed to amplify portions of the heavy or light chain antibody genes or Vα or Vβ TCR genes or Vγ or Vδ TCR genes). These polynucleotides advantageously include DNA sequences specific for a defined set of restriction enzymes (i.e. restriction enzyme sites) for subsequent cloning. The selected restriction enzymes must be selected so as not to cut within human antibody or TCR V-gene segments. Such polynucleotides may be designed based on known and publicly available immunoglobulin or TCR gene sequence and restriction enzyme database information. However, preferred restriction enzyme sites to be included are NcoI, Hind III, MluI and NotI. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the $V_H$ and $V_L$ or Vα and Vβ or Vγ and Vδ domains of an antibody or TCR are present.

PCR products can also be subjected to a PCR reaction with new primer sets that hybridize to the 5' and 3' ends of the barcoded polynucleotides. These polynucleotides can advantageously include DNA sequences specific for a defined set of restriction enzymes (i.e. restriction enzyme sites) for subsequent cloning. The selected restriction enzymes must be selected so as not to cut within human antibody or TCR V-gene segments. Such polynucleotides may be designed based on known and publicly available immunoglobulin or TCR gene sequence and restriction enzyme database information. However, preferred restriction enzyme sites to be included are NcoI, Hind III, MluI and NotI. The products of such secondary PCR reactions are repertoires of various $V_H$, $V_L$ kappa and $V_L$ lambda antibody fragments/domains or Vα and Vβ or Vγ and Vδ TCR fragments/domains.

One of skill in the art will recognize that heavy or light chain or Vα or Vβ chain or Vγ or Vδ chain Fv or Fab fragments, or single-chain antibodies or TCRs may also be used with this system. A heavy or light chain or Vα or Vβ chain or Vγ or Vδ chain can be mutagenized followed by the addition of the complementary chain to the solution. The two chains are then allowed to combine and form a functional antibody fragment. Addition of random non-specific light or heavy chain or Vα or Vβ chain or Vγ or Vδ chain sequences allows for the production of a combinatorial system to generate a library of diverse members.

Libraries of such repertoires of cloned fragments comprising the variable heavy chain or Vα chain or Vγ chain regions, or fragments thereof, and/or variable light chain or Vβ chain or Vδ chain regions, or fragments thereof, of antibody or TCR genes derived from the B of T lymphocytes of immuno-challenged hosts as defined herein form further aspects of the invention. These libraries comprising cloned variable regions may optionally be inserted into expression vectors to form expression libraries.

In some embodiments, the PCR reactions can be set up so as to retain all or part of the constant regions of the various antibody or TCR chains contained in the isolated immune cell population. This is desirable when the expression library format is a Fab format, wherein the heavy or alpha or gamma chain component comprises $V_H$ or Vα or Vγ and $C_H$ or Cα or Cγ domains and the light chain or Vβ chain or Vδ chain component comprises $V_L$ or Vβ or Vδ chain and $C_L$ or Cβ or Cδ domains. Again, libraries of such cloned fragments comprising all or part of the constant regions of antibody or TCR chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence (SEQ ID NO: 23) provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

The libraries disclosed herein may be used in a variety of applications. As used herein, a library comprises a plurality of molecules. In some embodiments, a library comprises a plurality of polynucleotides. In some embodiments, a library comprises a plurality of primers. In some embodiments, a library comprises a plurality of sequence reads from one or more polynucleotides, amplicons, or amplicon sets. A library can be stored and used multiple times to generate samples for analysis. Some applications include, for example, genotyping polymorphisms, studying RNA processing, and selecting clonal representatives to do sequencing according to the methods provided herein. Libraries comprising a plurality of polynucleotides, such as primers or libraries for sequencing or amplification, can be generated, wherein a plurality of polynucleotides comprises at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more molecular barcodes or vessel barcodes. In some embodiments, libraries of polynucleotides comprise a plurality of at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more unique polynucleotides, wherein each unique polynucleotide comprises one or more molecular barcodes and vessel barcodes.

Barcodes

A barcode can be a molecular barcode or a vessel barcode. In some embodiments, a barcode, such as a molecular barcode or a vessel barcode, can each have a length within a range of from 2 to 36 nucleotides, 4 to 36 nucleotides, or from 6 to 30 nucleotides, or from 8 to 20 nucleotides, 2 to 20 nucleotides, 4 to 20 nucleotides, or from 6 to 20 nucleotides. In certain aspects, the melting temperatures of barcodes within a set are within 10° C. of one another, within 5° C. of one another, or within 2° C. of one another. In certain aspects, the melting temperatures of barcodes within a set are not within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, a molecular barcode comprises information that is unique to a single molecule from a single cell or from a single vessel, or two or more molecules of a plurality or library of molecules from two or more single cells or from two or more single vessels. As used herein, a vessel barcode comprises information that is unique to polynucleotides from a single cell or from a single vessel, compared to polynucleotides from a different single cell or from a different single vessel. In some embodiments the unique information comprises a unique sequence of nucleotides. For example, the sequence of the molecular barcode or a vessel barcode can be determined by determining the identity and order of the unique or random sequence of nucleotides comprising the molecular barcode or a vessel barcode. In some embodiments the unique information cannot be used to identify the sequence of a target polynucleotide. For example, a molecular barcode may be attached to one target polynucleotide, but the molecular barcode cannot be used to determine the target polynucleotide to which it is attached. In some embodiments the unique information is not a known sequence linked to the identity of the sequence of a target polynucleotide. For example, a vessel barcode may be attached to one or more target polynucleotides, but the vessel barcode cannot be used to determine which of the one or more target polynucleotides to which it is attached. In some embodiments, the unique information comprises a random sequence of nucleotides. In some embodiments the unique information comprises one or more unique sequences of nucleotides on a polynucleotide. In some embodiments the unique information comprises a degenerate nucleotide sequence or degenerate barcode. A degenerate barcode can comprise a variable nucleotide base composition or sequence. For example, a degenerate bar code can be a random sequence. In some embodiments, a complement sequence of a molecular barcode or a vessel barcode is also a molecular barcode or a vessel barcode sequence.

A molecular barcode or vessel barcode can comprise any length of nucleotides. For example a molecular barcode or a vessel barcode can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a molecular barcode or a vessel barcode can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some embodiments, a molecular barcode or a vessel barcode has a particular length of nucleotides. For example, a molecular barcode or a vessel barcode can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some embodiments, each molecular barcode or a vessel barcode in a plurality of molecular barcodes or vessel barcodes has at least about 2 nucleotides. For example, each molecular barcode or a vessel barcode in a plurality of molecular barcodes or vessel barcodes can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each molecular barcode or a vessel barcode in a plurality of molecular barcodes or vessel barcodes has at most about 1000 nucleotides. For example, each molecular barcode or a vessel barcode in a plurality of molecular barcodes or vessel barcodes can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each molecular barcode or a vessel barcode in a plurality of molecular barcodes or vessel barcodes has the same length of nucleotides. For example, each molecular barcode or a vessel barcode in a plurality of molecular barcodes or vessel barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, one or more molecular barcodes or vessel barcodes in a plurality of molecular barcodes or vessel barcodes have a different length of nucleotides. For example one or more first molecular barcodes or vessel barcodes in a plurality of molecular barcodes or vessel barcodes can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second molecular barcodes or vessel barcodes in a plurality of molecular barcodes or vessel barcodes can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first molecular barcodes or vessel barcodes is different than the one or more second molecular barcodes or vessel barcodes.

The number of molecular barcodes can be in excess of the total number of molecules to be labeled in a plurality of vessels. The number of vessel barcodes can be in excess of the total number of molecules to be labeled in a plurality of vessels. For example, the number of molecular barcodes or vessel barcodes can be at least about 2, 3, 4, 5, 6, 7, 8, 9, 10, 15, 20, 30, 40, 50, 60, 70, 80, 90, or 100 times greater than the total number of molecules to be labeled in a plurality of vessels.

The number of different molecular barcodes can be in excess of the total number of molecules to be labeled in a plurality of vessels. In some embodiments, the number of different molecular barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the total number of molecules to be labeled in a plurality of vessels.

The number of different molecular barcodes in a single vessel can be in excess of the number of different molecules to be labeled in the single vessel. In some embodiments, the number of different molecular barcodes in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of different vessel barcodes can be less than the total number of molecules to be labeled in a plurality of vessels. In some embodiments, the number of different vessel barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times less than the total number of molecules to be labeled in a plurality of vessels.

The number of amplified product molecules from a vessel barcoded polynucleotide molecule in a single vessel can be in excess of the number of different molecules to be labeled in the single vessel. In some embodiments, the number of amplified product molecules from a vessel barcoded polynucleotide molecule in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of vessel barcoded polynucleotide molecules in a single vessel can be less than the number of different molecules to be labeled in the single vessel. In some embodiments, the number of vessel barcoded polynucleotide molecules in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times less than the number of different molecules to be labeled in the single vessel.

The number of vessel barcoded polynucleotide molecules in a single vessel can be one molecule. The number of unamplified vessel barcoded polynucleotide molecules in a single vessel can be one molecule.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have the same concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have the same concentration.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have a different concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have a different concentration.

The molecular barcodes or vessel barcodes in a population of molecular barcodes or vessel barcodes can have at least 10, 15, 20, 25, 30, 35, 40, 45, 50, 60, 70, 80, 90, 100, 200, 300, 400, 500, 600, 700, 800, 900, 1000 or more different sequences. For example, the molecular barcodes or vessel barcodes in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, 1,000,000 or more different sequences. Thus, a plurality of molecular barcodes or vessel barcodes can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as target polynucleotides. For example, a plurality of molecular barcodes or vessel barcodes can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from one or more polynucleotides, such as target polynucleotides. For example, a plurality of molecular barcodes or vessel barcodes can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{1}$), $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more target polynucleotides.

In some embodiments, one or more molecular barcodes are used to group or bin sequences. In some embodiments, one or more molecular barcodes are used to group or bin sequences, wherein the sequences in each bin contain the same molecular barcode. In some embodiments, one or more molecular barcodes or vessel barcodes are used to group or bin sequences, wherein the sequences in each bin comprise an amplicon set. In some embodiments, one or more molecular barcodes are used to group or bin sequences, wherein the sequences in each bin comprise a plurality of sequences wherein the polynucleotides from which the plurality of sequences were generated were derived from the same polynucleotide molecule in an amplification reaction.

In some embodiments, one or more vessel barcodes are used to group or bin sequences. In some embodiments, one or more vessel barcodes are used to group or bin sequences, wherein the sequences in each bin contain the same vessel barcode. In some embodiments, one or more vessel barcodes are used to group or bin sequences, wherein the sequences in each bin comprise one or more amplicon sets. In some embodiments, one or more vessel barcodes are used to group or bin sequences, wherein the sequences in each bin comprise a plurality of sequences wherein the polynucleotides from which the plurality of sequences were generated were derived from the polynucleotides from a single vessel or single cell.

In some embodiments, one or more molecular barcodes and vessel barcodes are used to group or bin sequences. In some embodiments, one or more molecular barcodes and vessel barcodes are used to group or bin sequences, wherein the sequences in each bin contain the same molecular barcode and same vessel barcode. In some embodiments, one or more molecular barcodes and vessel barcodes are used to group or bin sequences, wherein the sequences in each bin comprise one or more amplicon sets. In some embodiments, one or more molecular barcodes and vessel barcodes are used to group or bin sequences, wherein the sequences in each bin comprise a plurality of sequences wherein the polynucleotides from which the plurality of sequences were generated were derived from the same polynucleotide in an amplification reaction and from the same single cell or vessel. In some embodiments, one or more molecular barcodes and vessel barcodes are not used to align sequences.

In some embodiments, one or more molecular barcodes are not used to align sequences. In some embodiments, one or more molecular barcodes are used to align sequences. In some embodiments, one or more molecular barcodes are used to group or bin sequences, and a target specific region is used to align sequences. In some embodiments, one or more vessel barcodes are not used to align sequences. In some embodiments, one or more vessel barcodes are used to align sequences. In some embodiments, one or more vessel barcodes are used to group or bin sequences, and a target specific region is used to align sequences. In some embodiments, one or more molecular barcodes and vessel barcodes are used to align sequences. In some embodiments, one or more molecular barcodes and vessel barcodes are used to group or bin sequences, and a target specific region is used to align sequences.

In some embodiments, the aligned sequences contain the same molecular barcode. In some embodiments, the aligned sequences contain the same vessel barcode. In some embodiments, the aligned sequences contain the same molecular barcode and vessel barcode. In some embodiments, one or more molecular barcodes or vessel barcodes are used align sequences, wherein the aligned sequences comprise two or more sequences from an amplicon set. In some embodiments, one or more molecular barcodes or vessel barcodes are used to align sequences, wherein the aligned sequences comprise a plurality of sequences wherein the polynucleotides from which the plurality of sequences were generated were derived from the same polynucleotide molecule in an amplification reaction. In some embodiments, one or more molecular barcodes or vessel barcodes are used to align sequences, wherein the aligned sequences comprise a plurality of sequences wherein the polynucleotides from which the plurality of sequences were generated were derived from a single cell or single vessel.

Droplet Generation

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as biomarker sequences.

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as sequences representing a percentage of the transcriptome of an organism. For example, a repertoire of sequences can comprise a plurality of sequences representing at least about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, 10%, 15%, 20%, 30%, 35%, 40%, 45, 50%, 55%, 60%, 65%, 70%, 75%, 80%, 85%, 90%, 95%, 98%, 99%, or 100% of the transcriptome of an organism.

Splitting a sample of immune cells into small reaction volumes, coupled with molecular and vessel barcoding of polynucleotides from, or derived from, an individual immune cell from the plurality of immune cells can enable high throughput sequencing of a repertoire of heavy and light chain sequences. These methods can also allow for pairing of the heavy and light chains after sequencing based on the barcoded sequences. Splitting a sample into small reaction volumes as described herein can also enable the use of reduced amounts of reagents, thereby lowering the material cost of the analysis.

In some cases, the reverse transcription reaction and/or the amplification reaction (e.g., PCR) are carried out in droplets, such as in droplet digital PCR. In certain aspects, the invention provides fluidic compartments to contain all or a portion of a target material. In some embodiments, a compartment is droplet. While reference is made to "droplets" throughout the specification, that term is used interchangeably with fluid compartment and fluid partition unless otherwise indicated. Except where indicated otherwise, "droplet" is used for convenience and any fluid partition or compartment may be used. The droplets used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing an amplification reaction, including cells, nucleotides, nucleotide analogues, molecular barcoded polynucleotides, vessel barcoded polynucleotides primers, template nucleic acids, and enzymes, such as a DNA polymerase, RNA polymerase, and/or reverse transcriptase.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, and dTTP, in concentrations of about, more than about, or less than about 50, 100, 200, 300, 400, 500, 600, or 700 µm each. In some cases dUTP is added within the aqueous phase to a concentration of about, more than about, or less than about 50, 100, 200, 300, 400, 500, 600, or 700, 800, 900, or 1000 µm. In some cases, magnesium chloride or magnesium acetate ($MgCl_2$) is added to the aqueous phase at a concentration of about, more than about, or less than about 1.0, 2.0, 3.0, 4.0, or 5.0 mM. The concentration of $MgCl_2$ can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µm. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µm. The concentration of primers can be about 0.5 µm. Amenable ranges for target nucleic acid concentrations in PCR include, but are not limited to between about 1 pg and about 500 ng.

In some cases, the aqueous phase can also comprise additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). Other additives can include, e.g., dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer can be added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, and Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50° C., 60° C., 70° C., 80° C., 90° C., or 95° C. In some cases this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3° C., 4° C., 5° C., 6° C., 7° C., 8° C., 9° C., 10° C., 15° C., 20° C., 25° C., 30° C., 35° C., or 40° C. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a reverse transcription, primer extension, and/or PCR reaction to occur, e.g., primers, probes, dNTPs, DNA or RNA polymerases, etc. These capsules exhibit resistance to coalescence and flocculation across a wide range of thermal and mechanical processing.

In some cases, the amplifying step is carried out by performing digital PCR, such as microfluidic-based digital PCR or droplet digital PCR.

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

A droplet generally includes an amount of a first sample fluid in a second carrier fluid. Any technique known in the art for forming droplets may be used with methods of the invention. An exemplary method involves flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant.

The same method may be applied to create individual droplets that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxynucleotide triphosphates (dNTPs), and one or more buffers.

In certain embodiments, fluidic compartments are formed by providing a first fluid partition (e.g., a droplet) comprising a target material (e.g., an immune cell and/or a solid support such as a bead) and a second fluid (e.g., as a fluid stream or within droplets). The first and second fluids are merged to form a droplet. Merging can be accomplished by application of an electric field to the two fluids. In certain embodiments, the second fluid contains reagents for conducting an amplification reaction, such as a polymerase chain reaction or a amplification reaction.

In certain aspects, the invention provides a method of making a library of uniquely barcoded heavy and light chain antibody sequences and/or alpha and beta chain TCR sequences and/or gamma and delta chain TCR sequences including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional construct to each compartment in a set, and repeating that for each set to produce N×M compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

Droplet Libraries

In general, a droplet library is made up of a number of library elements that are pooled together in a single collection. Libraries may vary in complexity from a single library element to $1 \times 10^{15}$ library elements or more. Each library element is one or more given components at a fixed concentration. The element may be, but is not limited to, cells, beads, amino acids, proteins, polypeptides, nucleic acids, polynucleotides or small molecule chemical compounds. The element may contain an identifier such as a molecular barcode, a vessel barcode, or both.

A cell library element can include, but is not limited to, hybridomas, B-cells, T-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8):1262-1264, 2008. The discreet nature of cells allows for libraries to be prepared in mass with a plurality of cell variants, such as immune cells producing one antibody or TCR each, all present in a single starting media and then that media is broken up into individual droplet capsules that contain at most one cell. The cells within the individual droplets capsules are then lysed, heavy chain and light chain polynucleotides and/or alpha and beta chain polynucleotides and/or gamma and delta chain polynucleotides from the lysed cells are barcoded with molecular barcodes and vessel barcodes and amplified and then combined or pooled to form a library consisting of heavy and light chain and/or alpha and beta chain and/or gamma and delta chain library elements.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids. It is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

In some embodiments, it is desirable to have exactly one vessel barcoded polynucleotide per droplet with only a few droplets containing more than one vessel barcoded polynucleotide when starting with a plurality of vessel barcoded polynucleotide. In some cases, variations from Poisson statistics can be achieved to provide an enhanced loading of droplets such that there are more droplets with exactly one vessel barcoded polynucleotide per droplet and few exceptions of empty droplets or droplets containing more than one vessel barcoded polynucleotide.

Examples of droplet libraries are collections of droplets that have different contents, ranging from beads, cells, small molecules, DNA, primers, antibodies, and barcoded polynucleotides. The droplets range in size from roughly 0.5 micron to 500 micron in diameter, which corresponds to about 1 picoliter to 1 nanoliter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library may be critical to maintain the stability and integrity of the droplets and also may be essential for the subsequent use of the droplets within the library for the various biological and chemical assays described herein.

The invention provides a droplet library comprising a plurality of aqueous droplets within an immiscible fluid, wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid.

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are immune cells of a blood sample, and each immune cell is encapsulated to amplify and barcode the antibody sequences of the nucleotides in the immune cells.

For example, in one type of emulsion library, there are library elements that have different particles, i.e., cells or barcoded polynucleotides in a different medium and are encapsulated prior to pooling. In one example, a specified number of library elements, i.e., n number of different cells or barcoded polynucleotides, is contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

Reverse Transcription

In some cases, the target polynucleotides are prepared from an RNA by reverse transcription. In some cases, the target polynucleotides are prepared from a DNA by primer extension, such as using a polymerase.

The methods described herein can be used in coupled reverse transcription-PCR (reverse transcription-PCR). For example, reverse transcription and PCR can be carried out in two distinct steps. First a cDNA copy of the sample mRNA can be synthesized using either a polynucleotide dT primer, a sequence specific primer, a universal primer, or any primer described herein.

Reverse transcription and PCR can be carried out in a single closed vessel reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some cases, a thermostable reverse transcriptase is used and the reverse transcription reaction is carried out at about 37° C. to about 75° C., at about 37° C. to about 50° C., at about 37° C. to about 55° C., at about 37° C. to about 60° C., at about 55° C. to about 75° C., at about 55° C. to about 60° C., at about 37° C., or at about 60° C. In some cases, a reverse transcriptase that transfers 3 or more non-template terminal nucleotides to an end of the transcribed product is used.

A reverse transcription reaction and the PCR reaction described herein can be carried out in various formats known in the art, such as in tubes, microtiter plates, microfluidic devices, or, preferably, droplets.

A reverse transcription reaction can be carried out in volumes ranging from 5 μL to 100 or in 10 μL to 20 μL reaction volumes. In droplets, reaction volumes can range from 1 pL to 100 nL, or 10 pL to 1 nL. In some cases, the reverse transcription reaction is carried out in a droplet having a volume that is about or less than 1 nL. In some cases, a PCR reaction is in a droplet having a reaction volume ranges from 1 pL to 100 nL preferably 10 pL to 1 nL.

In some cases, the PCR reaction is carried out in a droplet having a volume that is about or less than 1 nL. In some cases, a reverse transcription reaction and a PCR reaction are carried out in the same droplet having a reaction volume ranges from 1 pL to 100 nL or 10 pL to 1 nL. In some cases, the reverse transcription reaction and the PCR reaction are carried out in a droplet having a volume that is about or less than 1 nL or a volume that is about or less than 1 pL. In some cases, a reverse transcription reaction and a PCR reaction are carried out in a different droplet. In some cases, a reverse transcription reaction and a PCR reaction are carried out in a plurality of droplets each having a reaction volume ranges from 1 pL to 100 nL or 10 pL to 1 nL. In some cases, the reverse transcription reaction and the PCR reaction are carried out in a plurality of droplets each having a volume that is about or less than 1 nL.

In some cases, a first PCR reaction is in a first droplet having a reaction volume ranges from 1 pL to 100 nL preferably 10 pL to 1 nL and a second PCR reaction is in a second droplet having a reaction volume ranges from 1 pL to 100 nL preferably 10 pL to 1 nL. In some cases, a first PCR reaction is in a first droplet having a volume that is about or less than 1 nL, and a second PCR reaction is in a second droplet having a volume that is about or less than 1 nL.

In some cases, a first PCR reaction and a second PCR reaction are carried out in a plurality of droplets each having a reaction volume ranges from 1 pL to 100 nL or 10 pL to 1 nL. In some cases, a first PCR reaction and a second PCR reaction are carried out in a plurality of droplets each having a volume that is about or less than 1 nL.

Target polynucleotides, such as RNA, can be reverse transcribed into cDNA using one or more reverse transcription primers. The one or more reverse transcription primers can comprise a region complementary to a region of the RNA, such as a constant region (e.g., a heavy or light chain constant region or a poly-A tail of mRNA). In some embodiments, the reverse transcription primers can comprise a first reverse transcription primer with a region complementary to a constant region of a first RNA, and a second reverse transcription primer with a region complementary to a constant region of a second RNA. In some embodiments, the reverse transcription primers can comprise a first reverse transcription primer with a region complementary to a constant region of a first RNA, and one or more reverse transcription primers with a region complementary to a constant region of one or more RNAs, respectively.

In some embodiments, reverse transcription primers do not comprise a barcode.

Reverse transcription primers can further comprise a region that is not complementary to a region of the RNA. In some embodiments, the region that is not complementary to a region of the RNA is 5' to a region of the primers that is complementary to the RNA. In some embodiments, the region that is not complementary to a region of the RNA is 3' to a region of the primers that is complementary to the RNA. In some embodiments, the region that is not complementary to a region of the RNA is a 5' overhang region. In some embodiments, the region that is not complementary to a region of the RNA comprises a priming site for amplification and/or a sequencing reaction. Using the one or more primers described herein, the RNA molecules are reverse transcribed using suitable reagents known in the art.

After performing the reverse transcription reactions of the RNA molecules, the resulting cDNA molecules can be barcoded with a molecular barcode and a vessel barcode and amplified by one or more PCR reactions, such as a first and/or a second PCR reaction. The first and/or second PCR reaction can utilize a pair of primers or a plurality of primer pairs. The first and/or second PCR reaction can utilize a plurality of forward/reverse primers and a reverse primer. The first and/or second PCR reaction can utilize a plurality of forward/reverse primers and a forward primer. A first and/or second primer of a plurality of forward/reverse primers can be a forward/reverse primer containing a region complementary to the cDNA molecules or barcoded cDNA molecules. A first and/or second primer of a plurality of forward/reverse primers can be a forward/reverse primer containing a region complementary to the barcoded cDNA molecules.

In some embodiments, a plurality of forward/reverse primers comprises one or more forward/reverse primers wherein each of the forward/reverse primers in the plurality of forward/reverse primers comprises a region complementary to one or more upstream or downstream regions to a V segment of the cDNAs or barcoded cDNAs. For example, a plurality of forward/reverse primers comprises a forward/reverse primer comprising a region complementary to a upstream or downstream region to a V segment of the cDNAs or barcoded cDNAs and one or more other forward/reverse primers comprising a region complementary to one or more other upstream or downstream regions to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs and a second forward/reverse primer comprising a region complementary to a second upstream or downstream region to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs, a second forward/reverse primer comprising a region complementary to a second upstream or downstream region to a V segment of the cDNAs or barcoded cDNAs, and a third forward/reverse primer comprising a region complementary to a third upstream or downstream region to a V segment of the cDNAs or barcoded cDNAs, etc. The primers in the plurality of forward/reverse primers can be used to anneal to all possible upstream or downstream regions of all V segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a C segment of the cDNAs or barcoded cDNAs. For example, a plurality of forward/reverse primers comprises a forward/reverse primer comprising a region complementary to a upstream or downstream region to a C segment of the cDNAs or barcoded cDNAs and one or more other forward/reverse primers comprising a region complementary to one or more other upstream or downstream regions to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs and a second forward/reverse primer comprising a region complementary to a second upstream or downstream region to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs, a second forward/reverse primer comprising a region complementary to a second upstream or downstream region to a C segment of the cDNAs or barcoded cDNAs, and a third forward/reverse primer comprising a region complementary to a third upstream or downstream region to a C segment of the cDNAs or barcoded cDNAs, etc. The primers in the plurality of forward/reverse primers can be used to anneal to all possible upstream or downstream regions of all C segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a molecular barcode of the barcoded cDNAs. For example, a plurality of forward/reverse primers comprises a forward/reverse primer comprising a region complementary to a upstream or downstream region to a molecular barcode of the barcoded cDNAs and one or more other forward/reverse primers comprising a region complementary to one or more other upstream or downstream regions to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs and a second forward/reverse primer comprising a region complementary to a second upstream or downstream region to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs, a second forward/reverse primer comprising a region complementary to a second upstream or downstream region to a molecular barcode of the barcoded cDNAs, and a third forward/reverse primer comprising a region complementary to a third upstream or downstream region to a molecular barcode of the barcoded cDNAs, etc. The plurality of forward/reverse primers can be used to anneal to all possible upstream or downstream regions of all molecular barcodes expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a vessel barcode of the barcoded cDNAs. For example, a plurality of forward/reverse primers comprises a forward/reverse primer comprising a region complementary to a upstream or downstream region to a vessel barcode of the barcoded cDNAs and one or more other forward/reverse primers comprising a region complementary to one or more other upstream or downstream regions to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs and a second forward/reverse primer comprising a region complementary to a second upstream or downstream region to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs, a second forward/reverse primer comprising a region complementary to a second upstream or downstream region to a vessel barcode of the barcoded cDNAs, and a third forward/reverse primer comprising a region complementary to a third upstream or downstream region to a vessel barcode of the barcoded cDNAs, etc. The primers in the plurality of forward/reverse primers can be used to anneal to all possible upstream or downstream regions of all vessel barcodes expressed by the cells, such as immune B-cells or T-cells, in the sample.

The forward/reverse primers in the plurality of forward/reverse primers further comprise a region that is not complementary to a region of the RNA. In some embodiments, the region that is not complementary to a region of the RNA is 5' to a region of the forward/reverse primers that is complementary to the RNA (i.e. upstream or downstream regions of a V segment). In some embodiments, the region that is not complementary to a region of the RNA is 3' to a region of the forward/reverse primers that is complementary to the RNA. In some embodiments, the region that is not complementary to a region of the RNA is a 5' overhang region. In some embodiments, the region that is not complementary to a region of the RNA comprises a priming site for amplification and/or a second sequencing reaction. In some embodiments, the region that is not complementary to a region of the RNA comprises a priming site for amplification and/or a third sequencing reaction. In some embodiments, the region that is not complementary to a region of the RNA comprises a priming site for a second and a third sequencing reaction. In some embodiments, the sequence of the priming site for the second and the third sequencing reaction are the same. Using the one or more forward/reverse primers and a reverse primer as described herein, the cDNA molecules are amplified using suitable reagents known in the art. In some embodiments, a region is complementary to a region of the RNA, such as the constant region or a poly-A tail of mRNA.

Amplification

The sample containing the target polynucleotide can comprise mRNA, or fragments thereof, which can be amplified. In some cases, the average length of the mRNA, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some cases, a target sequence from a relative short template, such as a sample containing a template that is about 40, 45, 50, 55, 60, 65, 70, 75, 80, 85, 90, 95, or 100 bases, is amplified.

An amplification reaction can comprise one or more additives. In some cases, the one or more additives are dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, an amplification reaction comprises 0, 1, 2, 3, 4, 5, 6, 7, 8, 9, or 10 different additives. In other cases, an amplification reaction comprises at least 0, 1, 2, 3, 4, 5, 6, 7, 8, 9, or 10 different additives.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/40 ul (1 nL droplets), 200,000 droplets/40 ul (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets do not coalesce during thermocycling. In other cases, greater than 100 or greater than 1,000 droplets do not coalesce during thermocycling.

Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (reverse transcription-PCR), single cell PCR, restriction fragment length polymorphism PCR (PCR-RFLP), PCR-RFLP/reverse transcription-PCR-RFLP, hot start PCR, nested PCR, in situ polony PCR, in situ rolling circle amplification (RCA), digital PCR (dPCR), droplet digital PCR (ddPCR), bridge PCR, picoliter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

In some embodiments, amplification does not occur on a solid support. In some embodiments, amplification does not occur on a solid support in a droplet. In some embodiments, amplification does occur on a solid support when the amplification is not in a droplet.

An amplification reaction can comprise one or more additives. In some embodiments, the one or more additives are dimethyl sulfoxide (DMSO), glycerol, betaine (mono) hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some embodiments, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives.

Primers

Generally, one or more pairs of primers can be used in a amplification reaction; one primer of a primer pair can be a forward primer and one primer of a primer pair can be a reverse primer.

In some cases, a first pair of primers can be used in the amplification reaction; one primer of the first pair can be a forward primer complementary to a sequence of a first target polynucleotide molecule and one primer of the first pair can be reverse primer can be complementary to a second sequence of the first target polynucleotide molecule, and a first target locus can reside between the first sequence and the second sequence. In some embodiments, the first target locus comprises a $V_H$ or $V\alpha$ or $V\gamma$ sequence.

In some cases, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a $V_L$ or $V\beta$ or $V\delta$ sequence.

In some cases, a third pair of primers can be used in the amplification reaction; one primer of the third pair can be a forward primer complementary to a first sequence of a third target polynucleotide molecule and one primer of the third pair can be a reverse primer complementary to a second sequence of the third target polynucleotide molecule, and a third target locus can reside between the first sequence and the second sequence. In some embodiments, the third target locus comprises a barcode, such as a molecular barcode or vessel barcode.

The length of the forward primer and the reverse primer can depend on the sequence of the target polynucleotide and the target locus. For example, the length and/or $T_M$ of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. In some embodiments, a primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or further amplification, or sequencing of an amplified product. For example, the additional sequence can comprise a primer binding site, such as a universal primer binding site. A region of the primer which is sufficiently complementary to a template to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization. Different primer pairs can anneal and melt at about the same temperatures, for example, within 1° C., 2° C., 3° C., 4° C., 5° C., 6° C., 7° C., 8° C., 9° C. or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to target polynucleotides described herein.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule ($T_M=2(A+T)+4(G+C)$). Computer programs can also be used to design primers. The $T_M$ (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the $T_M$ can be recalculated based on both the sequences of the 5' half and the 3' half of each primer.

Conducting the one or more reactions of the methods disclosed herein can comprise the use of one or more primers. As used herein, a primer comprises a double-stranded, single-stranded, or partially single-stranded polynucleotide that is sufficiently complementary to hybridize to a template polynucleotide. A primer can be a single-stranded DNA prior to binding a template polynucleotide. In some embodiments, the primer initially comprises double-stranded sequence. A primer site includes the area of the template to which a primer hybridizes. In some embodiments, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase. A primer pair includes 2 primers: a first primer with a 5' upstream region that hybridizes with a 5' end of a template sequence, and a second primer with a 3' downstream region that hybridizes with the complement of the 3' end of the template sequence. A primer set includes two or more primers: a first primer or first plurality of primers with a 5' upstream region that hybridizes with a 5' end of a template sequence or plurality of template sequences, and a second primer or second plurality of primers with a 3' downstream region that hybridizes with the complement of the 3' end of the template sequence or plurality of template sequences. In some embodiments, a primer comprises a target specific sequence. In some embodiments, a primer comprises a sample barcode sequence. In some embodiments, a primer comprises a universal priming sequence. In some embodiments, a primer comprises a PCR priming sequence. In some embodiments, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, −47F (M13F), alfaMF, AOX3', AOX5', BGHr, CMV-30, CMV-50, CVMf, LACrmt, lamgda gt10F, lambda gt 10R, lambda gt11F, lambda gt11R, M13 rev, M13Forward(−20), M13Reverse, male, p10SEQPpQE, pA-120, pet4, pGAP Forward, pGL-RVpr3, pGLpr2R, pKLAC14, pQEFS, pQERS, pucU1, pucU2, reversA, seqIREStam, seqIRESzpet, seqori, seqPCR, seqpIRES−, seqpIRES+, seqpSecTag, seqpSec-Tag+, seqretro+PSI, SP6, T3-prom, T7-prom, and T7-termInv. As used herein, attach can refer to both or either covalent interactions and noncovalent interactions. Attachment of the universal primer to the universal primer binding site may be used for amplification, detection, and/or sequencing of the polynucleotide and/or amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some embodiments, the universal primer binding site comprises 1-10, 10-20, 10-30 or 10-100 nucleotides or base pairs. In some embodiments, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can have a length compatible with its use in synthesis of primer extension products. A primer can be a polynucleotide that is 8 to 200 nucleotides in length. The length of a primer can depend on the sequence of the template polynucleotide and the template locus. For example, the length and/or melting temperature ($T_M$) of a primer or primer set can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, primers are about 8-100 nucleotides in length, for example, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, or 20-60 nucleotides in length and any length there between. In some embodiments, primers are at most about 10, 12, 15, 20, 21, 22, 23, 24, 25, 26, 27, 28, 29, 30, 35, 40, 45, 50, 55, 60, 65, 70, 75, 80, 85, 90, 95 or 100 nucleotides in length.

Generally, one or more pairs of primers can be used in an exponential amplification reaction; one primer of a primer pair can be a forward primer and one primer of a primer pair can be a reverse primer. In some embodiments, a first pair of primers can be used in the exponential amplification reaction; one primer of the first pair can be a forward primer complementary to a sequence of a first template polynucleotide molecule and one primer of the first pair can be a reverse primer complementary to a second sequence of the first template polynucleotide molecule, and a first template locus can reside between the first sequence and the second sequence. In some embodiments, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence. In some embodiments, a third pair of primers can be used in the amplification reaction; one primer of the third pair can be a forward primer complementary to a first sequence of a third template polynucleotide molecule and one primer of the third pair can be a reverse primer complementary to a second sequence of the third template polynucleotide molecule, and a third template locus can reside between the first sequence and the second sequence.

The one or more primers can anneal to at least a portion of a plurality of template polynucleotides. The one or more primers can anneal to the 3' end and/or 5' end of the plurality of template polynucleotides. The one or more primers can anneal to an internal region of the plurality of template polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends the plurality of template polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some embodiments, the one or more custom primers anneal to an SBC, a target specific region, complements thereof, or any combination thereof. The one or more primers can comprise a universal primer. The one or more primers primer can be designed to amplify or perform primer extension, reverse transcription, linear extension, non-exponential amplification, exponential amplification, PCR, or any other amplification method of one or more target or template polynucleotides The target specific region can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. in some embodiments, the target specific region comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some embodiments, different primer pairs can anneal and melt at about the same temperatures, for example, within 1° C., 2° C., 3° C., 4° C., 5° C., 6° C., 7° C., 8° C., 9° C. or 10° C. of another primer pair. In some embodiments, one or more primers in a plurality of primers can anneal and melt at about the same temperatures, for example, within 1, 2, 3, 4, 5, 6, 7, 8, 9 or 10° C. of another primer in the plurality of primers. In some embodiments, one or more primers in a plurality can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 different primers. For example, each primer in a plurality of primers can comprise a different target or template specific region or sequence.

Sequencing

After performing one or more of the methods or method steps described herein, a library of polynucleotides generated can be sequenced.

Sequencing can be performed by any sequencing method known in the art. In some embodiments, sequencing can be performed in high throughput. Suitable next generation sequencing technologies include the 454 Life Sciences platform (Roche, Branford, Conn.) (Margulies et al., Nature, 437, 376-380 (2005)); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., Genome Res. 16, 383-393 (2006); and U.S. Pat. Nos. 6,306,597, 7,598,035, 7,232,656), or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453); or the Helicos True Single Molecule DNA sequencing technology (Harris et al., Science, 320, 106-109 (2008); and U.S. Pat. Nos. 7,037,687, 7,645,596, 7,169,560, and 7,769,400), the single molecule, real-time (SMRTTm) technology of Pacific Biosciences, and sequencing (Soni et al., Clin. Chem. 53, 1996-2001 (2007)). These systems allow multiplexed parallel sequencing of many polynucleotides isolated from a sample (Dear, Brief Funct. Genomic Proteomic, 1(4), 397-416 (2003) and McCaughan et al., J. Pathol., 220, 297-306 (2010)). In some embodiments, polynucleotides are sequenced by sequencing by ligation of dye-modified probes, pyrosequencing, or single-molecule sequencing. Determining the sequence of a polynucleotide may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT(™) sequencing, Polony sequencing, DNA nanoball sequencing, and VisiGen Biotechnologies approach. Alternatively, determining the sequence of polynucleotides may use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing can comprise MiSeq sequencing. Sequencing can comprise HiSeq sequencing. In some embodiments, determining the sequence of a polynucleotide comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of a polynucleotide can be determined by electron microscopy or a chemical-sensitive field effect transistor (chemFET) array.

A method can further comprise sequencing one or more polynucleotides in the library. A method can further comprise aligning one or more polynucleotide sequences, sequence reads, amplicon sequences, or amplicon set sequences in the library to each other.

As used herein, aligning comprises comparing a test sequence, such as a sequence read, to one or more other test sequences, reference sequences, or a combination thereof. In some embodiments, aligning can be used to determine a consensus sequence from a plurality of sequences or aligned sequences. In some embodiments, aligning comprises determining a consensus sequence from a plurality of sequences that each has an identical molecular barcode or vessel barcode. In some embodiments, the length of a sequence aligned for comparison purposes is at least 30%, at least 40%, at least 50%, at least 60%, at least 70%, at least 80%, at least 90%, or at least 95%, of the length of a reference sequence. The actual comparison of the two or more sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

Sequencing can comprise sequencing at least about 10, 20, 30, 40, 50, 60, 70, 80, 90, 100 or more nucleotides or base pairs of the polynucleotides. In some embodiments, sequencing comprises sequencing at least about 200, 300, 400, 500, 600, 700, 800, 900, 1000, or more nucleotides or base pairs of the polynucleotides. In other instances, sequencing comprises sequencing at least about 1500, 2000, 3000, 4000, 5000, 6000, 7000, 8000, 9000, 10,000, or more nucleotides or base pairs of the polynucleotides.

Sequencing can comprise at least about 200, 300, 400, 500, 600, 700, 800, 900, 1000 or more sequencing reads per run. As used herein, a sequence read comprises a sequence of nucleotides determined from a sequence or stream of data generated by a sequencing technique. In some embodiments, sequencing comprises sequencing at least about 1500, 2000, 3000, 4000, 5000, 6000, 7000, 8000, 9000, 10,000, or more sequencing reads per run. Sequencing can comprise more than, less than, or equal to about 1,000,000,000 sequencing reads per run. Sequencing can comprise more than, less than, or equal to about 200,000,000 reads per run.

In some embodiments, the number of sequence reads used to determine a consensus sequence is from about 2-1000 sequence reads. For example, the number of sequence reads used to determine a consensus sequence can be from about 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 sequence reads. In some embodiments, the number of sequence reads used to determine a consensus sequence is at least about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads. In some embodiments, the number of sequence reads used to determine a consensus sequence is at most about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads.

A method can comprise sequencing mis-reads. A method can comprise determining the number of mis-reads, such as for determining a reaction condition or designing primer sequences. Comparing the number of mis-reads generated under one or more first conditions or sets of conditions can be used to determine a preferred condition or condition set. For example, a first method can be carried out at a high salt concentration during a PCR reaction, and a second method can be carried out at a low salt concentration during a PCR reaction, wherein the first and second method are carried out substantially the same aside from the salt concentration difference. If the first method results in a higher number of mis-reads, such as a higher number of mis-reads for a particular target polynucleotide sequence or primer, a lower salt reaction condition can be determined to be preferred for that particular target polynucleotide sequence or primer.

Diagnostics

In some embodiments, a method can further comprise diagnosing, prognosing, monitoring, treating, ameliorating and/or preventing in a subject a disease, disorder, symptom and/or condition. In some embodiments, a method can further comprise diagnosing, prognosing, monitoring, treating, ameliorating and/or preventing in a subject a disease, disorder, symptom and/or condition, based on a presence, absence, or level of a target polynucleotide. In some embodiments, a method can further comprise diagnosing, prognosing, monitoring, treating, ameliorating and/or preventing in a subject a disease, disorder, symptom and/or condition, based on a presence, absence, or level of one or more target polynucleotides.

In some embodiments, a method can further comprise diagnosing, prognosing, monitoring, treating, ameliorating and/or preventing in a subject a disease, disorder, symptom and/or condition based on a presence, absence, level, or sequence of one or more of the sequences obtained using the methods described herein. For example, a diagnosis of a disease can be made based on a presence, absence, level, or sequence of a variant sequence obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence, one or more of the sequence reads obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence of one or more of the consensus sequences obtained using the methods described herein. In some embodiments, a method can further comprise diagnosing, prognosing, monitoring, treating, ameliorating and/or preventing in a subject a disease, disorder, symptom and/or condition based on a determination of a level (e.g., an amount or concentration) of a target polynucleotide in a sample. A level of a target polynucleotide in a sample can be determined based on one or more sequence reads, sequences, consensus sequences, or any combination thereof. A level of each of a plurality of target polynucleotides in a sample can be determined using the methods described herein. A level of each of a plurality of target polynucleotide in a sample can be determined based on a number of sequence reads, sequences, consensus sequences, or any combination thereof of each target polynucleotide in the plurality. For example, a level of a first target polynucleotide and a level of a second target polynucleotide can be determined using the methods described herein.

In some embodiments, first and second target polynucleotides of a plurality of target polynucleotides are the same. For example, a first target polynucleotide can comprise a first copy of an mRNA molecule and a second target polynucleotide can comprise a second copy of an mRNA molecule. In some embodiments, the first and second target polynucleotides are different. For example, a first target polynucleotide can comprise a first mRNA molecule and a second target polynucleotide can comprise a second mRNA molecule transcribed from a different gene than the first mRNA molecule. For example, a first target polynucleotide can comprise a first allele and a second target polynucleotide can comprise a second allele. For example, a first target polynucleotide can comprise a wild-type sequence and a second target polynucleotide can comprise a variant sequence.

In some embodiments, a method can further comprise diagnosing or prognosing a subject with a disease, disorder, symptom and/or condition with at least 50% confidence. For example, a diagnosis or prognosis of a subject with a disease, disorder, symptom and/or condition can be determined with at least 50%, 55%, 60%, 65%, 70%, 75%, 80%, 85%, 90%, 95%, 98%, 99%, or 100% confidence. In some embodiments, a diagnosis or prognosis of a subject with a disease, disorder, symptom and/or condition can be determined with a 50%-100% confidence. For example, a diagnosis or prognosis of a subject with a disease, disorder, symptom and/or condition can be determined with a 60%-100%, 70%-100%, 80%-100%, 90%-100%, 50%-90%, 50%-80%, 50%-70%, 50%-60%, 60%-90%, 60%-80%, 60%-70%, 70%-90%, 70%-80%, or 80%-90% confidence.

In some embodiments, the presence, absence, level, sequence, or any combination thereof, of a target polynucleotide in the subject, such as a biomarker, can be determined with at least 50% confidence. For example, the presence, absence, level, sequence, or any combination thereof, of a target polynucleotide in the subject can be determined with at least 50%, 55%, 60%, 65%, 70%, 75%, 80%, 85%, 90%, 95%, 98%, 99%, or 100% confidence. In some embodiments, the presence, absence, level, sequence, or any combination thereof, of a target polynucleotide in the subject can be determined with a 50%-100% confidence. For example, the presence, absence, level, sequence, or any combination thereof, of a target polynucleotide in the subject can be determined with a 60%-100%, 70%400%, 80%-100%, 90%-100%, 50%-90%, 50%-80%, 50%-70%, 50%-60%, 60%-90%, 60%-80%, 60%-70%, 70%-90%, 70%-80%, or 80%-90% confidence.

Enzymes

The methods and kits disclosed herein may comprise one or more enzymes. Examples of enzymes include, but are not limited to ligases, reverse transcriptases, polymerases, and restriction nucleases.

In some embodiments, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some embodiments, the reverse transcriptase is a HIV-1 reverse transcriptase, M-MLV reverse transcriptase, AMV reverse transcriptase, and telomerase reverse transcriptase. In some embodiments, the reverse transcriptase is M-MLV reverse transcriptase.

In some embodiments, the methods and kits disclosed herein comprise the use of one or more proteases In some embodiments, the methods and kits disclosed herein comprise the use of one or more polymerases. Examples of polymerases include, but are not limited to, DNA polymerases and RNA polymerases. In some embodiments, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9° N™ m DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some embodiments, the polymerase is an RNA polymerases such as RNA polymerase I, RNA polymerase II, RNA polymerase III, *E. coli* Poly(A) polymerase, phi6 RNA polymerase (RdRP), Poly(U) polymerase, SP6 RNA polymerase, and T7 RNA polymerase.

Additional Reagents

The methods and kits disclosed herein may comprise the use of one or more reagents.

Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidene difluoride (PVDF)) and the like. Examples of beads for use according to the embodiments can include an affinity moiety that allows the bead to interact with a nucleic acid molecule. A solid phase (e.g. a bead) can comprise a member of a binding pair (e.g. avidin, streptavidin or derivative thereof). For instance, the bead may be a streptavidin-coated bead and a nucleic acid molecule for immobilization on the bead can include a biotin moiety. In some cases, each polynucleotide molecule can include two affinity moieties, such as biotin, to further stabilize the polynucleotide. Beads can include additional features for use in immobilizing nucleic acids or that can be used in a downstream screening or selection processes. For example, the bead may include a binding moiety, a fluorescent label or a fluorescent quencher. In some cases, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide-dT conjugated beads, silica beads, silica-like beads, anti-biotin microbead, anti-fluoro chrome microbead, and BcMag™ Carboxy-Terminated Magnetic Beads. Beads or particles may be swellable (e.g., polymeric beads such as Wang resin) or non-swellable (e.g., CPG). In some embodiments a solid phase is substantially hydrophilic. In some embodiments a solid phase (e.g. a bead) is substantially hydrophobic. In some embodiments a solid phase comprises a member of a binding pair (e.g. avidin, streptavidin or derivative thereof) and is substantially hydrophobic or substantially hydrophilic. In some embodiments, a solid phase comprises a member of a binding pair (e.g. avidin, streptavidin or derivative thereof) and has a binding capacity greater than about 1350 picomoles of free capture agent (e.g. free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 picomoles of free capture agent per mg solid support. Other examples of beads that are suitable for the invention are gold colloids or beads such as polystyrene beads or silica beads. Substantially any bead radii may be used. Examples of beads may include beads having a radius ranging from 150 nanometers to 10 microns. Other sizes may also be used.

The methods and kits disclosed herein may comprise the use of one or more buffers. Examples of buffers include, but are not limited to, wash buffers, ligation buffers, hybridization buffers, amplification buffers, and reverse transcription buffers. In some embodiments, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., a polynucleotide and/or amplicon). For example, the carrier may decrease non-specific loss of a polynucleotide through absorption to surfaces. The carrier may decrease the affinity of a polynucleotide to a surface or substrate (e.g., container, Eppendorf tube, pipet tip). Alternatively, the carrier may increase the affinity of a polynucleotide to a surface or substrate (e.g., bead, array, glass, slide, chip). Carriers may protect the polynucleotide from degradation. For example, carriers may protect an RNA molecule from ribonucleases. Alternatively, carriers may protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA polynucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA polynucleotides. The RNA carrier may be a polyadenylated RNA. Alternatively, the RNA carrier may be a non-polyadenylated RNA. In some embodiments, the carrier is from a bacteria, yeast, or virus. For example, the carrier may be a polynucleotide or a polypeptide derived from a bacteria, yeast or virus. For example, the carrier is a protein from *Bacillus subtilis*. In another example, the carrier is a polynucleotide from *Escherichia coli*. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control polynucleotides, inactive enzymes, non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some embodiments, the spike-in template is added to an amplification reaction after cycle number 2, 3, 4, 5, 6, 7, 8, 9, 10, 11, 12, 13, 14, 15, 20, 25, 30, 35, 40, 45, or 50. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-9119102); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

EXAMPLES

Example 1a

Protocol for Preparing Cells for Performing Emulsion-Based, Massively High Throughput Single-Cell Polynucleotide Sequencing Cell populations of interest were obtained. These included total PBMCs, sorted cells, antibody-enriched B or T cells, or other cell types. The cells had an intact plasma membrane so that they did not leak excessive amounts of mRNA into the surrounding media. The cells did not need to be viable.

The cells were washed by centrifugation (200 g for 10 min for T-cells or B-cells) twice in Cell Buffer: 1× Dulbecco's Phosphate-Buffered Saline (PBS). The cells were then diluted in Cell Buffer to a cell concentration of $3.5 \times 10^6$/mL. The suspension was then pipetted through a 20 µm cell strainer.

Example 1b

Protocol for Preparing Solid Tissues for Performing Emulsion-Based, Massively High Throughput Single-Cell Polynucleotide Sequencing A solid tissue (e.g. tumor or non-tumor biopsy sample) was treated with various proteases including collagenase III (200 U/mL), DNase I (200 U/mL) and trypsin (5 mg/mL), and an NEDB (Invitrogen) to yield a mixture of individual cells and aggregates containing more than one cell. Briefly, tumors removed from mice were added to cold culture media and surrounding mouse breast tissue and fat were removed. The tumors were minced into 2-4 mm fragments, which were then incubated with the appropriate dissociation solutions or enzymes for 30 min at 37° C. The tumor fragments were mixed up and down every 10 min using a 1,000 mL micropipette with a tip cut to a diameter adapted to tissue fragment size. After each incubation period, the fragments were filtered through a 40 mm nylon mesh cell strainer. The released cells were centrifuged at 1200 r.p.m. for 2 min and stored in cold medium with 30% FCS at 4° C. Fresh dissociation solution was added to the remaining tissue fragments for 30 min. Dissociation was stopped when no additional cells were released. The fragments were pushed through a sieve and all cells from all incubation periods were pooled and counted. Cell suspensions are then strained through a strainer (e.g. 10, 20, 30, 40 µm) to remove large aggregates. Cells were washed by centrifugation (200 g for 10 minutes for T-cells or B-cells) twice in Cell Buffer: 1x Dulbecco's Phosphate-Buffered Saline (PBS). The cell population was not stained, sorted, or otherwise separated before analysis by emulsion.

An alternative method for preparing the removed tumors was also performed. The removed tumors were placed in 1 mL dissociation buffer 1 (100 U/ml Collagenase type IV and 100 µg/mL DNase in RPMI+10% FBS) or dissociation buffer 2 (RPMI medium supplemented with 5% FBS, Collagenase type I (200 U/mL) and DNase I (100 µg/mL)) and incubated for 30 min at 37° C. If myeloid cells were to be subsequently isolated, 5% FBS and Collagenase type I was substituted in dissociation buffer 2 with 10% FBS and Collagenase type IV (200 U/ml), respectively. The tumor fragments were mixed up and down using a 1,000 mL micropipette. The suspension was then filtered through a 70 µm filter and washed 3× with MACs separation buffer supplemented with 10% FBS for myeloid cell isolation. For very large tumors (>300 mm$^2$), inflammatory cells can be pre-enriched using density gradient centrifugation (Percoll or Ficoll). The filtered cell suspension was then centrifuged at 400 g for 10 min. The pellet was rinsed with 10 mL MACs buffer and centrifuged again with the same settings.

Example 2

Protocol for Preparing the Emulsion Reaction Mixture for Performing Emulsion-Based, Massively High Throughput Single-Cell Polynucleotide Sequencing An emulsion reaction mixture containing the reagents and oligonucleotides in Table 1 below was mixed at room temperature in a PCR-clean hood.

TABLE 1

| Reagent | Stock conc. (mM) | Final conc. in droplet (mM) | Final conc. in rxn phase (mM) | µL per 200 µL |
|---|---|---|---|---|
| Tris-Cl, pH 8.0 | 500.00 | 50.00 | 100.00 | 40.00 |
| MgSO$_4$ | 100.00 | 3.00 | 6.00 | 12.00 |
| DTT | 1,000.00 | 10.00 | 20.00 | 4.00 |
| dNTPs each | 10.00 | 0.50 | 1.00 | 20.00 |
| 5'biotin oligo-dT | $1.40 \times 10^{-2}$ | $2.50 \times 10^{-4}$ | $5.00 \times 10^{-4}$ | 7.14 |
| Template switch oligo | 0.1 | $1.00 \times 10^{-3}$ | $2.00 \times 10^{-3}$ | 4.00 |
| DB template molecules/µL | $1.00 \times 10^6$ | $1.75 \times 10^4$ | $3.50 \times 10^4$ | 7.00 |
| DB primer fwd | 0.2 | $5.00 \times 10^{-4}$ | $1.00 \times 10^{-3}$ | 1.00 |
| DB primer rev | 0.2 | $7.50 \times 10^{-4}$ | $1.50 \times 10^{-3}$ | 1.50 |
| HALT Protease inhibitor (X) | 200 | 1.00 | 2.00 | 2.00 |
| Enzymatics RNase Inhibitor (U/µL) | 40 | 0.40 | 0.80 | 4.00 |
| MMLV RNaseH-reverse transcriptase | | | | 10.00 |
| Phusion HF DNA polymerase | | | | 10.00 |
| Triton X-100 (% v/v) | 2.5 | 0.25 | 0.50 | 40.00 |
| Water | | | | to 200 |

Oligonucleotide sequences:

| | |
|---|---|
| 5'biotin oligo-dT anchored reverse transcription primer | /5BiosG//iSp18/TTT TTT TTT TTT TTT TTT TTT TTT T V N (SEQ ID NO: 24) |

TABLE 1-continued

| | |
|---|---|
| Droplet barcode template: | ATCCATCCACGACTGACGGACGTATTAAA NNNNAGATCGGAAGAGCACACGTCTGAACTCCAGTCACC (SEQ ID NO: 25) |
| template switch oligo | AATACGTCCGTCAGTCGTGGATGNNTNNANNTrGrGG (SEQ ID NO: 26) |
| Vessel Barcode forward | CATCCACGACTGACGGACGTATT (SEQ ID NO: 27) |
| Vessel Barcode reverse | GTGACTGGAGTTCAGACGTGTGCT (SEQ ID NO: 28) |

/5Biosg/ = 5'biotin modification; /iSp18/ = 18-carbon spacer; V = A, C, or G; N = any base; rG = riboguanosine; W = A or T

Example 3

Protocol for Generating Emulsions for Performing Emulsion-Based, Massively High Throughput Single-Cell Polynucleotide Sequencing Once cells and reaction mixture are prepared, the emulsion was formed. A 100 µL Hamilton Microliter syringe was used to overload a 100 µL PEEK sample loop in two injections of ~100 µL each of the reaction mixture. A 100 µL Hamilton Gastight syringe was used to load ~110 µL of the cell suspension into a ~100 µL 0.2 mm internal diameter FEP tubing loop. The loop was attached to a mechanical rotator that was constantly inverting the cell loop approximately once every 1-2 seconds to prevent cell settling and bunching. The emulsion was formed by focused flow jetting through a Dolomite 2-reagent chip with internal fluorophilic coating. The outer oil channels contained 0.5-5.0% (w/v) polyethylene glycol-based surfactant in HFE7500 (Novec 7500) fluorocarbon oil. The emulsion jet was run at a constant flow rate (equal in cell phase and reaction phase channels). The emulsion chip output was collected through a 12 cm, 0.5 mm internal diameter PEEK tube, by dropping into polypropylene PCR tubes that are kept at approximately 0° C. in a chilled block. Four fractions were collected, each containing 50 µL of aqueous material in emulsion (5 minutes of run time per fraction). Most of the settled oil was removed from the bottom of each tube with a capillary micropipette. Each emulsion fraction was gently overlayed with 40 µL of Overlay Solution: 50 mM Na-EDTA, pH 8.0, 0.002% (w/v) cresol red. The emulsions were incubated in a thermal cycler with the following program (minutes: seconds):
1. 42.0° C. for 30:00 (reverse transcription)
2. 95.0° C. for 05:00 (denature reverse transcriptase and DNA templates)
3. 95.0° C. for 00:10
4. 65.0° C. for 00:30
5. 72.0° C. for 00:30
6. Go to 3, total 55 cycles (amplify Vessel Barcode and fuse to cDNA)
7. 4.0° C. no time limit The emulsion was held at 4.0° C. overnight.

Example 4

Protocol for Breaking Emulsions for Performing Emulsion-Based, Massively High Throughput Single-Cell Polynucleotide Sequencing Using a capillary micropipette tip, as much Overlay Solution was removed as possible without removing emulsion material. To each tube, 12.5 µL Qiagen Protease solution and 2.5 µL of 0.5 M Na-EDTA, pH 8.0 was added. The emulsion was broke by adding 40 µL of 1:1 FC-40:perfluorooctanol and gently inverting about 10 times.

The contents of tube were gently centrifuged and incubated in a thermal cycler with the following program (minutes: seconds):
1. 50° C. for 15:00 (protease digestion)
2. 70° C. for 10:00 (protease inactivation)
3. 95° C. for 03:00 (protease inactivation and DNA denaturation)
4. 4.0° C. no time limit The tube was centrifuged and the upper aqueous phase and interface was moved to a fresh microcentrifuge tube and centrifuged at 15,000 g for 1 minute. The upper aqueous phase was transferred to a new tube, without disturbing the interface

Example 5

Protocol for Cleaning Polynucleotides from Emulsions for Performing Emulsion-Based, Massively High Throughput Single-Cell Polynucleotide Sequencing 0.25V of NEB streptavidin beads were added in 2×BW (10 mM Tris-Cl, pH 8.0, 1 mM EDTA, 2 M NaCl, 0.2% Tween-20) and incubated at RT for 15 min. The beads were then washed with 1×BW, washed three times with 0.001% Tween-20, and eluted by adding 0.25V of 0.001% Tween-20 and heating to 95° C. for 3 min. 5 volumes of Qiagen Buffer PB was added and applied to a Zyppy silica column. The beads were then washed with 0.7 mL of Zyppy wash buffer and eluted in 180 µL of: 5 mM Tris-Cl, pH 8.8, 0.1 mM EDTA, 0.001% Tween-20

Example 6

Protocol for First PCR Reaction (PCR1) of Polynucleotides for Next Generation Sequencing for Performing Emulsion-Based, Massively High Throughput Single-Cell Polynucleotide Sequencing 163.2 µL of purified cDNA was used for the PCR1. An exemplary set up for the first PCR reaction is shown in Table 2 below.

TABLE 2

| PCR1 Library | | | | | |
|---|---|---|---|---|---|
| Reagent | Stock Conc. | Final Conc. | 20-µL rxn | 60 µL rxn | 240 µL rxn |
| Q5 buffer 5X | 5.00 mM | 1.00 µM | 4.00 µL | 12.00 µL | 48.00 µL |
| Each dNTPs | 10.00 mM | 0.20 µM | 0.40 µL | 1.20 µL | 4.80 µL |
| Q5 Hot Start | 125.00 mM | 1.00 µM | 0.16 µL | 0.48 µL | 1.92 µL |

TABLE 2-continued

| PCR1 Library | | | | | |
|---|---|---|---|---|---|
| 633 primer | 10 um | | 0.16 µL | 0.48 µL | 1.92 µL |
| [IgH/TCRα]-[IgL/TCRβ]-[C] primer mix | 10 um (each) | | 0.16 µL | 0.48 µL | 1.92 µL |
| cDNA | | | 13.60 µL | 40.80 µL | 163.20 µL |
| H2O | | | 1.52 µL | 4.56 µL | 18.24 µL |

| IgH/TCRα/TCRγ primer sequences of [IgH/TCRα/TCRγ]-[IgL/TCRβ/TCRδ]-[C] primer mix | |
|---|---|
| IgM | GGGTTGGGGCGGATGCAC (SEQ ID NO: 1) |
| IgD | CATCCGGAGCCTTGGTGG (SEQ ID NO: 2) |
| IgA | CCTTGGGGCTGGTCGGGG (SEQ ID NO: 3) |
| IgE | CGGATGGGCTCTGTGTGG (SEQ ID NO: 4) |
| IgG | CCGATGGGCCCTTGGTGG (SEQ ID NO: 5) |
| TCRα1 | GGATTTAGAGTCTCTCAGCTG (SEQ ID NO: 6) |
| TCRα2 | CACGGCAGGGTCAGGGTTC (SEQ ID NO: 29) |
| TCRγ | AAAATAGTGGGCTTGGGG (SEQ ID NO: 30) |

| IgL/TCRβ/TCRδ primer sequences of [IgH/TCRα/TCRγ]-[IgL/TCRβ/TCRδ]-[C] primer mix | |
|---|---|
| IgKJ1 | TTTGATCTCCACCTTGGTCCCTCCGC (SEQ ID NO: 9) |
| IgKJ2 | TTTGATCTCCAGCTTGGTCCCTGG (SEQ ID NO: 10) |
| IgKJ3 | TTTGATATCCACTTTGGTCCCAGGGC (SEQ ID NO: 11) |
| IgKJ4 | TTTGATTTCCACCTTGGTCCCTTGGC (SEQ ID NO: 12) |
| IgKJ5 | TTTAATCTCCAGTCGTGTCCCTTGGC (SEQ ID NO: 13) |
| IgLJ1 | GAGGACGGTCACCTTGGTGCCA (SEQ ID NO: 14) |
| IgLJ2 | TAGGACGGTCAGCTTGGTCCCTCC (SEQ ID NO: 15) |
| IgLJ3 | GAGGACGGTCAGCTGGGTGCC (SEQ ID NO: 16) |
| IgLJ4 | TAAAATGATCAGCTGGGTTCCTCCAC (SEQ ID NO: 17) |
| IgLJ5 | TAGGACGGTGACCTTGGTCCCAGT (SEQ ID NO: 31) |
| TCRβ1 | GGGAGATCTCTGCTTCTGATG (SEQ ID NO: 19) |
| TCRβ2 | CGACCTCGGGTGGGAACAC (SEQ ID NO: 32) |
| TCRδ | AGACAAGCGACATTTGTTCCA (SEQ ID NO: 33) |

| C-primer sequence of [IgH/TCRα/TCRγ]-[IgL/TCRβ/TCRδ]-[C] primer mix | |
|---|---|
| 633 | GTGACTGGAGTTCAGACGTGTGCTCTTCCGATCT (SEQ ID NO: 34) |

Four 60 µL reactions were aliquoted in PCR tubes and the following program was run in a thermocycler:
1. 98° C. for 01:00
2. 98° C. for 00:10
3. 64° C. for 00:20
4. 72° C. for 00:20
5. Go to 2 for a total of 6 cycles
6. 4° C. no time limit The PCR product was purified with 1.2 volumes of AMPure XP, washed with 80% ethanol and eluted in 60 µL Dilution Buffer (10 mM Tris-Cl, pH 8.0, 0.1 mM EDTA).

Example 7

Protocol for Second PCR Reaction (PCR2) of Polynucleotides for Next Generation Sequencing for Performing Emulsion-Based, Massively High Throughput Single-Cell Polynucleotide Sequencing 20 µL of purified PCR1 product was used for each sub-library (e.g., IgL or IgH chain or TCRα or TCRβ chain, or TCRγ or TCRδ chain). An exemplary set up for the second PCR reaction is shown in Table 3 below.

TABLE 3

| PCR2 Library | | | | |
|---|---|---|---|---|
| Reagent | Stock Conc. | Final Conc. | 20 µL rxn | 50 µL rxn |
| Q5 buffer 5X | 5.00 mM | 1.00 µM | 4.00 µL | 10.00 µL |
| Each dNTPs | 10.00 mM | 0.20 µM | 0.40 µL | 1.00 µL |
| Q5 Hot Start | 125.00 mM | 1.00 µM | 0.16 µL | 0.40 µL |
| C7-index-P7 primer | 2 µM | | 1.60 µL | 4.00 µL |
| [P5-IgH/TCRα/TCRγ]-[P5-IgL/TCRβ/TCRδ] primer mix | 1 µM (each) | | 1.60 µL | 4.00 µL |
| cDNA | | | 8.00 µL | 20.00 µL |
| H₂0 | | | 4.24 µL | 10.60 µL |

| Primer sequences of P5-IgH/TCRα/TCRγ heavy mix | |
|---|---|
| IgM | ACACTCTTTCCCTACACGACGCTCTTCCGATCTGGGTTGGGGCGGATGCAC (SEQ ID NO: 35) |
| IgD | ACACTCTTTCCCTACACGACGCTCTTCCGATCTCATCCGGAGCCTTGGTGG (SEQ ID NO: 36) |
| IgA | ACACTCTTTCCCTACACGACGCTCTTCCGATCTCCTTGGGGCTGGTCGGGG (SEQ ID NO: 37) |

TABLE 3-continued

| | PCR2 Library |
|---|---|
| IgE | ACACTCTTTCCCTACACGACGCTCTTCCGATCTCGGATGGGCTCTGTGTGG (SEQ ID NO: 38) |
| IgG | ACACTCTTTCCCTACACGACGCTCTTCCGATCTCCGATGGGCCCTTGGTGG (SEQ ID NO: 39) |
| TCRα1 | ACACTCTTTCCCTACACGACGCTCTTCCGATCTGGATTTAGAGTCTCTCAGCTG (SEQ ID NO: 40) |
| TCRα2 | ACACTCTTTCCCTACACGACGCTCTTCCGATCTCACGGCAGGGTCAGGGTTC (SEQ ID NO: 41) |
| TCRγ | ACACTCTTTCCCTACACGACGCTCTTCCGATCTGGGGAAACATCTGCATCAAGT (SEQ ID NO: 42) |

| | Primer sequences of P5-IgL/TCRβ/TCRδ (light) mix |
|---|---|
| IgKJ1 | ACACTCTTTCCCTACACGACGCTCTTCCGATCTTTTGATCTCCACCTTGGTCCCTCCGC (SEQ ID NO: 43) |
| IgKJ2 | ACACTCTTTCCCTACACGACGCTCTTCCGATCTTTTGATCTCCAGCTTGGTCCCCTGG (SEQ ID NO: 44) |
| IgKJ3 | ACACTCTTTCCCTACACGACGCTCTTCCGATCTTTTGATATCCACTTTGGTCCCAGGGC (SEQ ID NO: 45) |
| IgKJ4 | ACACTCTTTCCCTACACGACGCTCTTCCGATCTTTTGATTTCCACCTTGGTCCCTTGGC (SEQ ID NO: 46) |
| IgKJ5 | ACACTCTTTCCCTACACGACGCTCTTCCGATCTTTTTAATCTCCAGTCGTGTCCCTTGGC (SEQ ID NO: 47) |
| IgLJ1 | ACACTCTTTCCCTACACGACGCTCTTCCGATCTGAGGACGGTCACCTTGGTGCCA (SEQ ID NO: 48) |
| IgLJ2 | ACACTCTTTCCCTACACGACGCTCTTCCGATCTTAGGACGGTCAGCTTGGTCCCTCC (SEQ ID NO: 49) |
| IgLJ3 | ACACTCTTTCCCTACACGACGCTCTTCCGATCTGAGGACGGTCAGCTGGGTGCC (SEQ ID NO: 50) |
| IgLJ4 | ACACTCTTTCCCTACACGACGCTCTTCCGATCTTAAAATGATCAGCTGGGTTCCTCCAC (SEQ ID NO: 51) |
| IgLJ5 | ACACTCTTTCCCTACACGACGCTCTTCCGATCTTAGGACGGTGACCTTGGTCCCAGT (SEQ ID NO: 52) |
| IgLJ6 | ACACTCTTTCCCTACACGACGCTCTTCCGATCTTAGGACGGTCAGCTCGGTCCCC (SEQ ID NO: 53) |
| TCRβ1 | ACACTCTTTCCCTACACGACGCTCTTCCGATCTGGGAGATCTCTGCTTCTGATG (SEQ ID NO: 54) |
| TCRβ2 | ACACTCTTTCCCTACACGACGCTCTTCCGATCTCGACCTCGGGTGGGAACAC (SEQ ID NO: 55) |
| TCRδ | ACACTCTTTCCCTACACGACGCTCTTCCGATCTCGGATGGTTTGGTATGAGGC (SEQ ID NO: 56) |

A "P7-index-C7" primer was used comprising the concatenation of Illumina C7, 6-base barcode, and P7 sequences:

(SEQ ID NO: 57)
5' CAAGCAGAAGACGGCATACGAGAT[NNNNNN]GTGACTGGAGTTCAGACGTGTGCTCTTCCGATCT 3'.

The following program was run in a thermocycler:
1. 98° C. for 01:00
2. 98° C. for 00:10
3. 64° C. for 00:20
4. 72° C. for 00:20
5. Go to 2 for a total of 6 cycles
6. 4° C. no time limit PCR product was purified with 1.2 volumes of AMPure and eluted in 40 µL Dilution Buffer.

Example 8

Protocol for Third PCR Reaction (PCR3) of Polynucleotides for Next Generation Sequencing for Performing Emulsion-Based, Massively High Throughput Single-Cell Polynucleotide Sequencing 8 µL of purified PCR2 product was used for qPCR to determine a final number of amplification cycles. A set up for the third PCR reaction is shown in Table 4 below.

TABLE 4

| qPCR3a Library | | | |
|---|---|---|---|
| Reagent | Stock Conc. | Final Conc. | 20 µL rxn |
| Q5 buffer 5X | 5.00 mM | 1.00 µM | 4.00 µL |
| Each dNTPs | 10.00 mM | 0.20 µM | 0.40 µL |
| SYBR Green I 1:500 | 83.00 mM | 1.00 µM | 0.24 µL |
| Q5 Hot Start | 125.00 mM | 1.00 µM | 0.16 µL |
| C5-P5 primer | 10.00 µM | 0.40 µM | 0.80 µL |
| C7 primer | 10.00 µM | 0.40 µM | 0.80 µL |
| cDNA | | | 8.00 µL |
| H₂O | | | 5.60 µL |

TABLE 4-continued qPCR3a Library

Primer sequences

| P5 | AATGATACGGCGACCACCGAGATCTACACTCTTTCCCTACACGACGCTCTTCCGATCT (SEQ ID NO: 58) |
| C7 | CAAGCAGAAGACGGCATACGAGAT (SEQ ID NO: 59) |

The following program was run in a qPCR machine:
1. 98° C. for 01:00
2. 98° C. for 00:10
3. 64° C. for 00:20
4. 72° C. for 00:20
5. Read plate
6. Go to 2 for a total of 25 cycles
7. 4° C. no time limit The qPCR intensity plot was inspected to determine the amplification cycle at which fluorescence intensity was maximal but at which exponential amplification of DNA had not yet ended. This was the final cycle number for the PCR3 endpoint.

24.0 µL of purified PCR2 product was used for the endpoint PCR3. An exemplary set up for the PCR reaction to determine the cycle number of the endpoint of the third PCR is shown in Table 5 below.

TABLE 5 qPCR3b Library

| Reagent | Stock Conc. | Final Conc. | 60 µL rxn |
|---|---|---|---|
| Q5 buffer 5X | 5.00 mM | 1.00 µM | 12.00 µL |
| Each dNTPs | 10.00 mM | 0.20 µM | 1.20 µL |
| H$_2$O | 83.00 mM | 1.00 µM | 0.72 µL |
| Q5 Hot Start | 125.00 mM | 1.00 µM | 0.48 µL |
| C5-P5 primer | 10.00 µM | 0.40 µM | 2.40 µL |
| C7 primer | 10.00 µM | 0.40 µM | 2.40 µL |
| cDNA | | | 24.00 µL |
| H$_2$O | | | 16.80 µL |

The following program was run in a thermocycler:
1. 98° C. for 01:00
2. 98° C. for 00:10
3. 64° C. for 00:20
4. 72° C. for 00:20
5. Go to 2 for the determined number of cycles
6. 4° C. no time limit The PCR product was purified with 1.2 volumes of AMPure and eluted in 20 µL of Dilution Buffer. The libraries were ready for sequencing. They were be pooled as desired, with or without agarose gel purification to remove contaminating truncated amplicons and then sequenced using a next generation sequencing technology platform.

Example 9

Read Processing and Isotype Assignment

Illumina MiSeq reads were processed using custom pipelines built around the pRESTO packagel to generate full length consensus sequences for mRNA molecules and droplets, annotated with IgBLAST and IMGT/HighV-QUEST, and processed with custom scripts and the Change-O package to generate statistics and figures. MiSeq reads were demultiplexed using Illumina software. Positions with less than Phred quality 5 were masked with Ns. Isotype-specific primers, droplet barcodes (DBs), and molecular barcodes (MBs) were identified in the amplicon and trimmed, using pRESTO MaskPrimers-cut with a maximum error of 0.2. A read 1 consensus sequence and a read 2 consensus sequence was generated separately for each mRNA from reads grouped by unique molecular identifier (UMI) comprising the DB and MB together, which are PCR replicates arising from the same original mRNA molecule of origin. UMI read groups were aligned with MUSCLE, and pRESTO was used to build consensus sequences with the following parameters: maxdiv=0.1; bf PRIMER; prfreq=0.6; maxmiss=0.5; q=5; ≥60% of called PCR primer sequence agreement for the read group; maximum nucleotide diversity=0.1; using majority rule on indel positions; and masking alignment columns with low posterior (consensus) quality. Paired end consensus sequences were then stitched in two rounds. First, ungapped alignment of each read pair's consensus sequence termini was optimized using a Z-score approximation and scored with a binomial p-value as implemented in pRESTO AssemblePairs-align with the following parameters: minimum length=8; alpha $1\times10^{-5}$; and maximum error=0.3. For read pairs failing to stitch this way, stitching was attempted using the human BCR and TCR germline V exons to scaffold each read prior to stitching or gapped read-joining, using pRESTO's AssemblePairs-reference parameters: minimum identity=0.5; e value $1\times10^{-5}$.

Example 10

V(D)J Segment Annotation and Isotype Confirmation

IgBLAST, Change-O, and custom scripts were used to identify the germline V(D)J genes of origin, trim mRNA sequences to a V(D)J region, identify CDR3 regions, and calculate the mutation from germline V nucleotide sequences. IgBLAST counts Ns as mismatches but mRNA sequences with more than 6 V-region Ns were filtered for mutation analyses and cross-fraction pairing precision analysis. For IG heavy chains, isotype identity was confirmed by matching non-primer C-regions (constant region exons) to expected sequences using pRESTO MaskPrimers-score parameters: start=0; maximum error=0.2. Amplicons with discordant primer/non-primer C-region calls were discarded, except for two primer/non-primer combinations where a specific primer crosstalk event was resolved by visual inspection.

Example 11

Grouping V(D)J Sequences into Clonal Lineages

V(D)J sequences were grouped into clones using single-linkage clustering with a weighted intraclonal distance. Clustering was performed with Change-O package Define-Clones-by group parameters: model=min; gene=first; dist=4.0; norm=none. First, all functional Ig $V_H$ chains' droplet consensus sequences were binned into V-J junction bins, such that sequences possibly arising from the same initial recombination event were binned together (based on best matching Ig $V_H$ gene, best matching Ig $J_H$ gene, and junction length as identified by IMGT/HighV-QUEST. The intraclonal distance threshold was chosen by generating a histogram of nearest-neighbor distances within each Ig $V_H$ bin using the distToNearest function of Change-O's shm package, and visually inspecting the histogram for a natural distance cutoff (in the trough of a bimodal histogram). Light chains' clonal clusters were defined using the same distance model and threshold.

Example 12

Droplet Filtering, Pairing Fidelity Calculation

Heavy-light pairing confidence was assessed in two independent ways: using intradroplet mRNA sequence agreement, and inter-replicate pair agreement. Intradroplet mRNA agreement was defined as mean pairwise nucleotide difference (Nei's pi≤0.02) of V(D)J sequences within a locus. mRNA sequences were trimmed down to V(D)J nucleotide coding sequences using IgBLAST annotations. Within each droplet all productive mRNA sequences were grouped by V locus. Within each group, multiple sequences were aligned using MUSCLE as implemented in pRESTO AlignSets using default parameters. Droplet consensus chains were built from multiple mRNAs per locus using the pRESTO parameters: BuildConsensus.py; maximum div=0.2; maximum miss=0.5. Randomly shuffled droplets were used to select the diversity cutoff pi≤0.02. In shuffled droplets, less than 0.01% of heavy chain loci (<0.2% of light chain loci) met this criteria. Multi-cell or immune-receptor included droplets were separated for further precision analysis.

Pairing precision was calculated based on observation of the same clone-pair across multiple replicates (separate emulsion experiments), focusing on those VDJ clusters likely containing only a single lineage, i.e., arising from a single V(D)J and VJ rearrangement followed by expansion. Similar VDJ rearrangements can arise within an individual multiple independent times, leading to the same heavy chain V(D)J rearrangement natively paired with multiple different light chain VJ rearrangements. Because rare V(D)J rearrangements would provide a more accurate measure of the technical precision achieved by the methods described herein, long heavy CDR3s ($CDR3_H$) for a focus for this analysis (as a proxy for rarer V(D)J rearrangements). Sequences with >6 Ns were also removed to increase clonal assignment confidence. Pairing precision increased with $CDR3_H$ length to over 96% for the longest quartile of clones observed across fractions (2,604 clones with junction length ≥54 nt). Because the probability of clone-pair agreements is the joint probability of true pairs in two independent experiments, pairing precision was estimated as the square root of the pairing agreement across replicates, calculated as follows where $d_{hi}^f$ is the number of droplet barcodes d with paired heavy clone h and light clone l, and found in physical fraction f. Mean (squared) pairing precision for each experiment is estimated by averaging, over heavy clones h and all pairs of fractions (f, g), the agreement of paired light clones (l, k):

$$\langle \text{precision}^2 \rangle = \text{mean}(P_f P_g) = \frac{\text{consistent heavy light pairs across fractions}}{\text{total pairs where heavy clone seen across fractions}}$$

$$\frac{\text{consistent heavy light pairs}}{\text{consistent pairs} + \text{inconsistent pairs}} = \frac{\Sigma_h \left( \sum_{l=k}^{f \neq g} d_{hl}^f \cdot d_{hk}^g \right)}{\Sigma_h \left( \sum_{l=k}^{f \neq g} d_{hl}^f \cdot d_{hk}^g + \sum_{l \neq k}^{f \neq g} d_{hl}^f \cdot d_{hk}^g \right)}$$

$$\langle \text{precision}^2 \rangle = \frac{33157}{35922}$$

Therefore the mean precision of each experiment, (to within the variance in precision between experiments) was 96.1% according to this exemplary experiment.

Example 13

HIV Phylogenetic Analysis

New broadly-neutralizing antibodies (bNAbs) to HIV were discovered by mining our high-throughput paired antibody processed sequences for similarity to known bNAbs. Previously known bNAbs from PGT-donor and other donors were mined from the literature. All HIV IgH mRNAs recovered from emulsions were scored for similarity to known CDR3 amino acid sequences via tblastx 10. Using IgH mRNA sequences from a healthy donor to generate a background distribution of sequence similarities, a bit score cutoff of 27 was used to segregate candidate bNAb-like CDR3s for further analysis. V(D)J sequences of candidate sequences were aligned to known bNAb's using MUSCLE 11 with default parameters, and in particular to PGT-donor lineages using default parameters except: gapopen=−15. Trees were generated with PhyML default parameters, manipulated and visualized with Newick Utils and Dendroscope and manually inspected to select immunoglobulin heavy chain sequences interspersing with known bNAbs sequences. Consensus sequences for each droplet were built as previously described with manual inspection of alignments of any within-droplet amino acid conflicts using in JALVIEW. Eight heavy chain sequences and their natively paired light chain antibody sequences were selected for synthesis, cloning, expression, and neutralization assays.

Example 14

Data Analysis and Plotting

Plots were generated using the dplyr and ggplot2 R packages. Data was randomly down-sampled and/or jittered with R for visualization purposes only in scatter plot figures. Down-sampling minimum was 20,000 droplets per isotype or as otherwise noted. Points were jittered by adding vertical and horizontal noise drawn from the same uniform probability distribution, with maxima ≤0.2 for mRNA units and ≤0.6% for mutation.

What is claimed is:

1. A method comprising:
   (a) forming a plurality of vessels each vessel of the plurality comprising a single cell from a sample comprising a plurality of cells, a plurality of molecular-barcoded oligonucleotide molecules each comprising a unique molecular barcode, and a vessel-barcoded oligonucleotide comprising a vessel barcode;
   (b) producing within one or more vessels of the plurality (i) a first complementary polynucleotide that is complementary to a first cell polynucleotide from the single cell and (ii) a second complementary polynucleotide that is complementary to a second cell polynucleotide from the single cell; and subsequently
   (c) forming a first molecular-barcoded polynucleotide and a second molecular-barcoded polynucleotide; and
   (d) forming a first vessel-molecular-barcoded polynucleotide and a second vessel-molecular-barcoded polynucleotide;
   wherein the molecular-barcoded oligonucleotide molecules of the plurality and the vessel barcoded oligonucleotide in (a) are separate nucleic acid molecules.

2. The method of claim 1, wherein the first cell polynucleotide is a heavy chain immunoglobulin (IgH) polynucleotide, a T-cell receptor alpha (TCRα) polynucleotide, or a T-cell receptor gamma (TCRγ) polynucleotide; and wherein the second cell polynucleotide is a light chain immunoglobulin (IgL) polynucleotide, a T-cell receptor beta (TCRβ) polynucleotide, or a T-cell receptor delta (TCRδ) polynucleotide.

3. The method of claim 1, further comprising amplifying the first and the second vessel-molecular-barcoded polynucleotides.

4. The method of claim 1, further comprising sequencing the first and the second vessel-molecular-barcoded polynucleotide or amplified products thereof.

5. The method of claim 1, wherein the single cell is a B-cell or a T-cell.

6. The method of claim 1, wherein the first and the second vessel-molecular-barcoded polynucleotides in a single vessel of the plurality comprise different molecular barcodes.

7. The method of claim 1, wherein the molecular-barcoded oligonucleotide molecules of the plurality are not amplified products.

8. The method of claim 1, wherein a molecular barcode of a molecular-barcoded oligonucleotide molecule of the plurality in a first vessel of the plurality is different than a molecular barcode of a molecular-barcoded oligonucleotide molecule of the plurality in a second vessel of the plurality.

9. The method of claim 1, wherein a vessel barcode of a vessel-barcoded oligonucleotide in a first vessel of the plurality is different from a vessel barcode of a vessel-barcoded oligonucleotide in a second vessel of the plurality.

10. The method of claim 1, wherein the vessel-barcoded oligonucleotide in each vessel of the plurality in (a) is present as a single molecule.

11. The method of claim 1, wherein the vessel barcode of the first and the second vessel-molecular-barcoded polynucleotides in a single vessel of the plurality are the same.

12. The method of claim 1, wherein the vessel-barcoded oligonucleotides in two or more different vessels of the plurality comprise a first common-vessel sequence upstream of their vessel barcode, a second common-vessel sequence downstream of their vessel barcode, or both.

13. The method of claim 1, wherein each of the molecular-barcoded oligonucleotide molecules of the plurality in a same vessel of the plurality comprises a first common-molecular sequence upstream of their molecular barcode, a second common-molecular sequence downstream of their molecular barcode, or both.

14. The method of claim 1, wherein each of the molecular-barcoded oligonucleotide molecules of the plurality in each vessel of the plurality comprises a first common-molecular sequence upstream of the molecular barcode, a second common-molecular sequence downstream of the molecular barcode, or both.

15. The method of claim 1, wherein the vessel-barcoded oligonucleotide or a complement thereof comprises a sequence complementary to a region of a complement of each molecular-barcoded oligonucleotide molecule of the plurality.

16. The method of claim 1, wherein the vessel-barcoded oligonucleotide or a complement thereof comprises a sequence complementary to a 3' end region of the first and the second molecular-barcoded polynucleotides.

17. The method of claim 1, wherein one or more of the following are not fused together:
  (i) a first and a second molecular-barcoded oligonucleotide molecule of the plurality,
  (ii) the first and the second molecular-barcoded polynucleotides, and
  (iii) the first and the second vessel-molecular-barcoded polynucleotides.

18. The method of claim 1, wherein (b) comprises extending a first target primer hybridized to a common-sequence of the first cell polynucleotide and extending a second target primer hybridized to a common-sequence of the second cell polynucleotide, wherein the first and the second target primers are extended by a reverse transcriptase comprising a non-template terminal transferase activity, wherein 3 or more identical non-template nucleotides are added to a 3' end of the first and the second complementary polynucleotides.

19. The method of claim 1, wherein the forming of (c) comprises hybridizing a 3' end region of the first and the second molecular-barcoded oligonucleotide molecules of the plurality to 3 or more non-template nucleotides present on a 3' end of the first and the second complementary polynucleotides, respectively.

20. The method of claim 19, wherein the forming of (c) further comprises extending the 3' end of the first and the second complementary polynucleotides.

21. The method of claim 1, wherein the vessels of the plurality are emulsions.

22. The method of claim 1, wherein the single cell is lysed before (b).

23. The method of claim 1, wherein a first target primer, a second target primer, the vessel-barcoded oligonucleotide, the plurality of molecular-barcoded oligonucleotide molecules, or any combination thereof, is not attached to a solid support.

24. The method of claim 1, wherein (b)-(d) are performed in a same single vessel of the plurality.

25. The method of claim 1, wherein the first and the second cell polynucleotides are RNA.

26. The method of claim 1, further comprising determining the first and the second cell polynucleotide to be from a same cell based on the vessel barcode.

27. The method of claim 1, further comprising determining a germ line sequence of the first cell polynucleotide, the second cell polynucleotide, or both.

28. The method of claim 27, further comprising determining a variance of a sequence of the first or second cell polynucleotide from the respective germ line sequence, or both.

29. The method of claim 1, further comprising determining at least one of:
  (a) a total number of unique first cell polynucleotide sequences;
  (b) a total number of unique second cell polynucleotide sequences;
  (c) a total number of unique paired first and second cell polynucleotide sequences;
  (d) a frequency of a sequence of a first cell polynucleotide sequence;
  (e) a frequency of a sequence of a second cell polynucleotide; and
  (f) a frequency of sequence of a first cell polynucleotide and a sequence of a second cell polynucleotide that are paired.

30. The method of claim 1, further comprising determining a number of starting molecules with a sequence of the first or second cell polynucleotide, or both, based on the unique molecular barcode.

31. The method of claim 1, wherein the first molecular-barcoded polynucleotide comprises the molecular barcode of a first molecular-barcoded oligonucleotide molecule of the plurality or an amplified product thereof and the first complementary polynucleotide or an amplified product thereof, and the second molecular-barcoded polynucleotide comprises the molecular barcode of a second molecular-barcoded oligonucleotide molecule of the plurality or an amplified product thereof and the second complementary polynucleotide or an amplified product thereof.

32. The method of claim 1, wherein the first vessel-molecular-barcoded polynucleotide comprises the vessel barcode of the vessel-barcoded oligonucleotide or an amplified product thereof and the first molecular-barcoded polynucleotide or an amplified product thereof, and the second vessel-molecular-barcoded polynucleotide comprises the vessel barcode of the vessel-barcoded oligonucleotide or an amplified product thereof and the second molecular-barcoded polynucleotide or an amplified product thereof.

33. The method of claim 1, wherein (b)-(d) are performed in two or more vessels of the plurality simultaneously.

34. The method of claim 1, wherein the forming of (c) comprises attaching a first molecular-barcoded oligonucleotide molecule of the plurality to the first complementary polynucleotide and attaching a second molecular-barcoded oligonucleotide molecule of the plurality to the second complementary polynucleotide.

35. The method of claim 1, wherein the forming of (d) comprises attaching a first vessel-barcoded oligonucleotide molecule to the first molecular-barcoded polynucleotide and attaching a second vessel-barcoded oligonucleotide molecule to the second molecular barcoded polynucleotide.

36. The method of claim 1, wherein the plurality of vessels comprises at least 1000 vessels.

37. A method of barcoding polynucleotides comprising:
  (a) forming a plurality of vessels, each vessel of the plurality comprising a single cell from a sample comprising a plurality of cells, a plurality of molecular-barcoded oligonucleotide molecules each comprising a unique molecular barcode, and a vessel-barcoded oligonucleotide comprising a vessel barcode;
  (b) producing within one or more vessels of the plurality (i) a first complementary polynucleotide that is complementary to a first cell polynucleotide from the single cell and (ii) a second complementary polynucleotide that is complementary to a second cell polynucleotide from the single cell; and subsequently
  (c) forming a first molecular-barcoded polynucleotide and a second molecular-barcoded polynucleotide;

(d) amplifying a vessel-barcoded oligonucleotide to generate one or more copies of the vessel-barcoded oligonucleotide;

(e) hybridizing a first copy of the one or more copies of the vessel-barcoded oligonucleotide to the first molecular-barcoded polynucleotide and hybridizing a second copy of the one or more copies of the vessel-barcoded oligonucleotide to the second molecular-barcoded polynucleotide; and (f) forming a first vessel-molecular-barcoded polynucleotide and a second vessel-molecular-barcoded polynucleotide.

38. The method of claim 37, wherein the hybridizing of (e) comprises (i) hybridizing a region of the first copy of the vessel-barcoded oligonucleotide or a complement thereof to a 3' end of the first molecular-barcoded polynucleotide and (ii) hybridizing a region of the second copy of the vessel-barcoded oligonucleotide or a complement thereof to a 3' end of the second molecular-barcoded polynucleotide.

39. The method of claim 38, wherein the forming of (c) comprises extending the 3' end of the first molecular-barcoded polynucleotide and extending the 3' end of the second molecular-barcoded polynucleotide.

\* \* \* \* \*

SEQUENCE LISTING

<160> NUMBER OF SEQ ID NOS: 59

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggttggggc ggatgcac                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catccggagc cttggtgg                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccttggggct ggtcgggg                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggatgggct ctgtgtgg                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgatgggcc cttggtgg                                                 18

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatttagag tctctcagct g                                             21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cacggcaggg tcagggttc                                                19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggggaaacat ctgcatcaag t                                             21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttgatctcc accttggtcc ctccgc                                        26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttgatctcc agcttggtcc cctgg                                         25

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttgatatcc actttggtcc cagggc                                        26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgatttcc accttggtcc cttggc                                        26

```
<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttaatctcc agtcgtgtcc cttggc                                          26

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaggacggtc accttggtgc ca                                              22

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taggacggtc agcttggtcc ctcc                                            24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaggacggtc agctgggtgc c                                               21

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
taaaatgatc agctgggttc ctccac                                          26

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taggacggtg accttggtcc cag                                             23
```

```
<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggagatctc tgcttctgat g                                              21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgacctcggg tgggaacac                                                 19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggatggttt ggtatgaggc                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (6)..(9)
<223> OTHER INFORMATION: a, c, t, g, unknown or other
<220> FEATURE:
<221> NAME/KEY: modified_base
<222> LOCATION: (11)..(14)
<223> OTHER INFORMATION: a, c, t, g, unknown or other
<220> FEATURE:
<221> NAME/KEY: modified_base
<222> LOCATION: (16)..(19)
<223> OTHER INFORMATION: a, c, t, g, unknown or other

<400> SEQUENCE: 22
nnnnwnnnnw nnnnwnnnnw                                                20

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
```

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (27)..(27)
<223> OTHER INFORMATION: a, c, t, g, unknown or other

<400> SEQUENCE: 24
tttttttttt tttttttttt tttttvn                                27

<210> SEQ ID NO 25
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (30)..(33)
<223> OTHER INFORMATION: a, c, t, g, unknown or other
<220> FEATURE:
<221> NAME/KEY: modified_base
<222> LOCATION: (35)..(38)
<223> OTHER INFORMATION: a, c, t, g, unknown or other
<220> FEATURE:
<221> NAME/KEY: modified_base
<222> LOCATION: (40)..(43)
<223> OTHER INFORMATION: a, c, t, g, unknown or other

<400> SEQUENCE: 25
atccatccac gactgacgga cgtattaaan nnnwnnnnwn nnnagatcgg aagagcacac     60
gtctgaactc cagtcacc                                                  78

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (24)..(25)
<223> OTHER INFORMATION: a, c, t, g, u, unknown or other
<220> FEATURE:
<221> NAME/KEY: modified_base
<222> LOCATION: (27)..(28)
<223> OTHER INFORMATION: a, c, t, g, u, unknown or other
<220> FEATURE:
<221> NAME/KEY: modified_base
<222> LOCATION: (30)..(31)
<223> OTHER INFORMATION: a, c, t, g, u, unknown or other

<400> SEQUENCE: 26
aatacgtccg tcagtcgtgg atgnntnnan ntggg                                35

<210> SEQ ID NO 27
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 27
catccacgac tgacggacgt att                                              23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgactggag ttcagacgtg tgct                                             24

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cacggcaggg tcagggttc                                                   19

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaaatagtgg gcttgggg                                                    18

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
taggacggtg accttggtcc cagt                                             24

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgacctcggg tgggaacac                                                   19

<210> SEQ ID NO 33
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 33
agacaagcga catttgttcc a                                              21

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgactggag ttcagacgtg tgctcttccg atct                                34

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acactctttc cctacacgac gctcttccga tctgggttgg ggcggatgca c              51

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acactctttc cctacacgac gctcttccga tctcatccgg agccttggtg g              51

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acactctttc cctacacgac gctcttccga tctccttggg gctggtcggg g              51

<210> SEQ ID NO 38
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acactctttc cctacacgac gctcttccga tctcggatgg gctctgtgtg g              51

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
acactctttc cctacacgac gctcttccga tctccgatgg gcccttggtg g         51

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acactctttc cctacacgac gctcttccga tctggattta gagtctctca gctg      54

<210> SEQ ID NO 41
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acactctttc cctacacgac gctcttccga tctcacggca gggtcagggt tc        52

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acactctttc cctacacgac gctcttccga tctggggaaa catctgcatc aagt      54

<210> SEQ ID NO 43
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acactctttc cctacacgac gctcttccga tcttttgatc tccaccttgg tccctccgc    59

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acactctttc cctacacgac gctcttccga tcttttgatc tccagcttgg tccctgg      58

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acactctttc cctacacgac gctcttccga tcttttgata tccactttgg tcccagggc        59

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acactctttc cctacacgac gctcttccga tcttttgatt tccaccttgg tcccttggc        59

<210> SEQ ID NO 47
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acactctttc cctacacgac gctcttccga tcttttaatc tccagtcgtg tcccttggc        59

<210> SEQ ID NO 48
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acactctttc cctacacgac gctcttccga tctgaggacg gtcaccttgg tgcca            55

<210> SEQ ID NO 49
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acactctttc cctacacgac gctcttccga tcttaggacg gtcagcttgg tccctcc          57

<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acactctttc cctacacgac gctcttccga tctgaggacg gtcagctggg tgcc             54

<210> SEQ ID NO 51
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acactctttc cctacacgac gctcttccga tcttaaaatg atcagctggg ttcctccac    59

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acactctttc cctacacgac gctcttccga tcttaggacg gtgaccttgg tcccagt    57

<210> SEQ ID NO 53
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acactctttc cctacacgac gctcttccga tcttaggacg gtcagctcgg tcccc    55

<210> SEQ ID NO 54
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acactctttc cctacacgac gctcttccga tctgggagat ctctgcttct gatg    54

<210> SEQ ID NO 55
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acactctttc cctacacgac gctcttccga tctcgacctc gggtgggaac ac    52

<210> SEQ ID NO 56
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acactctttc cctacacgac gctcttccga tctcggatgg tttggtatga ggc    53

<210> SEQ ID NO 57
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (25)..(30)
<223> OTHER INFORMATION: a, c, t, g, unknown or other

<400> SEQUENCE: 57
caagcagaag acggcatacg agatnnnnnn gtgactggag ttcagacgtg tgctcttccg    60
atct                                                                64

<210> SEQ ID NO 58
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aatgatacgg cgaccaccga gatctacact ctttccctac acgacgctct tccgatct     58

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
caagcagaag acggcatacg agat                                          24
```